United States Patent [19]
Kuhar et al.

[11] Patent Number: 5,935,953
[45] Date of Patent: Aug. 10, 1999

[54] METHODS FOR CONTROLLING INVERTEBRATE PESTS USING COCAINE RECEPTOR BINDING LIGANDS

[75] Inventors: Michael J. Kuhar, Baltimore, Md.; Frank I. Carroll, Durham, N.C.; John W. Boja, Baltimore, Md.; Anita H. Lewin, Chapel Hill; Philip Abraham, Cary, both of N.C.

[73] Assignee: Research Triangle Institute, Research Triangle Park, N.C.

[21] Appl. No.: 08/823,563

[22] Filed: Mar. 25, 1997

Related U.S. Application Data

[63] Continuation-in-part of application No. 08/706,263, Sep. 4, 1996, and a continuation-in-part of application No. 08/701,503, Aug. 22, 1996, which is a continuation-in-part of application No. 08/506,541, Jul. 24, 1995, which is a continuation-in-part of application No. 08/436,970, May 8, 1995, Pat. No. 5,736,123, which is a continuation-in-part of application No. 07/972,472, Aug. 9, 1991, Pat. No. 5,413,779, which is a continuation-in-part of application No. 07/564,755, Aug. 9, 1990, Pat. No. 5,128,118.

[51] Int. Cl.$^6$ ..................... A61K 31/535; A61K 31/44; A01N 43/42; C07D 451/02
[52] U.S. Cl. ................. 514/235.2; 514/304; 514/315; 514/323; 546/125; 546/126; 546/132; 424/1.81; 424/405
[58] Field of Search ................. 424/1.81, 405; 546/124, 125, 126, 132; 514/252, 255, 304, 235.2, 315, 323

[56] References Cited

U.S. PATENT DOCUMENTS

| | | |
|---|---|---|
| 3,813,404 | 5/1974 | Clark et al. |
| 5,128,118 | 7/1992 | Kuhar et al. ............... 424/1.85 |
| 5,366,975 | 11/1994 | Nathanson ............... 514/255 |
| 5,374,636 | 12/1994 | Moldt et al. |
| 5,380,848 | 1/1995 | Kuhar et al. ............... 546/124 |
| 5,413,779 | 5/1995 | Kuhar et al. ............... 424/1.85 |
| 5,496,953 | 3/1996 | Kuhar et al. ............... 546/125 |

OTHER PUBLICATIONS

Maarten E. A. Reith et al., "Structural Requirements for cocaine congeners to interact with Dopamine and serotonin uptake sites in mouse brain and to induce stereotyped behavior", Biochemical Pharmacology, vol. 35, No. 7, pp. 1123–1129, 1986.

*Primary Examiner*—José G. Dees
*Assistant Examiner*—Michael G. Hartley
*Attorney, Agent, or Firm*—Oblon, Spivak, McClelland, Maier & Neustadt, P.C.

[57] ABSTRACT

The invention relates to a method of controlling an invertebrate pest, comprising contacting the pest with a pest-controlling amount of an agent having substantial inhibitory activity toward a phenylethanolamine reuptake transporter as determined by radioactive octopamine reuptake inhibition assay is disclosed. Compositions comprising compounds capable of inhibiting the octopamine reuptake transporter include cocaine analogs. A process for inhibiting the feeding of an invertebrate pest comprising contacting said pest with a pest-controlling amount of an agent having substantial inhibitory activity toward a phenylethanolamine reuptake transporter as determined by radioactive octopamine reuptake inhibition assay, with the proviso that said agent is not cocaine. A process for delaying the maturation of a juvenile invertebrate by contacting it with an inhibitory amount of a phenylethanolamine reuptake transporter blocker is also disclosed. A radioactive phenylethanolamine reuptake inhibition assay for determining whether a given compound is an inhibitor of octopamine neuronal transport is also disclosed.

10 Claims, 8 Drawing Sheets

| | | |
|---|---|---|
| RTI-165 | X = CL | R = CH₃ |
| RTI-171 | X = CH₃, | R = CH₃ |
| RTI-180 | X = I, | R = CH₃ |
| RTI-177 | X = CL | R = Ph |
| RTI-176 | X = CH₃, | R = Ph |
| RTI-181 | X = I, | R = Ph |
| RTI-334 | X = CL, | R = C₂H₅ |
| RTI-335 | X = CL, | R = C₁₁(CH₃)₂ |
| RTI-336 | X = CL, | R = C₆H₄CH₃ |
| RTI-337 | X = CL, | R = C(CH₃)₃ |
| RTI-345 | X = CL, | R = C₆H₄Cl |
| RTI-346 | X = CL, | R = C₆H₄OCH₃ |
| RTI-347 | X = CL, | R = C₆H₄F |
| RTI-354 | X = CH₃, | R = C₂H₅ |

1. (R)-(−)COCAINE

2. WIN 35,065-2

|   | R1 | R2 | R3 | R4 |
|---|----|----|----|----|
| 3. | −OH | −Ph | −Ph | −H |
| 4. (2-TROPENE) | — | −Ph | −Ph | — |
| 5. | −Ph | −H | −Ph | −H |
| 6. | −H | −Ph | −H | −Ph |

12a.  R = OC(O)Ph
12b.  WIN 35,065-2: R = Ph 13a.  2β, 3β-ISOMER
13b.  2α, 3β-ISOMER
13c.  2β, 3α-ISOMER
13d.  2α, 3α-ISOMER

14.

15.

METHODS FOR CONTROLLING INVERTEBRATE PESTS USING COCAINE RECEPTOR BINDING LIGANDS

This application is a continuation-in-part of 08/706,263, filed Sep. 4, 1996, pending, and is a continuation-in-part of 08/701,503, filed Aug. 22, 1996, pending, which is a continuation-in-part of 08/506,541, filed Jul. 24, 1995, pending, which is a continuation-in-part of 08/436,970, filed May 8, 1995, now U.S. Pat. No. 5,736,123, which is a continuation-in-part of 07/972,472, filed Aug. 9, 1991, now U.S. Pat. No. 5,413,779, which is a continuation-in-part of 07/564,755, filed Aug. 9, 1990, now U.S. Pat. No. 5,128,118, all of which are herein incorporated by reference in their entirety. Also incorporated herein by reference in its entirety is U.S. Pat. No. 5,366,975, issued Nov. 22, 1994.

GOVERNMENT SUPPORT

This work was supported in part by grant No. DA05477 from the National Institute on Drug Abuse. The government may have certain rights in the invention.

BACKGROUND OF THE INVENTION

1. Field of the Invention

This invention is directed to a class of compounds which are cocaine analogs, and which inhibit catecholamine, ago endoleamine, octopamine and phenylethanolamine reuptake transporters. Specifically, a novel family of compounds shows high binding specificity and activity, and can-be used to bind to these transporters. Such binding, and the inhibition of the transporter which results, is useful for controlling invertebrate pests, including inhibiting the feeding of and delaying the maturation of the invertebrate pests. The compounds also have a reduced ability to cross the blood-brain barrier in animals, and thus, the compounds are safe for use as insecticides.

2. Description of the Related Art

In mammals, the CNS stipulatory and euphoric effects of cocaine are thought to be due to cocaine's well-documented action in blocking dopamine (DA) reuptake into presynaptic nerve terminals (Jaffe, J., in The Pharmacological Basis of Therapeutics, Gilman, A. G., et al. , eds., MacMillan: New York, pp. 535–584 (1980); Kennedy, L., et al., J. Neurochem. 41: 172–178 (1983) Kuhar et al. 1991). Because amine reuptake is a major mechanism for inactivation of DA following its synaptic release, the effect of cocaine is to augment and prolong DA neurotransmission. In man, with moderate amounts of cocaine, this results several physiologic and psychologic effects (Jaffe 1980).

Pharmacological evidence from vertebrates supports the presence of distinct reuptake sites (amine transporter proteins) for DA, NE, and serotonin (5-HT) (Ritz, M., et al., NIDA Research Monograph 95: 239–246 (1989)). Although much recent emphasis has been put on cocaine's action on DA, older literature clearly indicates that cocaine also blocks the reuptake of NE and 5-HT (Baldessarini, R., et al., J. Neurochem. 18: 2519–2533 (1971); Body, T., et al. , Pharmacol. Biochem. & Behavior 34: 165–172 (1989)).

Early biochemical studies of monoamine reuptake in mammals involved the use of living animals injected with labeled amines or the use of intact, isolated organs or tissue fragments incubated in vitro with tracer (Hertting et al., J. Pharmacol. Exp. Ther. 134: 146–153 (1961); Dengler et al., Nature 191: 816–817 (1961); Axelrod and Inscoe, J. Pharmacol. Exp. Ther. 141: 161–165 (1963)). Although these studies yielded important data about reuptake kinetics, they have been less useful for pharmacologically characterizing transporter binding sites and for determining the structure-activity relationships of drugs capable of blocking these sites. This is due to the fact that drug penetration through intact tissues and drug metabolism within tissues can significantly alter measurement of the true affinity of compounds for transporter binding sites. Studies with intact tissue are also tedious and complicate the use of replicate samples because of the tube-to-tube variability in the size and homogeneity of the intact tissue pieces. Thus, many researchers have abandoned the use of intact tissue preparations in the characterization of vertebrate amine transporters and have used, instead, broken cell tissue fractions prepared in such a way as to contain intact pinched-off nerve endings (synaptosomes) capable of accumulating labeled amines under sodium- and energy-dependent conditions (Baldessarini and Vogt, J. Neurochem 18: 2519–2533 (1971); Anderson, J. Neurochem 48: 1887–1896 (1987); Boja and Kuhar, Europ. J. Pharmacol. 173: 215–217 (1989).

Although cocaine has a fascinating medicinal history in man, dating back at least 4500 years, its natural function in plants is unknown (Plowman, T., in Ethnobotany in the Neotropics, France, G. T., et al., eds., N.Y. Botanical Garden, Bronx, N.Y., pp. 62–111 (1984)). Plowman, Rivier and others (Rivier, L., J. Ethnopharmacology 3: 313–335 (1981); Plowman, T., et al., Ann. Bot. (London) 51: 641–659 (1983)) have determined that the four major varieties of Erythroxylum (coca) plants that produce cocaine, contain levels ranging from 0.35–0.72% dry weight, with values often exceeding 1% (particularly in small, newly emerging leaves). Although relatively little is known about the insect pests of coca, Plowman & Well (J. Ethnopharmacology 1: 263–278 (1979)) have commented, on the basis of personal observations, that, compared with other tropical American crops, E. coca and E. novogranatense are relatively pest-free. Herbivorous insects are only rarely observed on the plants in the field; damage to leaves is often minor. This is especially noteworthy since, during much of the year, the membranaceous leaves of coca are found in the tender state of unfolding, the result of their being stripped 3–6 times a year during harvest.

Octopamine (OA) is an invertebrate-specific neurotransmitter which was first discovered over 45 years ago in the posterior salivary gland of the octopus (V. Erspamer and G. Boretti, Arch. Int. Pharmaco. Ther. 88: 926–322 (1951)). Although similar to norepinephrine (NE) in structure, OA has very little activity as a sympathomimetic when injected into mammals (A. Lands and J. Grant, J. Pharm. Exptl. Therap. 106: 341–345 (1952)) and, compared with NE, is present in very low concentrations in vertebrate tissues (Y. Kakimoto and M;. Armstrong, J. Biol. Chem. 237: 422–427 (1962)). Relatively little attention was paid to OA until early 1970's, when Molinoff and Axelrod reported that OA was present in much higher concentrations in invertebrates, particularly in invertebrate nerve tissue (P. B. Molinoff and J. Axelrod, J. Neurochem. 19: 157–163 (1972)).

In 1973, the first identification of an OA receptor was reported (J. A. Nathanson "Cyclic AMP: A Possible Role in Insect Nervous System Function", (Ph.D. Thesis) (1973); J. A. Nathanson and P. Greengard, Science, 19: 308–310 (1973)). Because this receptor was present in highest concentrations in insect nerve cord, it was postulated that OA might function as a neurotransmitter. Furthermore, because these receptors were undetectable in mammalian tissues, it was also postulated that the neurotransmitter function of OA might be largely restricted to invertebrates (J. A. Nathanson "Cyclic AMP: A Possible Role in Insect Nervous System Function", (Ph.D. Thesis) (1973); J. A. Nathanson and P. Greengard, Science, 19: 308–310 (1973); J. A. Nathanson, Trace Amines and the Brain: Eds. Marcel Dekker, pp. 161–190 (1976)). At about the same time, Kravitz and coworkers (B. Wallace et al., Brain Res. 349–55 (1974)) independently reported the presence of OA-containing neurons in crustacea, and, somewhat later, Hoyle reported evidence suggesting the presence of large OA neurons in insect ganglia (G. Hoyle, J. Exp. Zool 193: 425–31 (1975)). Subsequent work by a number of investigators has established the role of OA, not only as a neurotransmitter, but also as a neuromodulator and circulating neurohormone in insects and acarines (for review see I. Orchard, Can. J. Zool, 60: 659–69 (1982); H. A. Robertson and A. V. Juorio, Int. Rev. Neurobiol. 19: 173–224 (1976)). Indeed, OA plays a pervasive role in regulating many areas of insect physiology, including carbohydrate metabolism, lipid mobilization, hematocyte function, heart rate, peripheral muscle tension and excitability, and behavior. The functions that OA carries out in insects appear analogous to those carried out by norepinephrine (NE) and epinephrine (EPI) in vertebrates. This has led to the suggestion that, during evolution, there may have been a divergence in the use of these amines between the two arms of the animal kingdom (H. A. Robertson and A. V. Juorio, Int. Rev. Neurobiol. 19: 173–224 (1976); A. V. Robertson and A. V. Juorio, J. Neurochem. 28: 573–79 (1977); J. A. Nathanson, Physiological Reviews 57: 158–256 (1977)).

Analogous to the action of NE and EPI in vertebrates, many of the effects of OA in invertebrates are mediated by cyclic AMP (J. A. Nathanson and P. Greengard, Science 19: 308–310 (1973); J. A. Nathanson, Physiological Reviews 57: 158–256 (1977); H. Robertson and J. Steele, J. Neurochem 19: 1603–06 (1972); A. Harmar and A. Horn, Mol. Pharmacol. 13: 512–20 (1976); C. Lingle et al., Handbook of Exptl. Pharmacology, (J. Kebabian & J. Nathanson, eds.), pp. 787–846 (1982)). OA stimulates production of cyclic AMP through activation of OA-sensitive (G, protein-coupled) adenylate cyclase (J. A. Nathanson, J. Cyclic Nucleotide and Protein Phosphor. Res. 10: 157–66 (1985)). In 1979, it was found that the firefly light organ, in which OA mediates neural control of light emission (A. D. Carlson, Advances Insect Physiol. 6: 51–96 (1969); J. F. Case and L. G. Strause, Bioluminescence in Action (P. J. Herring, ed.), pp. 331–366 (1978)), has a virtually pure population of OA receptors present in enormous quantity, with no evidence of adenylate cyclases activated by other hormones (J. A. Nathanson, Science 203: 65–8 (1979); J. A. Nathanson and E. Hunnicutt, J. Exp. Zool. 208: 255–62 (1979a)). Thereafter, the first detailed pharmacological characterization of $G_s$-linked OA receptors was carried out in the absence of other amine receptors (J. A. Nathanson, Science 203: 65–8 (1979); J. A. Nathanson and E. Hunnicutt, J. Exp. Zool. 208: 255–62 (1979a); J. A. Nathanson, Proc. Natl. Acad. Sci. U.S.A. 82: 599–603 (1985b); Nathanson, J. A., in Insect Neurochemistry and Neurophysiology, Borkovec, A., et al., eds., Humana: Clifton, N.J., pp. 263–266 (1986); Nathanson, J. A., et al., Neurosci. Abstr. 5:346 (1979)). More recently, a new chemical class of potent OA receptor agonists has been characterized, the phenyliminoimidazolidines (PIIs) (Nathanson, J. A., Proc. Natl. Acad. Sci. U.S.A. 82: 599–603 (1985); Nathanson, J. A., Mol. Pharmacol. 28: 254–268 (1985)). With the PIIs and other compounds, it has been possible to distinguish clearly the characteristics of OA receptors from those of mammalian adrenergic, dopaminergic, and serotonergic receptors.

Overactivation of the OA system in insects and acarines leads to behavioral and physiological abnormalities that have pestistatic and pesticidal consequences. One way to cause OA overactivation, and thereby take advantage of this system for pesticide development, is to directly stimulate OA receptor proteins.

Analogous to the octopamine neurotransmitter system is the cholinergic system, where the plant alkaloid nicotine exerts natural pesticidal effects through excessive activation of acetylcholine (ACh) receptors. As is well known, for pesticide development it has turned out that, more effective than cholinergic agonists, are the reversible and irreversible acetylcholinesterase inhibitors. Acetylcholinesterase (AChE) catalyzes the hydrolysis of the neurotransmitter ACh to choline and acetate. If AChE is inhibited by a pesticide, normal inactivation of ACh is blocked, and ACh accumulates to abnormally high levels. This causes overactivation of ACh receptors, indirectly, through inhibition of neurotransmitter degradation. It has recently been discovered that an analogous site of action exists for the OA system. Because of OA's selectivity for invertebrates, agents affecting this site will have reduced toxicity for vertebrates.

Because OA affects so many sites in insects, it is not surprising that disruption of this system adversely affects insect physiology. In 1980, it was reported that the formamidine pesticides cause glowing of firefly light organs and it was suggested that these compounds, which have low toxicity for vertebrates, might be exerting their pesticidal actions by affecting OA receptors. Subsequently, several labs (Nathanson, J. A., et al., Molec. Pharmacol. 20: 68–75 (1981); Evans, P. D., et al., Nature 287: 60–62 (1980)), determined that the formamidines are indeed potent OA agonists in several insect species. In addition, it was found that OA itself, as well as OA analogs and the PIIs applied to leaves, could markedly interfere with the feeding of *M. sexta* (Nathanson, J. A., Proc. Natl. Acad. Sci. U.S.A. 82: 599–603 (1985); Nathanson, J. A., in Insect Neurochemistry and Neurophysiology, Borkovec, A., et al., eds., Humana: Clifton. N.J., pp. 263–266 (1986); Nathanson, J. A., Mol. Pharmacol. 28: 254–268 (1985); Nathanson, J. A., in Sites of Action for Neurotoxic Pesticides, Hollingworth. R., et al., eds., Am. Chem. Soc.: Washington, D.C., pp. 154–161 (1987): Nathanson, J. A., Science 226: 184–187 (1984); Nathanson, J. A., in Abstr. 2nd Internatl. Symp. Insect Neurobiol. Pest. Action, Society of Chemical Industry: London, pp. 129–130 (1985); Nathanson, J. A., in Membrane Receptors and Enzyme as Targets of Insecticidal Action, Clark, J., et al., Plenum: New York, pp. 157–171 (1986)). The behavioral and pestistatic effects of these compounds on Manduca were similar to those of the formamidines: they caused tremors, hyperactivity, rearing, and poor coordination (resulting in leaf drop-off), abnormalities which, interestingly, are reminiscent of the effects of overdoses of amphetamines and adrenergic agonists in vertebrates.

Additional support for a connection between overactivation of the OA system and pesticidal activity has come from observations showing that the known species variation in the pesticidal effects of formamidines (Matsumura, F., et al., Environ. Health Perspect. 14: 71–82 (1976)) is related to the ability of these compounds to activate $G_s$-coupled OA receptors ($G_s$-coupled receptors are those whose activation results in the stimulation of adenylate cyclase and the synthesis of cyclic AMP). For example, in Manduca, a sensitive species, it has been found (Nathanson, J. A., Mol. Pharmacol. 28: 254–268 (1985)) that didemethylchlordimeform (DDCDM) is a full OA agonist, 20-fold more potent than OA, while in cockroach, a resistant species, DDCDM is much weaker than OA in activating adenylate cyclase. This species variability appears to result from the distribution of OA receptor subtypes that need to be specifically targeted for pesticide activity. (Additional evidence for involvement of $G_s$ (cAMP-linked) OA receptors comes from the observations (Nathanson, J. A., Proc. Natl. Acad. Sci. U.S.A. 82: 599–603 (1985) that the antifeeding effects of OA agonists are enhanced by inhibitors of cAMP catabolism and mimicked by adenylate cyclase activators (forskolin) and lipid-soluble cAMP analogs.)

In insects, uptake studies of monoamines have been largely limited to the study of octopamine, where evidence from intact tissue experiments supports the presence of a high affinity sodium-dependent transporter (Evans, J. Neurochem 30: 1015–1022 (1978); Carlson and Evans, J. Exp. Biol. 122: 369–385 (1986); Wierenga and Hollingworth, J. Neurochem. 54: 479–489 (1990)). These studies have utilized either intact ventral nerve cord or intact pieces of tissue incubated in insect saline. Surprisingly, there appears to be no report of the examination of the uptake of octopamine or other monoamines in synaptosomal-containing broken cell fractions. This appears to be the case despite the fact that several reports have described preparations of both crude and purified synaptosomal fractions from insects (Breer and Jererich, Insect Biochem. 10: 457–463 (1980); Whitton et al., Biochem. Soc. Trans. 14: 609–610 (1986); Luo and Bodnaryk, Insect Biochem. 17: 911–918 (1987); Nicholson and Connelly, Insect Biochem. 21: 447–456 (1991)).

SUMMARY OF THE INVENTION

The invention relates to a class of compounds which block the invertebrate octopamine reuptake transporter, resulting in pestistatic and pesticidal effects.

The invention is directed to a method of controlling an invertebrate pest, comprising contacting the pest with a pest-controlling amount of an agent having substantial inhibitory activity toward a phenylethanolamine reuptake transporter, as determined by radioactive octopamine reuptake inhibition assay.

Reuptake is substantially inhibited when the agent is present at a concentration of from about $10^{-12}$ molar (M) to about $10^{-3}$M, or from about $10^{-12}$M to about $10^{-2}$M, and reuptake of a phenylethanolamine, e.g., octopamine, is inhibited from about 25 to about 100 percent as compared to reuptake by a control.

The invention is directed to a method of controlling an invertebrate pest wherein the agent is a cocaine derivative and has the formula:

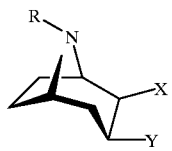

wherein R is H, $CH_3(CH_2)_n$, which may be branched or unbranched, and wherein n=0–10, $C_6H_5(CH_2)_m$, wherein m=0–10, and X=

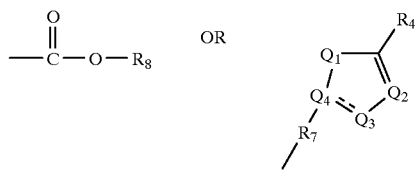

wherein $Q_1$, $Q_2$, $Q_3$ and $Q_4$ are the same or different and may be C, S, N or O, with the proviso that at least one of $Q_1$, $Q_2$, $Q_3$ and Q4 are N;

$R_4$ is hydrogen; methyl; phenyl optionally substituted with halogen, methoxy or $C_{1-6}$ alkyl; cyclopropyl or $C_{1-6}$ alkyl;

- - - - is a single or double bond; and $R_7$ is a single bond, H—C=O or $CH_2$;

$R_8$ is phenyl, $C_{1-6}$ alkyl, $C_{1-6}$ alkyl-substituted phenyl;

or $Q_2$ and $R_4$ form a phenyl ring;

or X=

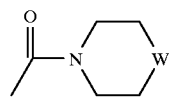

wherein W=$(CH_2)_n$, wherein n=0–4 or O, or X=

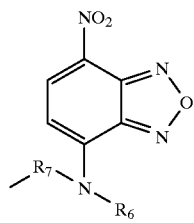

wherein $R_6$ is hydrogen, methyl, amino or nitro;

$R_7$ is methylene, $—CO_2—CH_2—CH_2—$, $—CO_2CH_2CH_2C_6H_5—$ or $—CH_2—NCH_2—CO—CH_2—NH—CO—R_{16}—$ and $R_{16}$ is $—CH_2—CH_2—$, $CH_2NH—CO—CH_2—$ or $CH_2—NH—CO—CH_2—NH—CO—CH_2—$ or X=

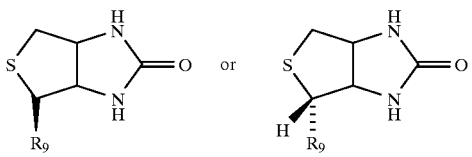

wherein $R_9$ is $—CH_2NHCO—CH_2CH_2CH_2CH_2—$, $—CH_2—NCH_2—CO—CH_2CH_2CH_2CH_2$ or $—CO—O—CH_2—CH_2C_6H_5—NH—CO—CH_2—CH_2—CH_2—CH_2—$ and Y=

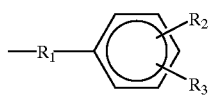

wherein
R₁ is a single bond, S, —O—CO— and
R₂ and R₃ are hydrogen, halogen, CN, CF₃, NO₂, N₃, OR, CONH₂, CO₂R, C₁₋₆ alkyl, NR₁₀R₁₁, NHCOR₁₁, NHCO₂R₁₂,

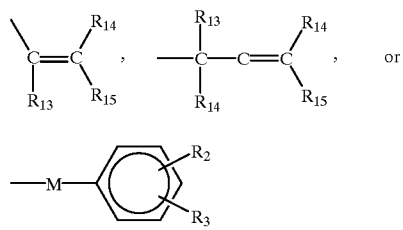

wherein R₁₃, R₁₄ and R₁₅ are H or C₁₋₆ alkyl and M=(CH₂)ₓ wherein x=1–8, —CH=CH—, or —C≡C—, C₁₋₆ alkyl, C₃₋₈ cycloalkyl, C₁₋₄ alkoxy, C₁₋₆ alkynyl, amino, acylamido or Sn(CH₃)₃ wherein R₁, R₁₁ and R₁₂ are C₁₋₆ alkyl.

The invention is also directed to a pest-controlling compound which comprises an agent having substantial inhibitory activity toward a phenylethanolamine reuptake transporter as determined by radioactive octopamine reuptake inhibition assay. Reuptake is substantially inhibited when the agent is present at a concentration of from about $10^{-12}$M to about $10^{-3}$M, or from about $10^{-12}$M to about $10^{-2}$M, and inhibition of reuptake of a phenylethanolamine, e.g., octopamine, is from about 25 to about 100 percent as compared to reuptake by the control.

The invention is also directed to a pesticidal composition comprising a reuptake inhibiting agent in the form of a powder, a water dispersion, an emulsion, or a dispersion, formulated together with a pesticidally inert carrier.

The invention is also directed to a synergistic pest-controlling composition which comprises: a pest-controlling amount of an agent having substantial inhibitory activity toward a phenylethanolamine reuptake transporter as determined by radioactive reuptake inhibition assay; and a pest-controlling amount of a phenylethanolamine or other agonists of octopamine receptors. The phenylethanolamine may be octopamine.

The invention is also directed to a process for inhibiting the feeding of an invertebrate pest comprising conducting said pest with a pest-controlling amount an agent having substantial inhibitory activity toward a phenylethanolamine reuptake transporter as determined by radioactive octopamine reuptake inhibition assay, with the proviso that said agent is not cocaine.

The invention is also directed to a process for delaying the maturation of a juvenile invertebrate by contacting it with a pest-controlling amount of an agent having substantial inhibitory activity toward a phenylethanolamine reuptake transporter as determined by radioactive octopamine reuptake inhibition assay, with the proviso that said agent is not cocaine.

The invention is also directed to a radioactive octopamine reuptake inhibition assay for determining whether a given compound is an inhibitor of octopamine neuronal transport. This in vitro assay measures the uptake of radioactive phenylethanolamine into membrane (broken cell) preparations, or more preferably, into intact tissue or synaptosomal preparations, derived from insect or other invertebrate nerve tissue.

The phenylethanolamine reuptake inhibitors of the invention are highly selective pest control agents since vertebrate species-as opposed to invertebrate, e.g., insect, species-lack phenylethanolamine reuptake transporters selective for octopamine. In addition, these phenylethanolamine reuptake inhibitors unexpectedly have synergistic activity when combined with other phenylethanolamine octopamine agonists, particularly the phenylethanolamine octopamine, as an antifeeding composition.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
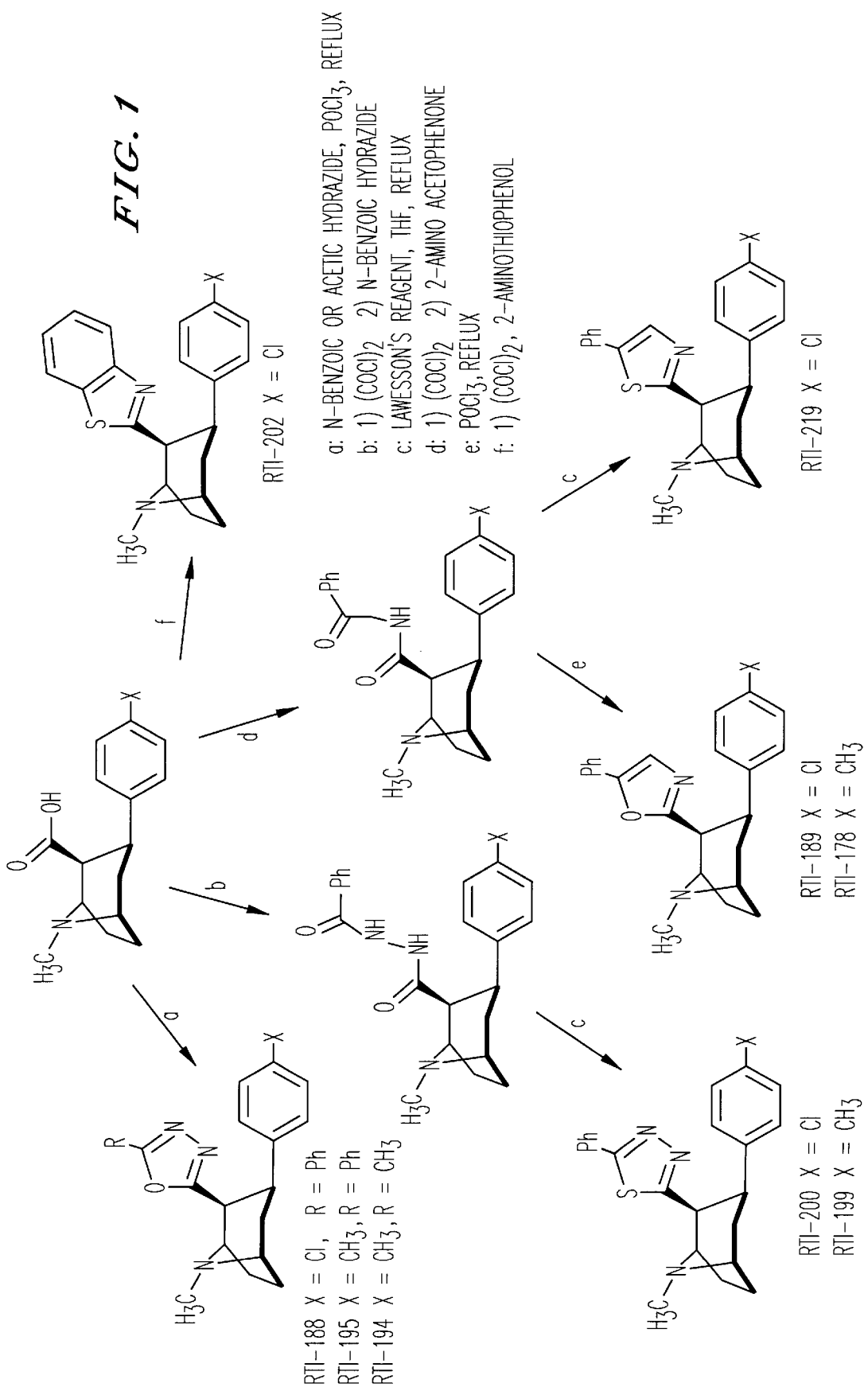
FIG. 1 depicts the scheme for converting 3-(substituted phenyl)-2-tropane carboxylic acid (tropane acid) to 2substituted oxazoles, oxadiazoles, thiazoles, thiadiazoles and benzothiazole.

The present invention utilizes novel compounds having the following formula:

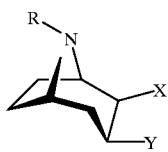

wherein R is H, $CH_3(CH_2)_n$, which may be branched or unbranched, and wherein n=0–10, $C_6H_5(CH_2)_m$, wherein m=0–10,
and X=

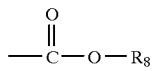 OR 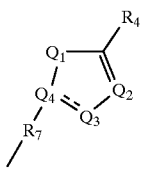

wherein $Q_1$, $Q_2$, $Q_3$ and $Q_4$ are the same or different and may be C, S, N or O, with the proviso that at least one of $Q_1$, $Q_2$, $Q_3$ and $Q_4$ are N;

$R_4$ is hydrogen; methyl; phenyl optionally substituted with halogen, methoxy or $C_{1-6}$ alkyl; cyclopropyl or $C_{1-6}$ alkyl;

- - - - is a single or double bond; and $R_7$ is a single bond, H—C=O or $CH_2$;

$R_8$ is phenyl, $C_{1-6}$ alkyl, $C_{1-6}$ alkyl-substituted phenyl; or $Q_2$ and $R_4$ form a phenyl ring;
or X=

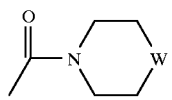

wherein W=$(CH_2)_n$ wherein n=0–4 or O,
or X=

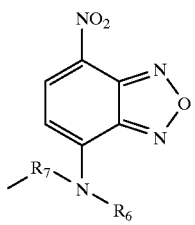

wherein $R_6$ is hydrogen, methyl, amino or nitro;

$R_7$ is methylene, $-CO_2-CH_2-CH_2-$, $-CO_2CH_2CH_2C_6H_5-$ or $-CH_2-NCH_2-CO-CH_2-NH-CO-R_{16}-$ and $R_{16}$ is $-CH_2-CH_2-$, $CH_2NH-CO-CH_2-$ or $CH_2-NH-CO-CH_2-NH-CO-CH_2-$ or X=

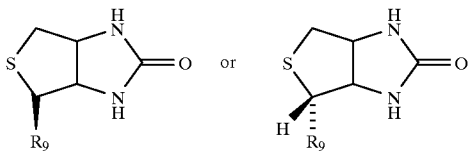

wherein $R_9$ is $-CH_2NHCO-CH_2CH_2CH_2CH_2-$, $-CH_2-NCH_2-CO-CH_2CH_2CH_2CH_2$ or $-CO-O-CH_2-CH_2C_6H_5-NH-CO-CH_2-CH_2-CH_2-CH_2-$ and Y=

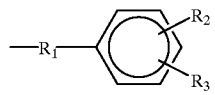

wherein $R_1$ is a single bond, S, $-O-CO-$ and $R_2$ and $R_3$ are hydrogen, halogen, CN, $CF_3$, $NO_2$, $N_3$, OR, $CONH_2$, $CO_2R$, $C_{1-6}$ alkyl, $NR^{10}R_{11}$, $NHCOR_{11}$, $NHCO_2R_{12}$,

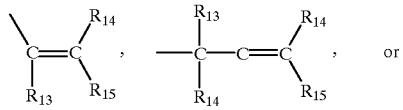

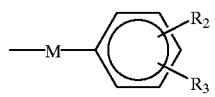

wherein $R_{13}$, $R_{14}$ and $R_{15}$ are H or $C_{1-6}$ alkyl and M=$(CH_2)_x$ wherein x=1–8, $-CH=CH-$, or $-C\equiv C-$, $C_{1-6}$ alkyl, $C_{3-8}$ cycloalkyl, $C_{1-4}$ alkoxy, $C_{1-6}$ alkynyl, amino, acylamido or $Sn(CH_3)_3$ wherein $R_1$, $R_{11}$ and $R_{12}$ are $C_{1-6}$ alkyl.

Preferred compounds for use in accordance with the present invention include the following:

TABLE I
RTI-4229-87
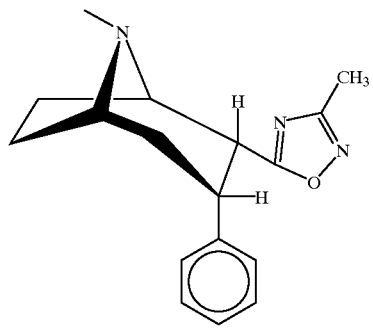
RTI-4229-119
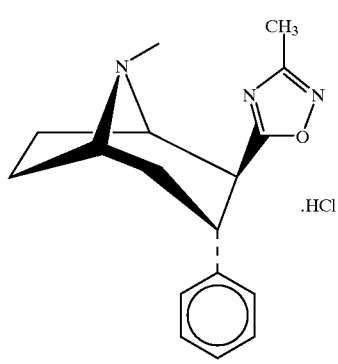
.HCl
RTI-4229-124
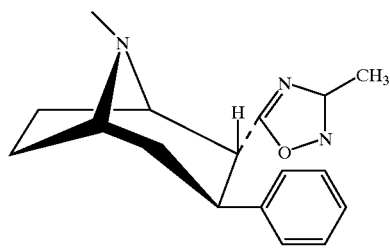
RTI-4229-125
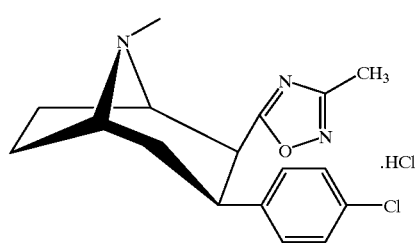
.HCl
RTI-4229-126
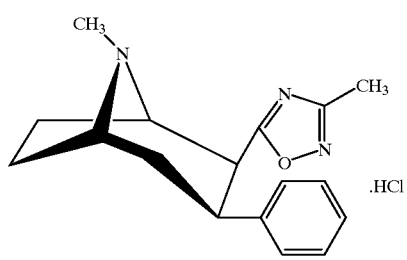
.HCl TABLE I-continued
RTI-4229-130 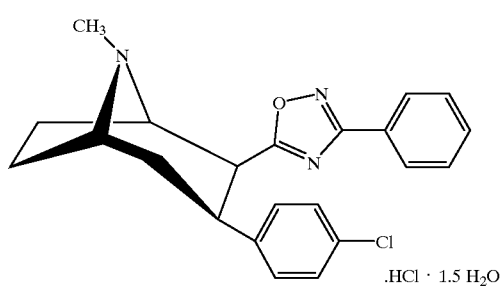
.HCl · 1.5 H₂O
RTI-4229-141 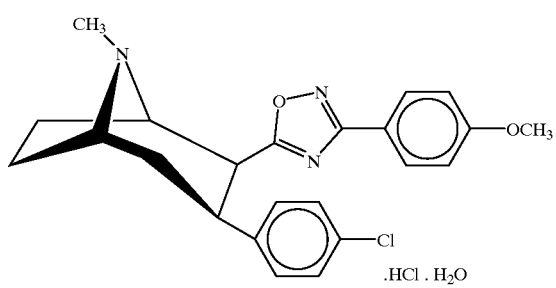
.HCl . H₂O
RTI-4229-143 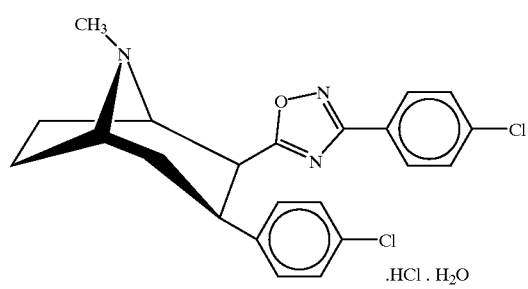
.HCl . H₂O
RTI-4229-144 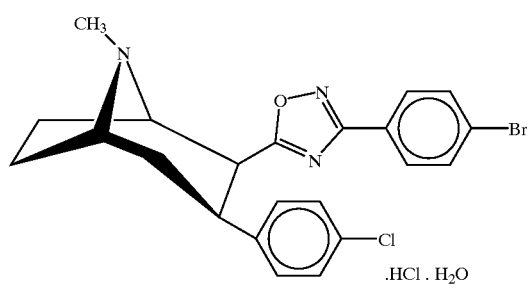
.HCl . H₂O
RTI-4229-147 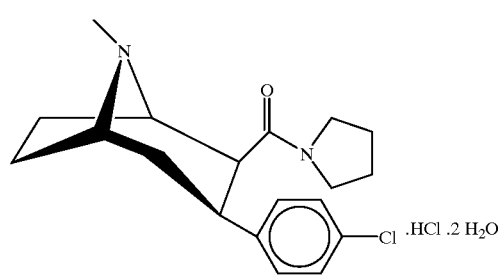
.HCl .2 H₂O TABLE I-continued
RTI-4229-151 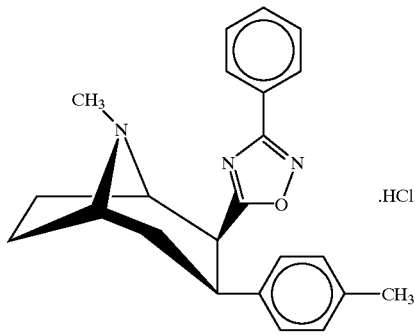 .HCl
RTI-4229-152 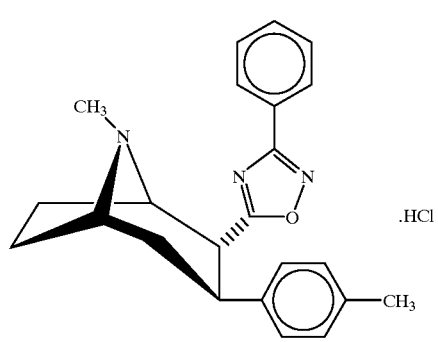 .HCl
RTI-4220-154 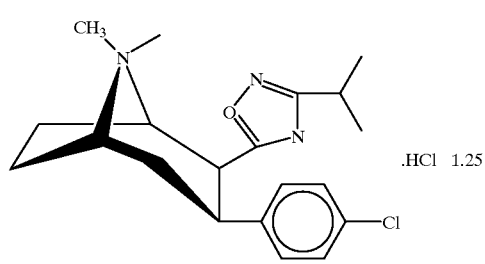 .HCl 1.25
RTI-4229-155 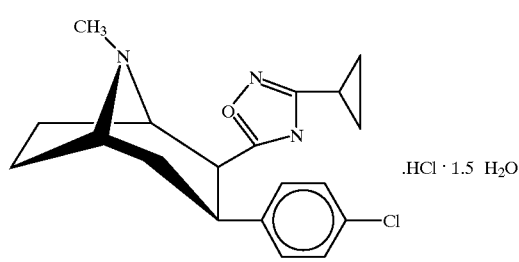 .HCl · 1.5 H₂O
RTI-4229-156 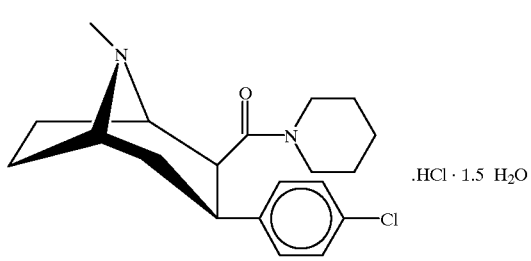 .HCl · 1.5 H₂O TABLE I-continued
RTI-4229-157 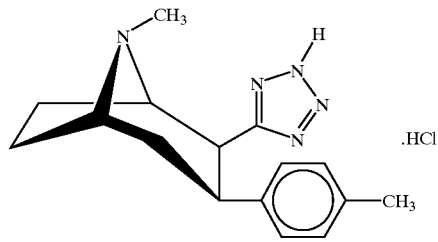 .HCl
RTI-4229-163 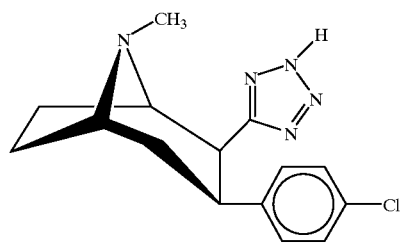
RTI-4229-165 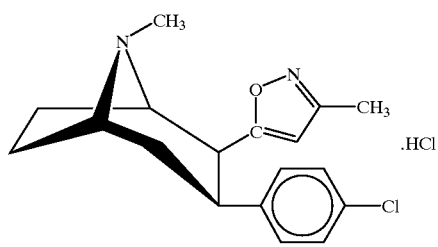 .HCl
RTI-4229-171 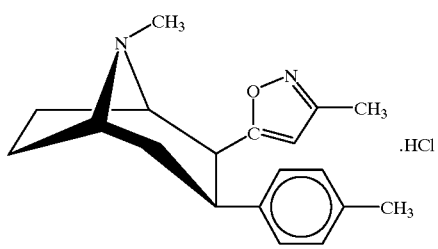 .HCl
RTI-4229-176 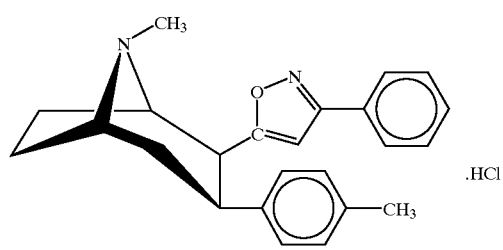 .HCl
RTI-4229-177 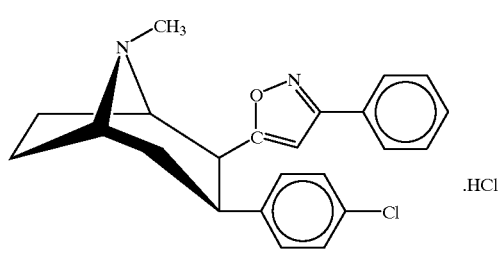 .HCl TABLE I-continued
RTI-4229-178 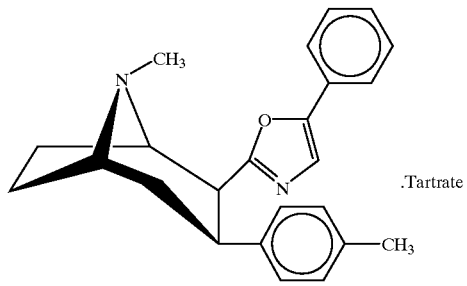 .Tartrate
RTI-4229-180 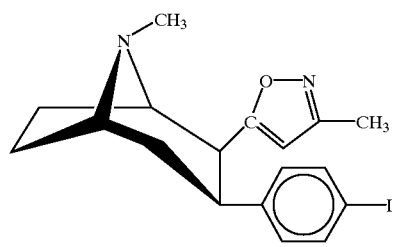
RTI-4229-181 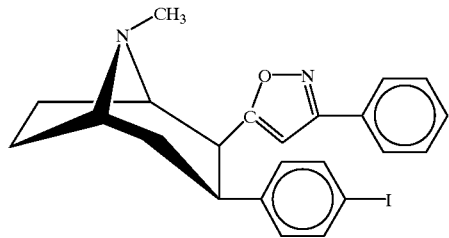
RTI-4229-184 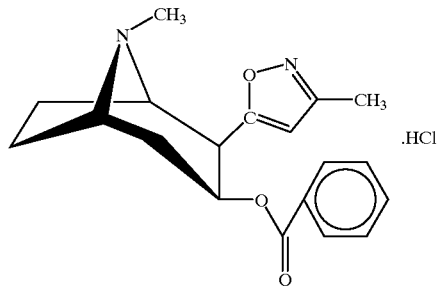 .HCl
RTI-4229-185 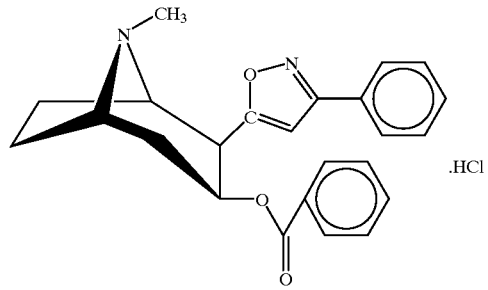 .HCl TABLE I-continued
RTI-4229-188
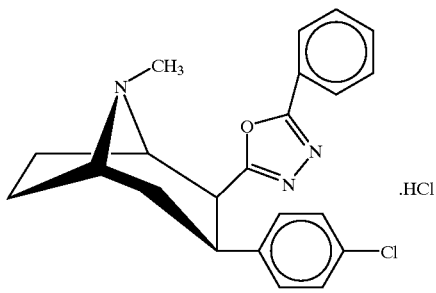
.HCl
RTI-4229-189
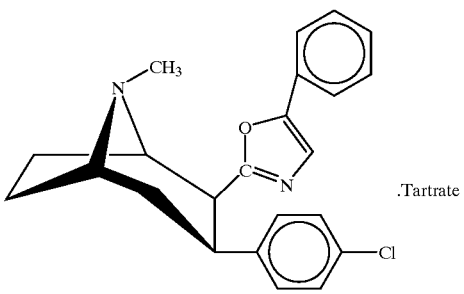
.Tartrate
RTI-4229-194
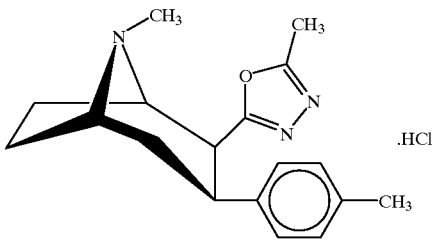
.HCl
RTI-4229-195
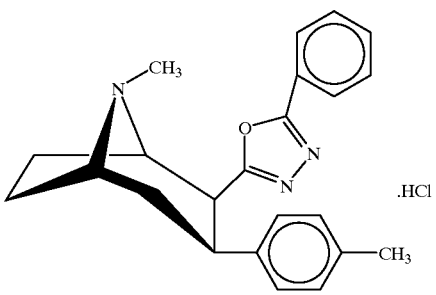
.HCl
RTI-4229-199
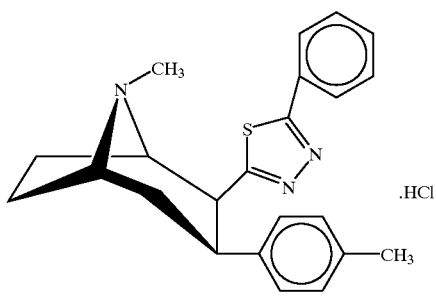
.HCl TABLE I-continued
RTI-4229-200
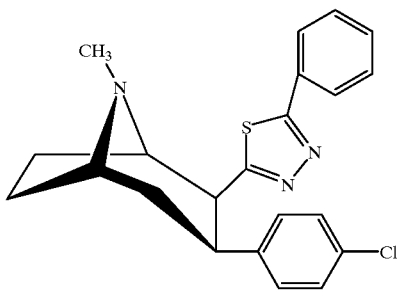
RTI-4229-202
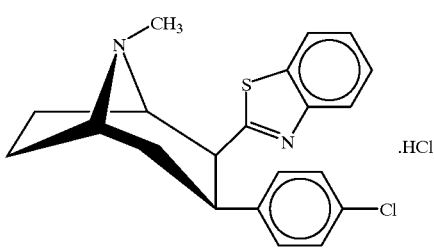
.HCl
RTI-4229-208
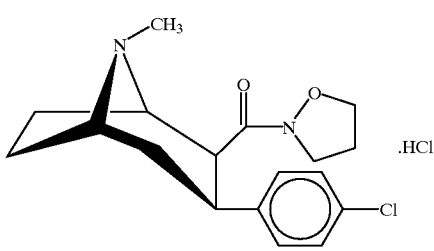
.HCl
RTI-4229-214
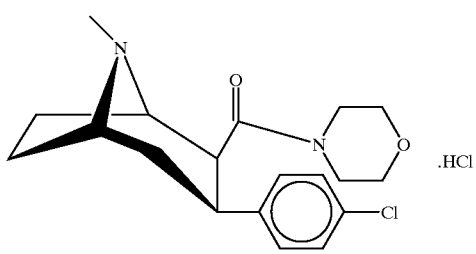
.HCl
RTI-4229-219
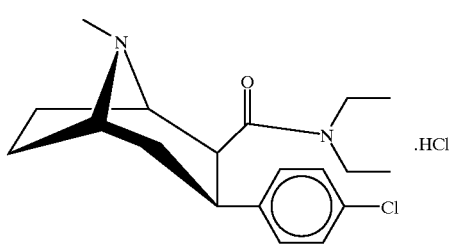
.HCl
RTI-4229-220
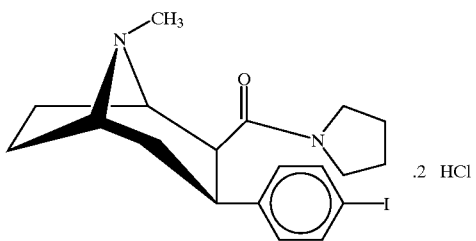
.2 HCl TABLE I-continued
RTI-4229-222
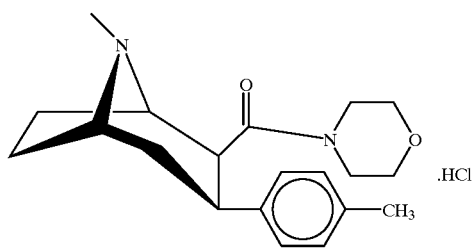
.HCl
RTI-4229-224
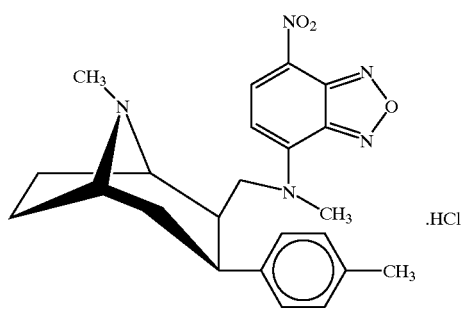
.HCl
RTI-4229-227
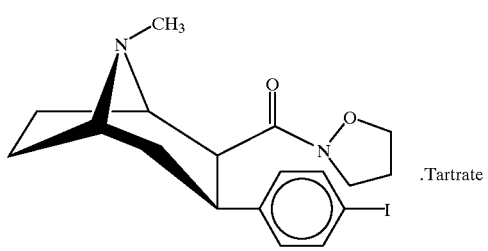
.Tartrate
RTI-4229-229
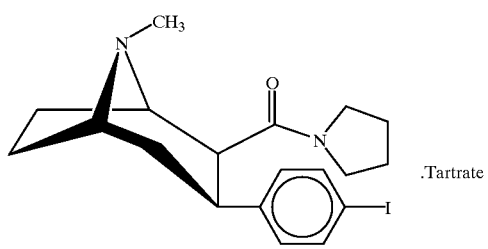
.Tartrate
RTI-4229-233
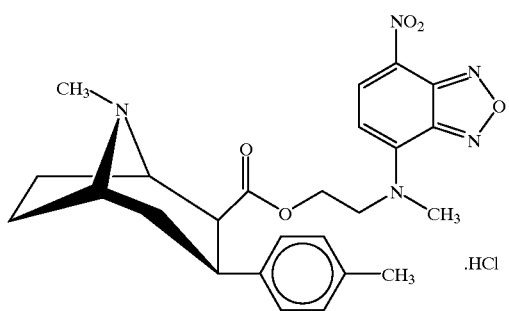
.HCl TABLE I-continued
RTI-4229-235
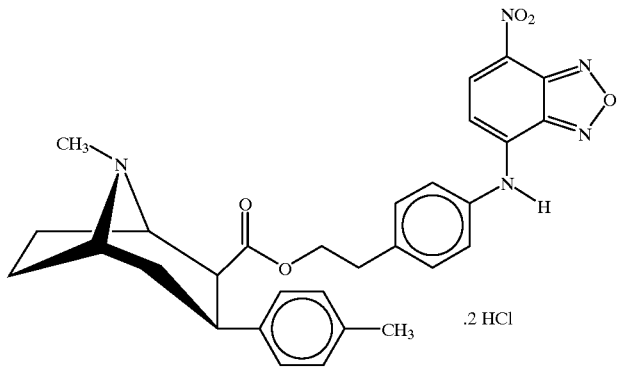
RTI-4229-236
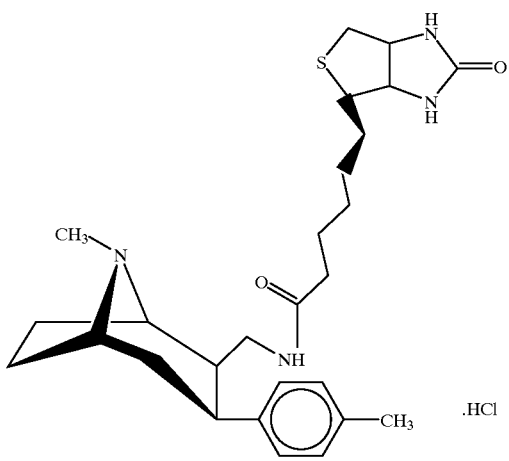
RTI-4229-237
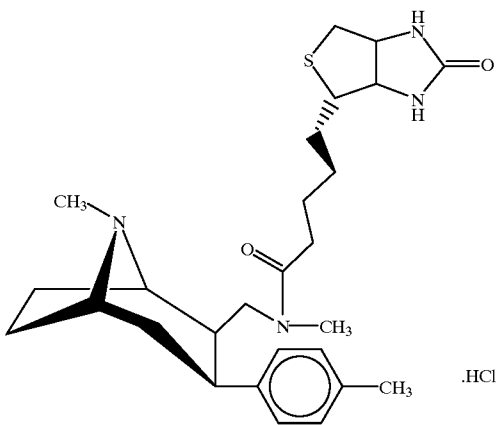
RTI-4229-244
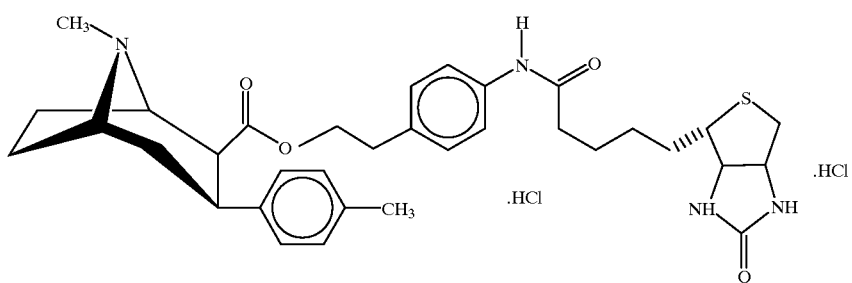

TABLE I-continued
RTI-4229-245
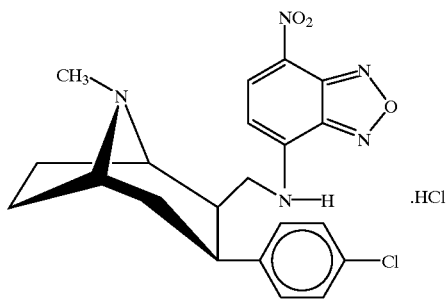
RTI-4229-246
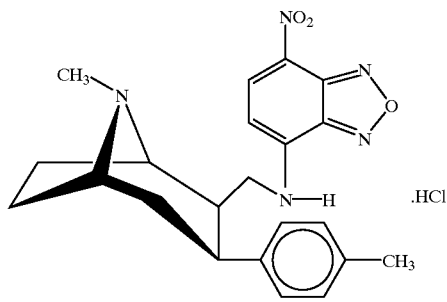
RTI-4229-248
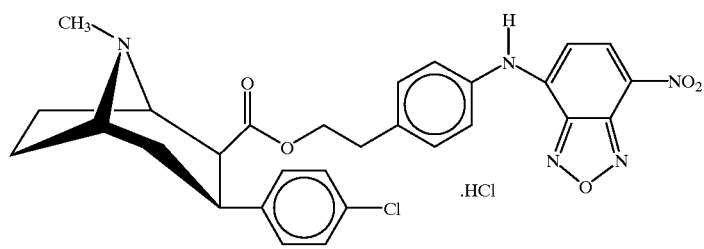
RTI-4229-249
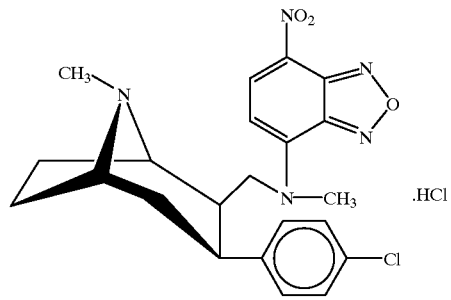
RTI-4229-250
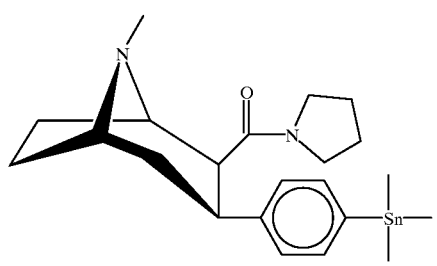

TABLE I-continued
RTI-4229-253 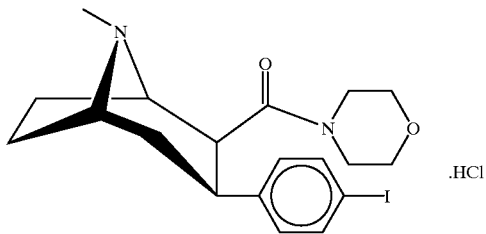 .HCl
RTI-4229-262 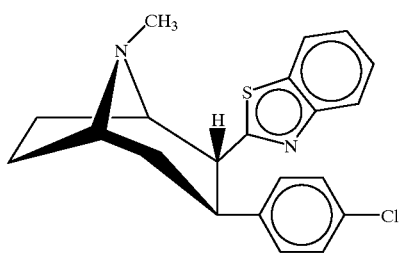
RTI-4229-263 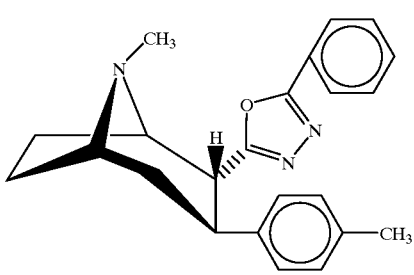
RTI-4229-264 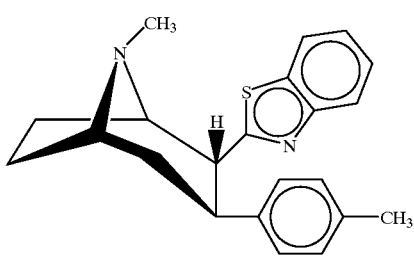
RTI-4229-265 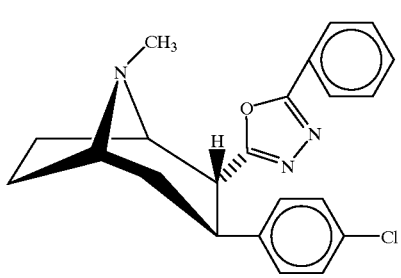

TABLE I-continued
RTI-4229-266
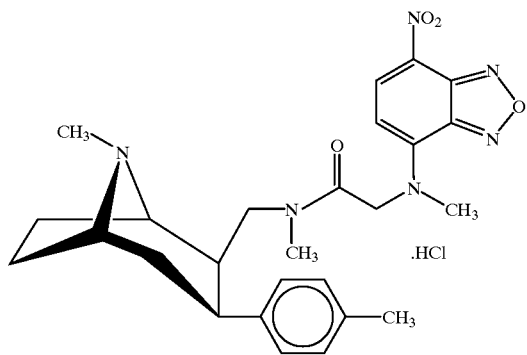
RTI-4229-267
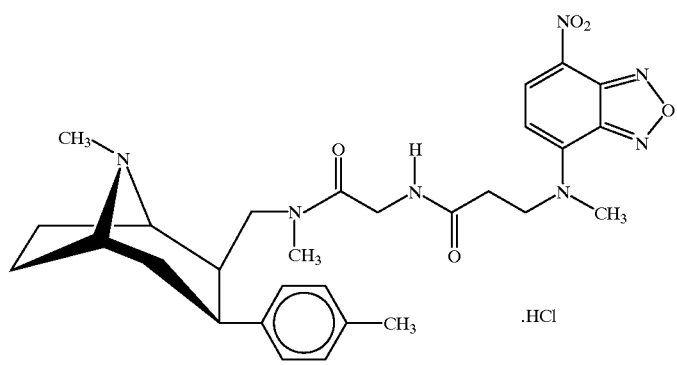
RTI-4229-268
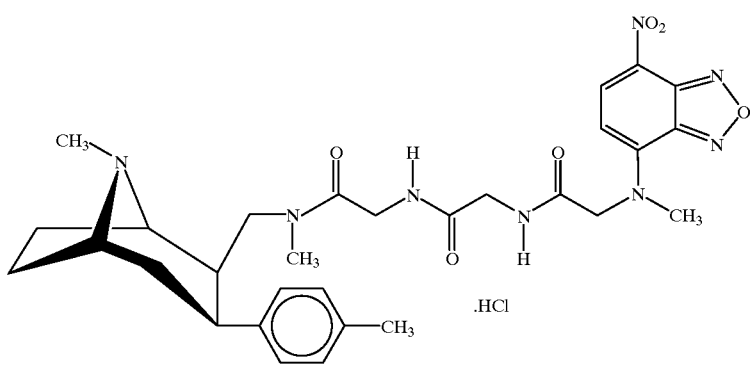
RTI-4229-269
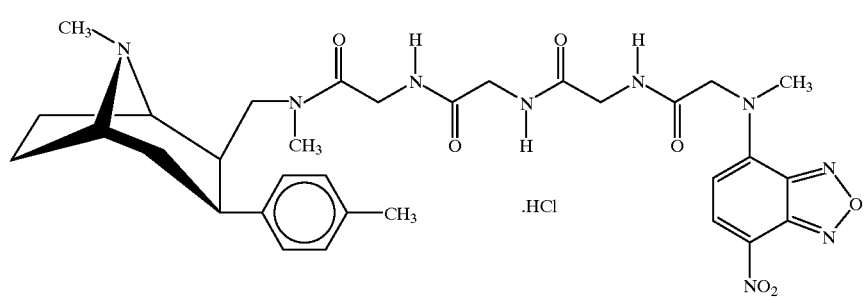

TABLE I-continued
RTI-4229-334 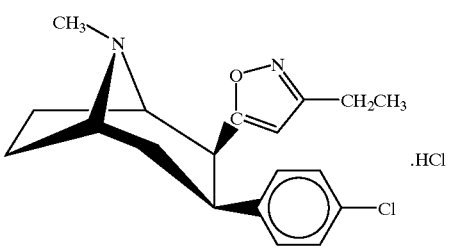
.HCl
RTI-4229-335 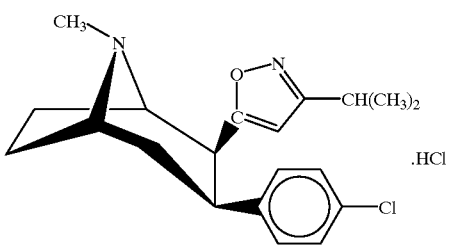
.HCl
RTI-4229-336 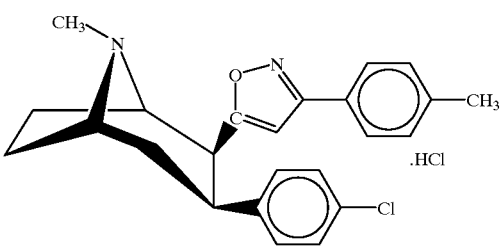
.HCl
RTI-4229-337 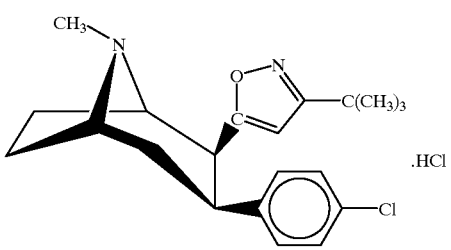
.HCl
RTI-4229-345 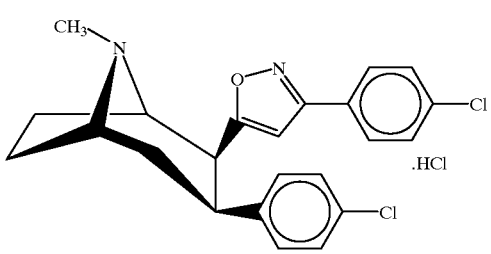
.HCl
RTI-4229-346 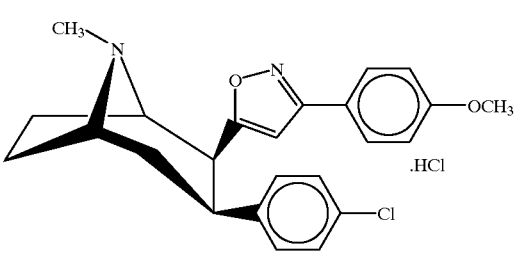
.HCl TABLE I-continued
RTI-4229-347 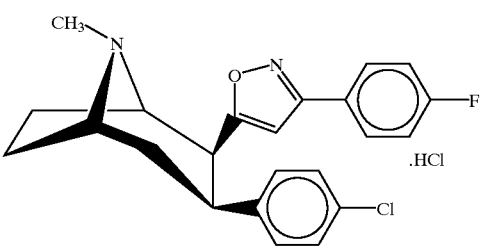 .HCl
RTI-4229-354 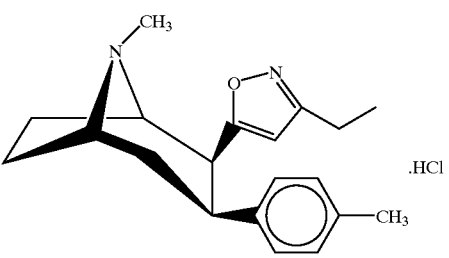 .HCl
RTI-4229-333 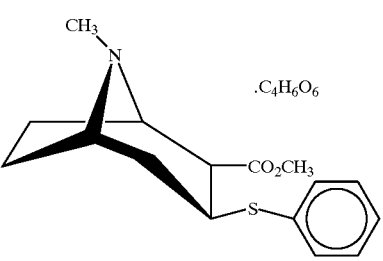 .C$_4$H$_6$O$_6$
RTI-4229-339 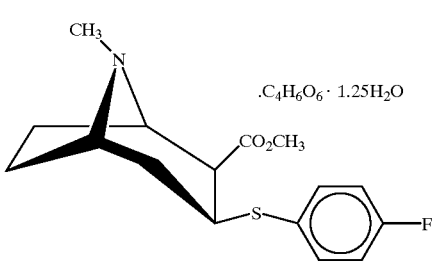 .C$_4$H$_6$O$_6$ · 1.25H$_2$O
RTI-4229-340 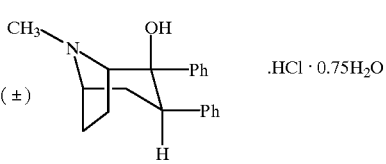 .HCl · 0.75H$_2$O
RTI-4229-343 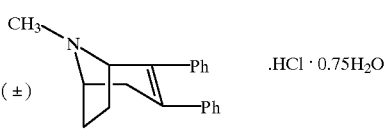 .HCl · 0.75H$_2$O
RTI-4229-348 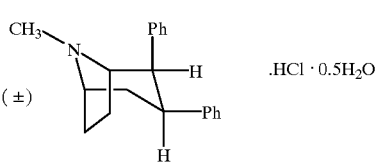 .HCl · 0.5H$_2$O TABLE I-continued

RTI-4229-350

[structure: bicyclic amine with N-CH₃, phenyl with Cl, and Ph substituents, (±)] .HCl · 0.5H₂O

RTI-4229-351

[structure: bicyclic amine with N-CH₃, two Ph substituents with H stereochemistry, (±)] .HCl · 0.5H₂O

---

By the term "phenylethanolamine reuptake inhibitor" is intended compounds which block the reuptake of a catacholomius, indoleamius or phenylethanolamine compound by a phenylethanolamine reuptake protein.

Cocaine is a natural alkaloid derived from the leaves of the Erythroxylon species of coca plants. The extraction procedure is reported in Squibb, Pharm. J. 15[3]:775, 796; Squibb, Pharm. J. 6: 67–69 (1885). Synthesis of cocaine is reported in Willstatter et al., Ann. der Chemie 434: 111–139 (1923). Derivatives of cocaine include, but are not limited to, cocaethylene (ecgonine ethyl ester benzoate), ecgonine hydrochloride ((−)-beta-hydroxy-1-alpha -H,5-alpha-H-tropane-2-beta-carboxylic acid hydrochloride) and ecgonidine methyl ester mesylate ((1R)-8-methyl-8-azabicyclo[3,2,1]oct-2-ene2-carboxylic acid methyl ester mesylate). Synthesis of cocaethylene is reported in Merck, Ber. 18, 2952 (1885); Einhorn, ibid. 21, 47 (1888). Synthesis of ecgonine hydrochloride may be obtained via the hydrolysis of cocaine (Willsatter et al., Ann. der Chemie. 434: 111–139 (1923); Bell, Archer, J. Am. Chem. Soc. 82: 4642–44 (1960)). The production of methylecgonine resulting from the pyrolysis and volatilization of cocaine is reported by Martin et al., J. Ana. Toxicol. 13(3): 158–162 (1989).

Another class of phenylethanolamine re-uptake inhibitors include, but are not limited to, the tricyclic antidepressants exemplified by desipramine, imipramine, amoxapine, nortriptyline, protriptyline, maprotiline, doxepin, and pharmaceutically acceptable salts thereof. Methods of preparation of desipramine hydrochloride are described in Belgian Patent No. 614,616 (C. A. 58:11338C (1963)). Preparation of the free base anhydrochloride is disclosed in British Patent No. 908,788 (1962). The preparation of amoxapine, a known anti-depressant, is reported by Schmultz, J., et al., Helv. Chim. Acta 15:245 (1967). The preparation of nortriptyline, another known anti-depressant, is reported by Hoffsommer et al., J. Org. Chem. 27: 4134–37 (1962). A comprehensive description of nortriptyline is provided by Hale, J. L., in Analytical Profiles of Drug Substances, Vol. 1, K. Florey, Ed. (Academic Press, New York, 1972), pp. 233–247. The synthesis of the anti-depressant protriptyline is described in U.S. Pat. Nos. 3,244,748 and 3,271,451, and in Belgian Patent No. 617,967. Preparation of the anti-depressant maprotiline is reported in Swiss Patent Nos. 467,237 and 467,747, and in Wilhelm et al., Helv. Chim. Acta 52: 1385–95 (1969). Preparation of imipramine hydrochloride is reported in U.S. Pat. No. 2,554,736 and in Remington's Pharmaceutical Sciences, Osol, R., Ed., Mack Publishing Co., Easton, Pa., p. 1040 (1980). The preparation of doxepin is reported in Stach et al., Monatsc. 93: 896–904 (1962), and Bickelhaupt et al., ibid. 95:485 (1964), and in U.S. Pat. No. 3,438,981 (1969). The preparation of trimipramine is reported by Jacob Messer, Compt. Rend. 252:2117 (1961).

The preparation of the atypical antidepressant fluoxetine, which also has demonstrated activity as a phenylethanolamine reuptake transporter inhibitor, is reported by Malloy, B. B., Schmiegel, K. K., German Patent No. 2,500,110; Eidem, U.S. Pat. No. 4,314,081.

The terms "pest controlling amount" or "controlling an invertebrate pest," used throughout the specification and claims, are meant to include any pesticidal (killing) or pestistatic (preventing the host plant from being eaten, or inhibiting, maiming or generally interfering) activities of a composition against a given pest at any stage in its life cycle. Thus, these terms not only include killing, but also include the production of behavioral abnormalities (e.g., tremor, incoordination, hyperactivity, anorexia, leaf walk-off behavior) which interfere with activities such as, but not limited to, eating, molting, hatching, mobility or plant attachment. The terms also include chemosterilant activity which produces sterility in insects by preventing the production of ova or sperm, by causing death of sperm or ova, or by producing severe injury to the genetic material of sperm or ova, so that the larvae that are produced do not develop into mature progeny.

The terms also include repellant activity that protect animals, plants or products from insect attack by making food or living conditions unattractive or offensive. These repellant activities may be the result of repellents which may be poisonous, mildly toxic, or non-poisonous.

The term "substantial inhibitory activity" describes agents identified through the radioactive octopamine reuptake inhibition assay, described below.

Essentially any chemical agent, present at a concentration of from about $10^{-12}$ molar (M) to $10^{-2}$ M, and demonstrating inhibition of from about 25 to about 100 percent as compared to the control, is considered a pest-controlling agent having a substantial inhibitory activity.

The term "radioactive octopamine reuptake inhibition assay" is meant to indicate the assay described herein more fully below. This assay is used to determine whether a given compound has any phenylethanolamine reuptake transporter-inhibiting activity. A compound that comes within this definition is one that decreases the uptake of radioactive octopamine when, over a range of concentrations from about $10^{-12}$ to about $10^{-2}$ moles per liter (M), there is a decrease of uptake from about 25 to about 100 per cent, relative to the control.

In particular, the invention relates to an in vitro method for determining whether a given compound is an inhibitor of octopamine neuronal transport. The assay is performed by contacting a neuronal invertebrate tissue sample with radiolabelled phenylethanolamine and the test compound, which may be present over a range of concentrations from about $10^{-12}$M to about $10^{-2}$M. After terminating contact with the radiolabelled phenylethanolamine, the tissue sample is then washed to remove free radiolabelled phenylethanolamine. The amount of radiolabelled phenylethanolamine bound or taken up by the tissue is then detected and compared with the amount of the label bound or taken up by tissue which had been contacted with radiolabelled phenylethanolamine in the absence of the compound. A relative decrease in the amount of label bound or taken up by the tissue in the presence of the compound indicates that the inhibition of octopamine neuronal transport has occurred. Preferably, the extent of decrease is at least about 25%.

The in vitro assay measures the uptake of radioactive phenylethanolamine into a tissue sample from an invertebrate pest. Preferably, the assay uses either intact tissue or a synaptosomal preparation from an invertebrate pest. The preferred invertebrate pests include, but are not limited to, *Periplaneta americana*, Blaberus, and *Manduca sexta*.

To measure uptake into intact tissue, nerve tissue is obtained from an invertebrate pest. The preferred nerve tissue is hemisected cerebral ganglia and thoracic ganglia. The isolated nerve tissue is pre-incubated at 24°–32° C. (preferably, 28° C.) for about 15 minutes in any saline solution compatible with neuronal invertebrate tissue. The preferred saline solution is a modified insect saline solution containing, e.g. 10 mM D-glucose; 130 mM NaCl; 8 mM KCl; 2 mM $CaCl_2$; 2 mM $MgCl_2$; 2.5 mM $K_2CO_3$; 2 mg/ml ascorbic acid; and 50 mM HEPES buffer.

In the preferred insect saline solution, the pH is adjusted with NaOH to about pH 7.2 (at 31° C.), which gives a final sodium concentration of about 155–160 mM and an osmolality of about 350–355. To measure sodium-dependent uptake, some ganglia are pre-incubated in a sodium-free saline solution in which sodium chloride is omitted and an equiosmolar amount of Tris buffer (17.6 g Tris HCl and 4.54 g Tris base per liter) added ("sodium-free saline solution"). Both sodium-containing and sodium-free saline solutions may also contain 1 μM pargyline HCl. After preincubation, uptake is measured in any suitable container, preferably, a multi-well tissue culture dish. In the preferred container, the tissue is placed in wells which contain just enough saline solution to barely cover the tissue pieces, thereby facilitating oxygenation under room atmospheric conditions. Some wells contain the compound to be assayed while others contain sodium-free saline solution. Radiolabelled octopamine or other phenylethanolamine described herein is present in all wells, preferably, at a final concentration of approximately 1 μM and 5 μCi/ml.

Following incubation for about 15 min at 24°–32° C. (preferably, 28° C.), tissue pieces are transferred to ice-cold saline solution (or sodium-free saline solution), gently agitated (preferably, for 30 sec), then transferred to a second ice-cold wash (preferably, for 30 sec), prior to final transfer to scintillation vials, where tissue is dissolved overnight, preferably, by incubating the tissue in 0.5 ml of 0.5N NaOH. After the tissue has dissolved, radioactivity is quantitated and sodium-dependent uptake is calculated on the basis of pmol amine/mg protein.

To measure uptake into synaptosomal preparations, the ganglia from the invertebrate pest of interest is rinsed briefly in a cold sucrose solution, preferably, 0.32M sucrose containing 15 mM Tris maleate pH 7.2. (A higher sucrose concentration (0.5–0.8M) may improve synaptosomal yield in some species.) The ganglia is then transferred in a sucrose solution, preferably, in 1 ml of sucrose/Tris (usually 50 mg tissue/ml) to a homogenizer. Preferably, the homogenizer is a 2 ml-sized Teflon-glass homogenizer with 0.25 mm clearance. Tissue is then gently homogenized on ice, preferably, at 200 rpm with 10 up and down strokes. The homogenate is transferred to a 12 ml conical plastic tissue-culture tube, 9 ml of cold sucrose solution added, and the mixture centrifuged, preferably, at 800×g for 10 min in the cold in a swinging bucket rotor.

After discarding the pellet, the supernatant is transferred to a tube and recentrifuged, preferably at 40,000×g for 30 min, in a fixed angle rotor. The resulting pellet: is resuspended by gentle trituration in the sucrose solution, preferably at 50 mg original wet weight/ml, transferred to the original homogenizer, and gently rehomogenized, by hand, to a uniform suspension. This synaptosomal fraction (a 10× stock concentration for most studies) is then stored on ice until use in uptake studies.

Uptake may be measured in any suitable container, preferably, 14×89 mm clear, thin-walled, high speed plastic centrifugation tubes. An aliquot (preferably, 140 μl) of saline solution or sodium-free saline solution (described above) is added to each tube. Ascorbic acid (2 mg/ml) may be present to reduce oxidation of amines. Pargyline (1 μM) may also be added to inhibit monoamine oxidase (MAO), although, in insects, it is unclear whether or not MAO plays a major role in enzymatic degradation of monoamines.

Tubes are cooled (preferably, to about 4° C.), and radiolabelled octopamine or other phenylethanolamine is added. As described herein, there are many forms of radiolabel which are suitable for the assay. The preferred radiolabel is tritium and the preferred specific activity is 10–40 Ci/mmol, with a final concentration of tritiated octopamine or other phenylethanolamine at 0.5–5 μM in a volume of 20 μl. After adding the drugs (preferably, in a volume of 20 μl of saline), tubes are preincubated at about 31° C. for about 5 min.

The uptake incubation (approximately 10 min at about 31° C.) is started by the addition of 10× synaptosomal fraction (preferably, 20 μl) in sucrose solution. Uptake incubation is terminated by pipetting the contents of the incubation tubes to new tubes half-filled with ice-cold incubation saline solution (or sodium-free saline solution), preferably containing 1 mM phentolamine mesylate and 75 μl of tissue carrier fraction. An equal volume of ice-cold incubation saline solution (or sodium-free saline solution) with phentolamine is added and tubes are centrifuged, preferably for 20 min at 40,000×g, and the supernatant carefully aspirated under low vacuum with a pasteur pipette.

The pellet is left undisturbed, but rapidly and gently washed with about 4 ml of the appropriate ice-cold buffer for approximately 30 sec. Buffer is carefully aspirated and the intact pellet washed gently again with ice-cold buffer for about 30 sec. Following aspiration of the wash, any remaining droplets on the tube nails or bottom are meticulously aspirated, then 0.8 ml of 0.3N NaOH is added directly to the bottom of the tube, and the tube left undisturbed (not vortexed) for several hours to dissolve the pellet. The pellet is then gently triturated (not vortexed) and transferred to a scintillation vial for counting of uptake.

The term "tissue carrier fraction," noted above, is meant to indicate a homogenate of neuronal tissue which is used to increase the recovery of synaptosomes during sedimentation. Surprisingly, the use of the tissue carrier fraction results in a greater than 10-fold increase in recoverable sodium-dependent amine uptake. Preferably, the tissue carrier fraction is a hypotonically-lysed homogenate of rat brain tissue. More preferably, the tissue carrier fraction is prepared by thawing frozen rat brains on ice, removing the brainstem and cerebellum, and thoroughly homogenizing the cerebrum in distilled water (1 brain/10 ml) in a glass/glass homogenizer. The homogenate is centrifuged, preferably, at 40,000×g for 20 min, the supernatant discarded, and the pellet resuspended in 10 ml of distilled water and again centrifuged. The final pellet is resuspended by homogenization in water, preferably, to a final concentration of 1 brain/8 ml, and 1 ml aliquots stored frozen in glass tubes at −55° C. Prior to use, tubes are thawed and placed for about 30 sec in a bath sonicator, following which, in order to block membrane binding by labeled moieties, polyethyleneimine is added, preferably, to a final concentration of 0.1%. Alternatively, either dopamine or octopamine may be added to a final concentration of 1 mM. The tubes are then incubated for about 25 min at room temperature (preferably, 25° C.), and kept on ice.

In both the intact tissue and synaptosomal methods, control (sodium-dependent) uptake is defined as the difference in uptake observed in tubes (or intact tissue) incubated with complete buffer minus that seen in tubes (or tissue) incubated with sodium-free buffer (the latter are termed "blanks"). Alternatively, blanks may utilize: (a) an excess (>1 mM) of non-radioactive octopamine, or (b) an excess (>1 mM) of a transporting blocking agent, or (c) during incubation be kept at 0° C. Typically, tubes (or tissue wells) assaying drug effects contain complete buffer with the compound of interest at concentrations from $10^{31\ 12}M$ to $10^{-3}M$, or from $10^{31\ 12}M$ to $10^{-2}M$. The sodium-dependent uptake in these tubes or tissue pieces containing drug of interest is calculated using the blank noted above and this sodium-dependent uptake then compared with control uptake seen in the absence of any drug.

Although the in vitro assay has been described in considerable detail with reference to certain preferred versions thereof, it will be obvious to a practitioner in the art that modifications may be practiced within the scope of the invention. For example, the pH and the components of the solutions may be modified, and the time and temperature values may be varied. Moreover, following the uptake step, tissue may be separated from unbound radiolabelled octopamine or other phenylethanolamine using an air-driven ultracentrifuge, using a filtration manifold, or by using dialysis. In addition, it is possible to use, as an assay, the binding (and inhibition of binding), to the transporter site, of a radioactively-labeled derivative of a reuptake blocker such as a derivative of chlorethylamine, piperazine, cocaine, or tricyclic antidepressant compounds described herein.

The term "radiolabelled octopamine or other phenylethanolamine" is meant to indicate phenylethanolamines wherein one or more of the atoms thereof are enriched in a radioisotope, or wherein the phenylethanolamine is covalently coupled to a radioisotope label. Examples of such radioisotopes which may enrich the phenylethanolamines of the invention include, but are not limited to $^{3}H$ and $^{14}C$. Examples of radioisotopes which may be used to covalently label the molecule include $^{125}I$, $^{131}I$, $^{32}P$, $^{35}S$ $^{51}Cr$, $^{36}Cl$, $^{57}Co$, $^{58}Co$, $^{59}Fe$, and $^{75}Se$.

The term "octopamine agonist" is meant to indicate a compound which mimics at least some of the effects of octopamine by interaction with the octopamine receptor. For example, an octopamine agonist, like endogenous octopamine, may affect many areas of insect physiology, including carbohydrate metabolism, lipid mobilization, hematocyte function, heart rate, peripheral muscle tension and excitability, and behavior. Thus, overactivation of the octopamine system in insects and acarines by an octopamine agonist may lead to behavioral and physiological abnormalities that have pestistatic and pesticidal consequences. The pest controlling agents of the present invention can be formulated as dusts, water dispersions, emulsions, and solutions. They may comprise accessory agents such as dust carriers, solvents, emulsifiers, wetting and dispersing agents, stickers, deodorants and masking agents (see, for example, Encyclopedia of Chemical Technology, Vol. 13, page 416 et seq.).

Dusts generally will contain low concentration, 0.1–20%, of the compounds, although ground preparations may be used and diluted. Carriers commonly include sulfur, silicon oxides, lime, gypsum, talc, pyrophyllite, bentonites, kaolins, attapulgite, and volcanic ash. Selection of the carrier can be made on the basis of compatibility with the desired pest control composition (including pH, moisture content, and stability), particle size, abrasiveness, absorbability, density, wettability, and cost. The agent of the invention alone or in combination and diluent is made by a variety of simple operations such as milling, solvent-impregnations, fusing and grinding. Particle sizes usually range from 0.5–4.0 microns in diameter.

Wettable powders can be prepared by blending the agents of the invention in high concentrations, usually from 15–95%, with a dust carrier such as bentonite which wets and suspends properly in water. 1 to 2% of a surface-active agent is usually added to improve the wetting and suspendibility of the powder.

The pest-controlling agents can also be used in granules, which are pelleted mixtures of the agents, usually at 2.5–10%, and a dust carrier, e.g., adsorptive clay, bentonite or diatomaceous earth, and commonly within particle sizes of 250 to 590 microns. Granules can be prepared by impregnations of the carrier with a solution or slurry of the agents and can be used principally for mosquito larvae treatment or soil applications.

The agents can also be applied in the form of an emulsion, which comprises a solution of the agents in water immiscible organic solvents, commonly at 15–50%, with a few percent of surface active agent to promote emulsification, wetting, and spreading. The choice of solvent is predicated upon solubility, safety to plants and animals, volatility, flammability, compatibility, odor and cost. The most commonly used solvents are kerosene, xylenes, and related petroleum fractions, methylisobutylketone and amyl acetate. Water emulsion sprays from such emulsive concentrates can be used for plant protection and for household insect control.

The agents can also be mixed with baits, usually comprising 1–5% of agents with a carrier especially attractive to insects. Carriers include sugar for house flies, protein hydrolysate for fruit flies, bran for grasshoppers, and honey, chocolate or peanut butter for ants.

The agents can be included in slow release formulations which incorporate non-persistent compounds, insect growth regulators and sex pheromones in a variety of granular microencapsulated and hollow fiber preparations.

The pest controlling agents of the present invention may be applied depending on the properties of the particular pest controlling compound, the habits of the pest to be controlled and the site of the application to be made. It can be applied by spraying, dusting or fumigation.

Doses of the weight of the ingredients may typically vary between 0.001–100 lbs/acre, preferably between 0.001–5 lbs/acre.

Sprays are the most common means of application and generally will involve the use of water as the principal carrier, although volatile oils can also be used. The pest-control agents of the invention can be used in dilute sprays (e.g., 0.001–10%) or in concentrate sprays in which the composition is contained at 10–98%, and the amount of carrier to be applied is quite reduced. The use of concentrate and ultra low volume sprays will allow the use of atomizing nozzles producing droplets of 30 to 80 microns in diameter. Spraying can be carried out by airplane or helicopter.

Aerosols can also be used to apply the pest controlling agents. These are particularly preferred as space sprays for application to enclosures, particularly against flying insects. Aerosols are applied by atomizing amounts of a liquified gas dispersion or bomb but can be generated on a larger scale by rotary atomizers or twin fluid atomizers.

A simple means of pest control agent dispersal is by dusting. The pest controlling agent is applied by introducing a finely divided carrier with particles typically of 0.5–3 microns in diameter into a moving air stream.

Any octopamine reuptake transporter-containing pest is treatable by the formulation of the present invention. These pests include all invertebrate pests, including, but not limited to, round worms (e.g., hookworm, trichina, ascaris); flatworms (e.g., liver flukes and tapeworms); jointed worms (e.g., leeches); mollusks (e.g., parasitic snails); and arthropods (insects, spiders, centipedes, millipedes, crustaceans (e.g., barnacles)). In particular, included among the arthropods are ticks; mites (both plant and animal); lepidoptera (butterflies and moths and their larvae); hemiptera (bugs); homoptera (aphids, scales); and coleoptera (beetles). Also included are spiders; anoplura (lice); diptera (flies and mosquitoes); trichoptera; orthoptera (e.g., roaches); odonta; thysanura (e.g., silverfish); collembola (e.g., fleas); dermaptera (earwigs); isoptera (termites); ephemerids (mayflies); plecoptera; mallophaga (biting lice); thysanoptera; and siphonaptera (fleas); dictyoptera (roaches); psocoptera (e.g., booklice); and certain hymenoptera (e.g., those whose larva feed on leaves).

Having now generally described this invention, the same will become better understood by reference to certain specific examples which are included herein for purposes of illustration only and are not intended to be limiting unless otherwise specified. All patents and publications cited herein are fully incorporated by reference herein in their entirety.

EXAMPLES

All certified grade reagents or solvents were purchased from Aldrich Chemical Co. or Fluka Chemical Co. All reagents were normally used without further purification. When anhydrous conditions were required, solvents were distilled and dried by standard techniques immediately prior to use.

All air and moisture sensitive reactions were conducted under a prepurified nitrogen atmosphere in flame-dried glassware, previously dried at 150° C. Anhydrous solvents were transferred using conventional syringe or steel canula techniques under an inert atmosphere. Removal of solvents in vacuo was done on a Buchi rotavapor rotary evaporator operated at water aspirator pressure.

$^1$H NMR and $^{13}$C NMR spectra were recorded at 250 Mhz on a Bruker AM250 spectrometer. Optical rotations were recorded on at the Sodium D line on a Rudolph Research Autopol III polarimeter (1 dm cell). Melting point was recorded on a Unimelt Thomas Hoover capillary melting point apparatus in open capillary tubes and were uncorrected. Elemental analysis were performed by Atlantic Microlab, Inc., Norcross, Ga.

Reaction products were purified by flash column chromatography using silica gel (mesh size 230–400) purchased from VWR Scientific. Thin layer chromatography (TLC) was performed on Whatman 254 nm fluorescent silica gel 60A (1×3 inches, 250 [μL thickness]) precoated TLC plates using the solvent systems indicated. Developed chromatograms were evaluated under 254 nm UV light or with iodine.

Example 1

In Vitro Assay For Determination Of Transporter Inhibitory Activity Of Compounds Of Interest The question of whether a given compound is an inhibitor of octopamine neuronal transport can be readily determined by measuring the uptake of radioactive octopamine or similar phenylethanolamine into membrane (synaptosomal) preparations derived from insect or other invertebrate nerve tissue. To prepare membrane preparations, insect ventral nerve cord and brain ganglia from specimens of *Periplaneta americana, Manduca sexta*, or other insect or invertebrate pest are removed and homogenized in a teflon-glass homogenizer in 50 volumes of 0.32M sucrose and then centrifuged at high speed (typically 100,000×g) for 30 minutes to obtain a membrane pellet. The pellet is suspended in insect Ringers solution containing sodium chloride at 0° C. and at a concentration of approximately 10 mg tissue per ml. Optionally, the Ringers may also contain 2 mM ascorbic acid and an inhibitor of monamine oxidase, such as pargyline. 0.2 ml or similar-sized aliquots of the membrane tissue suspension are added to $^3$H-octopamine or similar phenylethanolamine (typically 10–40 mCi/mmol) in test tubes to a final concentration of 1 micromolar of the radioactive amine. Control tubes contain no additional compounds. Other tubes contain the compound of interest to be tested at concentrations of from $10^{-12}$M to $10^{-2}$M. In addition, there are "blank" control tubes in which the sodium chloride in the insect Ringers solution has been substituted with Tris buffer or choline chloride. Alternatively, blanks may utilize: (a) an excess (>1 mM) of non-radioactive octopamine, or (b) an excess (>1 mM) of a transporting blocking agent, or (c) during incubation (see below), be kept at 0° C.

Alternatively, the radioactive compound may be a radioactively-labelled derivative of a reuptake blocker such as a derivative of chlorethylamine, piperazine, cocaine, or tricyclic antidepressant compounds described herein. In this case, inhibition (by the compound of interest) of binding to the transporter site is measured and is equivalent.

To measure octopamine transport (or "uptake") into membranes (or, binding of a reuptake blocker to the transporter site), the tubes are incubated at 20–35° C. for 10–30 minutes, and then the contents of each tube are transferred to glass fiber filters on a filtration manifold and washed quickly under low vacuum with aliquots of ice-cold insect Ringers solution. The filters are then dried and the radioactivity remaining in the filters quantitated by liquid scintillation counting. Alternatively, the membranes may be washed by two cycles of high speed centrifugation, and the radioactivity in the final pellet quantitated by liquid scintillation counting.

After washing, radioactivity counts in the blank are subtracted from the radioactivity quantitated in the other tubes. Radioactivity remaining in the washed control membranes represents baseline phenylethanolamine transport (or, in the case of a labelled transporter blocker, baseline binding to the transporter). The radioactivity in the washed membranes from the tubes containing the compound of interest is plotted relative to control transport (or binding), and the degree of inhibition relative to control uptake is noted. To determine if the compound of interest has substantial inhibitory activity toward octopamine transport, the maximum percent decrease from control seen over the range of concentrations ($10^{-12}$M to $10^{-2}$M) tested is determined. If this value is between 25% and 100%, then the compound is an active inhibitor of transport.

In a more preferable in vitro assay, the question of whether a given compound is an inhibitor of octopamine neuronal transport is readily determined by measuring the uptake of radioactive octopamine or other phenylethanolamine into intact tissue or synaptosomal-containing preparations from insect or other invertebrate nerve tissue.

To measure uptake into intact tissue, hemisected cerebral ganglia and thoracic ganglia are removed from the insect of interest (e.g., *Periplaneta americana*, Blaberus, *Manduca sexta* or other invertebrate pest) and pre-incubated at 28° C. for 15 min in a modified insect saline solution typically containing: 10 mM D-glucose; 130 mM NaCl; 8 mM KCl; 2 mM $CaCl_2$; 2 mM $MgCl_2$; 2.5 mM $K_2CO_3$; 2 mg/ml ascorbic acid; and 50 mM HEPES buffer. The pH is adjusted with NaOH to pH 7.2 (at 31° C.), which gives a final sodium concentration of about 155–160 mM and an osmolality of about 350–355. In order to measure sodium-ependent uptake, some ganglia are pre-incubated in a sodium-free insect saline solution in which sodium chloride is omitted and an equiosmolar amount of Tris buffer (17.6 g Tris HCl and 4.54 g Tris base per liter) added ("sodium-free saline solution"). Both saline solutions may also contain 1 $\mu$M pargyline HCl. After preincubation, tissue is transferred with fine forceps to wells in a 24 well/plate tissue culture dish. Each well contains just enough insect saline solution (approx. 400 $\mu$l/well) to barely cover the tissue pieces, thereby facilitating oxygenation under room atmospheric conditions. Some wells contain the compound to be assayed while others contain sodium-free saline solution. Tritiated octopamine or other phenylethanolamine is present in all wells at a final concentration of approximately 1 $\mu$M and 5 $\mu$Ci/ml. Following incubation for 15 min at 28° C., tissue pieces are transferred by forceps to 10 ml of ice-cold insect saline solution (or sodium-free insect saline solution), gently agitated for 30 sec, then transferred to a second 30 sec ice-cold wash, prior to final transfer to scintillation vials, where tissue is dissolved overnight in 0.5 ml of 0.5N NaOH, following which radioactivity is quantitated and sodium-dependent uptake calculated on the basis of pmol amine/mg protein.

To measure uptake into synaptosomal preparations, the ganglia from the insect of interest is rinsed briefly in cold 0.32M sucrose solution containing 15 mM Tris maleate pH 7.2, and transferred in 1 ml of sucrose/Tris (usually 50 mg tissue/ml) to a 2 ml-sized Teflon-glass homogenizer with 0.25 mm clearance. (A higher sucrose concentration (0.5–0.8M) may improve synaptosomal yield in some species.) Tissue is then gently homogenized on ice at 200 rpm with 10 up and down strokes. The homogenate is transferred to a 12 ml conical plastic tissue-culture tube, 9 ml of cold sucrose/Tris added, and the mixture centrifuged at 800×g for 10 min in the cold in a swinging bucket rotor. The P1 pellet is discarded, and the supernatant transferred to a 10 ml round-bottom thick-walled centrifuge tube and recentrifuged at 40,000×g for 30 min in a fixed angle rotor. The resulting P2 pellet is resuspended by gentle trituration in sucrose/Tris (50 mg original wet weight/ml), transferred to the original Teflon-glass homogenizer, and gently rehomogenized, by hand, to a uniform suspension. This synaptosomal fraction (a 10× stock concentration for most studies) is then stored on ice until use in uptake studies.

Uptake is typically measured in 14×89 mm clear, thin-walled, high speed plastic centrifugation tubes. 140 $\mu$l of modified insect saline solution or sodium-free saline solution (described above) is added to each tube. Ascorbic acid (2 mg/ml) may be present to reduce oxidation of amines. Pargyline (1 $\mu$M) may also be added to inhibit monoamine oxidase (MAO), even though, in insects, it is unclear whether or not MAO plays a major role in enzymatic degradation of monoamines. Tubes are cooled to 4° C., tritiated octopamine or other phenylethanolamine (typically 10–40 Ci/mmol, final concentration 0.5–5 $\mu$M in a volume of 20 $\mu$l) and drugs (in a volume of 20 $\mu$l of water) added, and tubes preincubated at 31° C. for 5 min. The uptake incubation (10 min at 31° C.) is started by the addition of 20 $\mu$l of 10×synaptosomal fraction in 0.32M sucrose/Tris maleate. Uptake incubation is terminated by pipetting the contents of the incubation tubes to new 14×89 mm tubes filled with 4.5 ml of ice-cold incubation saline solution (or sodium-free saline solution) containing 1 mM phentolamine mesylate and 75 $\mu$l of tissue carrier fraction. An additional 4.5 ml of ice-cold incubation saline solution (or sodium-free saline solution) with phentolamine is added and tubes are centrifuged for 20 min at 40,000×g and the supernatant carefully aspirated under low vacuum with a pasteur pipette. The pellet is left undisturbed, but rapidly and gently washed with 4 ml of the appropriate ice-cold buffer for 30 sec. Buffer is carefully aspirated and the intact pellet washed gently again with 2 ml of ice-cold buffer for 30 sec.

Following aspiration of the wash, any remaining droplets on the tube walls or bottom are meticulously aspirated, then 0.8 ml of 0.3N NaOH is added directly to the bottom of the tube, and the tube left undisturbed (not vortexed) for several hours to dissolve the pellet. The pellet is then gently triturated (not vortexed) and transferred to a scintillation vial for counting of uptake.

The tissue carrier fraction noted above is prepared from frozen rat brains which are thawed on ice, the brainstem and cerebellum removed, and the cerebrum thoroughly homogenized in distilled water (1 brain/10 ml) in a glass/glass homogenizer. Homogenate is centrifuged at 40,000×g for 20 min, supernatant discarded, pellet resuspended in 10 ml of distilled water and again centrifuged. The final pellet is resuspended by homogenization in water to a final concentration of 1 brain/8 ml, and 1 ml aliquots stored frozen in glass tubes at −55° C. Prior to use, tubes are thawed and placed for 30 sec in a bath sonicator, following which, in order to block membrane binding by labeled amines, polyethyleneimine is added to a final concentration of 0.1%, or either dopamine or octopamine is added to a final concentration of 1 mM. Tubes are incubated for 25 min at 25° C., and then kept on ice.

In both the intact tissue and synaptosomal methods, control (sodium-dependent) uptake is defined as the difference in uptake observed in tubes (or intact tissue) incubated with complete buffer minus that seen in tubes (or tissue) incubated with sodium-free buffer (the latter are termed "blanks"). Alternatively, blanks may utilize: (a) an excess (>1 mM) of non-radioactive octopamine, or (b) an excess (>1 mM) of a transporting blocking agent, or (c) during incubation be kept at 0° C. Typically, tubes (or tissue wells) assaying drug effects contain complete buffer with the compound of interest at concentrations from $10^{-12}$M to $10^{-3}$M, or from $10^{-12}$M to $10^{-2}$M. The sodium-dependent uptake in these tubes or tissue pieces containing drug of interest is calculated using the blank noted above and this sodium-dependent uptake then compared with control uptake seen in the absence of any drug. To determine if the compound of interest has substantial inhibitory activity toward octopamine transport, the maximum percent decrease from control seen over the range of drug concentrations ($10^{-12}$M to $10^{-3}$M, or $10^{-12}$M to $10^{-2}$M) tested is determined. If this decrease is between 25% and 100% of the control value, then the compound is an active inhibitor of transport.

The compounds of this invention can be prepared according to the synthesis methods described in the parent applications. Alternative synthesis for related compounds will be apparent to those of ordinary skill in the art. Particular synthesis schemes are exemplified in U.S. Pat. No. 5,444,070, which is incorporated herein in its entirety. Additional schemes follow hereinbelow.

Example 2

Preparation of 3β-(Substituted phenyl)tropane-2β-heterocyclic Analogues

Chemistry

The known 3β-(substituted phenyl)-2β-tropane carboxylic acid (tropane acid) (Carroll et al., *J. Med. Chem.* 35:1813–1817 (1992)) served as the starting material for the synthesis of 2β-substituted oxazoles, oxadiazoles, thiazoles, thiadiazoles and benzothiazole as shown in FIG. 1.

The tropane acid was refluxed with N-acetyl and benzoic hydrazide in phosphorous oxychloride to obtain the corresponding 5-substituted 1,3,4-oxadiazoles (Afanasiadi et al., *Chem. Heterocyclic Compd.* 397–400 (1995)). N-benzoyl hydrazide amide obtained by the reaction of the acid chloride of tropane acid with N-benzoic hydrazide was cyclized with Lawesson's reagent (El-Barbary et al., *Acta Chimica Scandinavica* 597–601 (1980)) in refluxing THF to the 5substituted 1,3,4-thiadiazoles. The N-phenylacyl carboxamide obtained from tropane acid and 2-aminoacetophenone was cyclized by refluxing the amide in phosphorous oxychloride to obtain the required 5-substituted oxazoles (Carroll et al., *Med. Chem. Res.* 3:468 (1993)). Cyclization of the same amide with Lawesson's reagent (El-Barbary et al., 1980) in refluxing THF gave the 5-substituted thiazoles respectively. The benzothiazole was obtained without the cyclization step by the reaction of acid chloride obtained from the appropriate tropane acid with 2-aminothiophenol.

Figure 2:
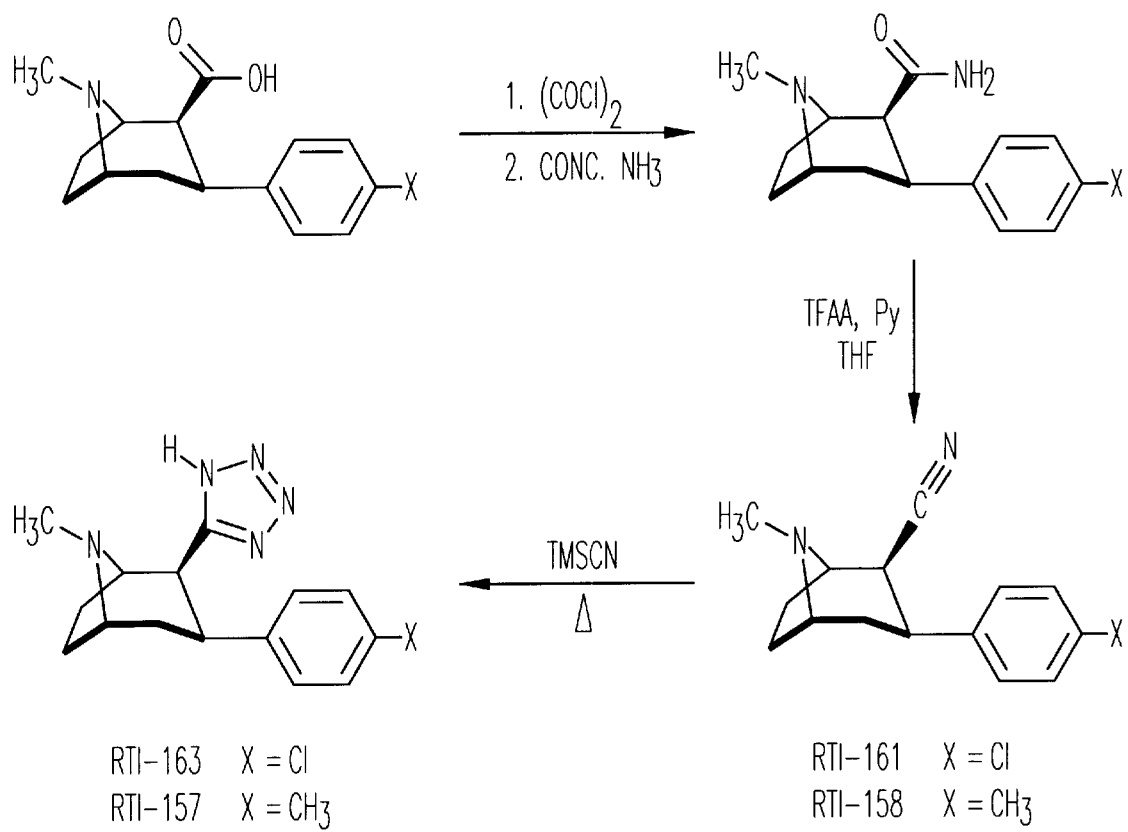
FIG. 2 depicts the scheme in which the carboxamide obtained from the tropane acid was treated to obtain nitriles and tetrazoles.

The previously reported carboxamide (FIG. 2) (Carroll et al., 1993) obtained from the tropane acid was dehydrated with trifluoroacetic anhydride and pyridine in THF to the nitriles (Campagna et al., *Tet. Letts.* 22:1813–1816 (1977)) as shown in FIG. 2. Cycloaddition of trimethylsilylazide to the nitrile afforded the corresponding tetrazoles (Saunders et al., *J. Med. Chem.* 33:1128–1138 (1990)).

Figure 3:
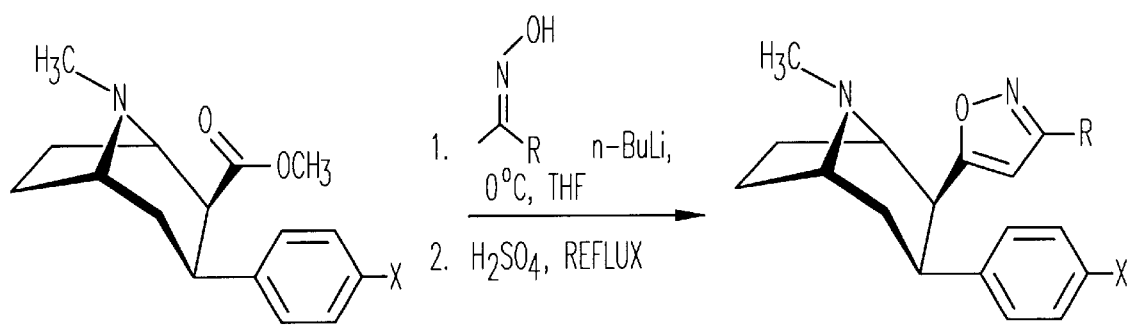
FIG. 3 depicts the scheme used to prepare 3-substituted isoxazoles.

FIG. 3 outlines the route used to prepare 3-substituted isoxazole. The known tropane compounds (Carroll et al., *J. Med. Chem.* 34:2719–2725 (1991)) were treated with dilithiated methyl or phenyl acetoneoximes, obtained by the treatment of acetoxime or acetophenoneoxime with n-BuLi at 0° C. The corresponding addition product was cyclized without isolation using sulfuric acid at reflux temperature to furnish the required isoxazoles (Saunders et al., 1990).

Example 3

General Procedure For the Preparation of Amides

To a solution of 1 mmol of 3β-(4-Chlorophenyl)-tropane-2β-carboxylic acid or 3β-(4-Methylphenyl)-tropane-2β-carboxylic acid in 5 ml of methylene chloride was added dropwise with stirring under nitrogen 2.0 eq oxalyl chloride (2M solution in methylene chloride). The resulting solution was stirred at room temperature for an hour after evolution of gas has ceased. The solvent was removed in vacuo at room temperature and then at high vacuum to remove residual traces of oxalyl chloride. The resulting residue of acid chloride was suspended in 5 ml methylene chloride under nitrogen at 0° C., and 2.0 eq of the amine hydrochloride containing 4.0 eq of triethylamine, or 2.5 eq of the amine free base was added. The mixture was stirred at room temperature overnight. Aqueous 3N NaOH (5 ml) was added to basify the reaction mixture, the organic layer was separated and the aqueous layer extracted with 3×10 ml chloroform. The combined organic layers were dried ($Na_2SO_4$), filtered and the solvent removed in vacuo to give crude product. The crude was purified by flash column chromatography or crystallization.

Example 4

3β-(4-Chlorophenyl)-2β-(5-pheny-1,3,4-oxadiazol-2-yl)-tropane Hydrochloride (RTI-188)

To a solution of 0.59 g (2 mmol) of 3β-(4-Chlorophenyl) tropane-2β-carboxylic acid (chloro acid) in 2 ml of $POCl_3$ was added 0.31 g (2.2 mmol) of N-benzoic hydrazide and refluxed under nitrogen for 2 hours. The reaction mixture was cooled, poured into ice and rendered basic to pH 7–8 using concentrated $NH_4OH$. To the ice cold aqueous layer was added 10 ml brine and extracted thrice with 10 ml methylene chloride. The organic layers were combined dried ($NaSO_4$), filtered, and the solvent removed in vacuo to give 0.9 g of crude residue. Purification of the residue by flash column chromatography [50% (ether/triethylamine 9:1) in hexane] gave 0.33 g (42%) of pure oxadiazole (RTI-188) which was recrystallized from ether/petroleum ether: $^1$H NMR ($CDCl_3$) 1.81 (m, 3 H), 2.18 (s, 3 H), 2.26 (m, 2 H), 2.66 (m, 1 H), 3.33 (m, 2 H), 3.51 (m, 2 H), 7.16 (m, 4 H) 7.45 (m, 3 H), 7.86 (m, 2 H); IR ($CHCl_3$) 2950, 1550, 1490, 1450, 1340, 1090 $cm^{-1}$; $[\alpha]_D$–106.25° (c=0.08, $CHCl_3$).

The oxadiazole was converted into hydrochloride salt: $^1$H NMR (MeOD) 2.08 (m, 1 H), 2.57 (m, 5 H), 3.0 (s, 3 H), 4.01 (m, 2 H), 4.15 (m, 1 H), 4.39 (m, 1 H), 7.24 (m, 4 H), 7.52 (m, 5 H): mp 160–162° C.; Anal calcd for $C_{22}H_{23}Cl_2N_3O.0.75H_2O$; C=61.47; H=5.74, N=9.78; Cl=16.50; found C=61.47, H=5.73, N=9.76; Cl=16.56; $[\alpha]_D$ +84.59° (c=0.36, $CH_3OH$).

Further elution gave as a second fraction 0.1 g (13%) of white solid which was characterized to be 3β-(4-Chlorophenyl)-2α-(5-phenyl-1,3,4-oxadiazol-2-yl)-tropane: $^1$H NMR ($CDCl_3$) 1.76 (m, 3 H), 2.06 (s, 3 H), 2.45 (s, 3 H), 3.36 (m, 2 H), 3.51 (m, 1 H), 3.65 (m, 1 H), 7.21 (m, 4 H), 7.47 (m, 3 H) 7.91 (m, 2 H); mp 170–171° C.; Anal calcd for $C_{22}H_{22}ClN_3O$; C=69.55; H=5.84, N=11.06; Cl=9.33; found C=69.49, H=5.85, N=11.01; Cl=9.41; $[\alpha]_D$ +33.060° (c=0.18, $CHCl_3$).

Example 5

3β-(4-Methylphenyl)-2β-(5-phenyl-1,3,4-oxadiazol-2-yl)-tropane Hydrochloride (RTI-195)

Reaction of 0.65 g (2.5 mmol) of 3β-(4-Methylphenyl)-tropane-2β-carboxylic acid (Methyl acid) as described above for RTI-188 gave after work-up and purification by flash column chromatography [(50% (ether/triethylamine 9:1) in hexane] 0.36 g (40%) of pure oxadiazole (RTI-195)

which was recrystallized from ether/petroleum ether: $^1$H NMR (CDCl$_3$) 1.83 (m, 3 H), 2.18 (s, 3 H), 2.21 (s, 3 H), 2.3 (m, 2 H), 2.67 (m, 1 H), 3.33 (m, 1 H)., 3.41 (m, 1 H), 3.53 (m, 1 H), 3.61 (m, 1 H) 7.0 (m, 2 H).7.13 (m, 2 H), 7.44 (m, 3 H), 7.86 (m, 2 H); IR (CHCL$_3$) 2990, 1545, 1505, 1440, 1350. cm$^{-1}$; [α]$_D$ −163.92° (c=0.2, CHCl$_3$).

The oxadiazole was converted into hydrochloride salt: $^1$H NMR (MeOD) 2.05 (m, 1 H), 2.21 (s, 3 H), 2.51 (m, 5 H), 2.99 (s, 3 H), 3.86 (m, 1 H), 3.95 (m, 1 H), 4.14 (m, 1 H), 4.35 (m, 1 H), 7.02 (m, 4 H) 7.53 (m, 5 H); mp 175–178° C.; Anal calcd for C$_{23}$H$_{26}$ClN$_3$O.0.75H$_2$O; C=67.47; H=6.77, N=10.26; Cl=8.66; found C=67.58, H=6.79, N=10.34; Cl=8.78; [α]$_D$ +97.22° (c=0.25, CH$_3$OH).

Further elution gave as a second fraction 0.18g (20%) of solid which was characterized to be 3β-(4-Methylphenyl)-2α-(5-phenyl-1,3,4-oxadiazol-2-yl)-tropane which was recrystallized from ether/ petroleum ether: $^1$H NMR (CDCl$_3$) 1.77 (m, 2 H), 2.0 (m, 4 H), 2.25 (s, 3 H), 2.47 (s, 3 H), 3.33 (m, 2 H), 3.51 (m, 1 H), 3.69 (d of d, J=2.6, 12 Hz, 1 H), 6.91 (m, 2 H) 7.03 (m, 2 H).7.45 (m, 2 H), 7.45 (m, 3 H), 7.89 (m, 2 H); IR (CHCL$_3$) 3020, 1540, 1510, 1415, 1250, 1215. cm$_{-1}$; Anal calcd for C$_{23}$H$_{25}$N$_3$O; C=76.85; H=7.01, N=11.69; found C=76.60, H=7.12, N=11.55; [α]$_D$ +40.73° (c=0.28, CHCl$_3$).

Example 6

3β-(4-Methylphenyl)-2β-(5-methyl-1,3,4-oxadiazol-2-yl)-tropane Hydrochloride (RTI-194)

Reaction of 0.65 g (2.5 mmol) of methyl acid as described above for RTI-195 using 0.21 g (2.75 mmol) of N-acetic hydrazide gave after work-up and Purification by flash column chromatography [(75% (ether/triethylamine 9:1) in hexane] 0.29 g (39%) of pure oxadiazole (RTI-194) which was recrystallized from ether/petroleum ether: $^1$H NMR (CDCl$_3$) 1.75 (m, 3 H), 2.18 (s, 3 H), 2.22 (s, 3 H), 2.25 (m, 2 H), 2.35 (s, 3 H), 2.56 (m, 1 H), 3.24 (m, 1 H), 3.4 (m, 2 H), 3.47 (m, 1 H) 7.0 (m, 4 H); $^{13}$C NMR (CDCl$_3$) 11.06, 20.9, 25.08, 26.32, 34.11, 34.6, 41.83, 45.73, 61.97, 66.21, 127.11, 128.85, 135.85, 138.19, 162.5, 167.44; IR (CHCL$_3$) 2950, 1590, 1510, 1450, 1350, 1215 cm$^{-1}$; [α]$_D$ −108.47° (c=0.14, CHCl$_3$).

The oxadiazole was converted into hydrochloride salt: $^1$H NMR (MeOD) 1.99 (m, 1 H), 2.23 (s, 3 H), 2.27 (s, 3 H), 2.47 (m, 5 H), 2.94 (s, 3 H), 3.72 (m, 1 H), 3.79 (m, 1 H), 4.10 (m,1 H), 4.23 (m, 1 H), 7.05 (m, 4 H); mp 146° C.(dec); Anal calcd for C$_{18}$H$_{24}$ClN$_3$O.0.5H$_2$O; C=63.06; H=7.35, N=12.26; Cl=10.34; found C=63.21, H=7.40, N=12.07; Cl=10.27; [α]$_D$ −43.05° (c=0.15, CH$_3$OH).

Example 7

3β-(4-Chlorophenyl)-2β-(5-phenyl-1,3,4-thiadiazol-2-yl)-tropane Hydrochloride (RTI-200).

Reaction of 0.59 g (2 mmol) of 3β-(4-Chlorophenyl) tropane-2β-carboxylic acid as described above for the preparation of amides gave after purification of the crude by crystallizing from ethyl acetate/ether 0.52 g (66%) of pure N-[3β-(4-Chlorophenyl)-tropane-2β-carboxylic]-N'-benzoylhydrazide: $^1$H NMR (CDCl$_3$) δ 1.76 (m, 3 H), 2.24 (m, 2 H), 2.41 (s, 3 H), 2.51 (m, 1 H), 2.68 (m, 1 H), 3.18 (m, 1 H), 3.44 (m, 2 H), 7.22 (m, 4 H), 7.46 (m, 3 H), 7.78 (m, 2 H), 9.02 (br s, 1 H), 12.97 (br s, 1 H); IR (CHCl$_3$) 3385, 3035, 3000, 1620, 1570, 1485, 1450, 1215 cm$^{-1}$.

A solution of 0.4 g (1 mmol) of N-[3β-(4-Chlorophenyl)-tropane-2β-carboxylic]-N'-benzoyl-hydrazide and 0.8 g (2 mmol) of Lawesson's reagent in 10 ml toluene was refluxed for 4 h under nitrogen. The reaction mixture was cooled and solvent removed in vacuo to give a yellow residue. To the residue was added 3 g of silica gel and 10 ml of methylene chloride, the resulting slurry was mixed properly and the solvent removed in vacuo. The crude compound impregnated on silica gel was loaded on a column and purified by flash column chromatography [50% ether/triethylamine(9:1) in hexane] to obtain 0.23 g (58%) of pure thiadiazole (RTI-200) which was further purified by recrystallizing from ether: $^1$H NMR (CDCl$_3$) δ 1.75 (m, 3 H), 2.20 (m, 3 H), 2.32 (s, 3 H), 3.30 (m, 3 H), 3.78 (m, 1 H), 6.86 (m, 2 H), 7.08 (m, 2 H), 7.43 (m,3 H), 7.97 (m, 2 H); $^{13}$C NMR 25.55, 25.88, 34.60, 36.09, 41.55, 49.73, 61.48, 65.33, 127.59, 128.28, 128.78, 128.88, 130.37, 130.88, 132.19, 139.27, 168–29, 169.56; IR (CCl$_4$) 2940, 1490, 1460, 1340, 1245, 1100, 1010 cm$^{-1}$.

The thiadiazole was converted into hydrochloride salt: $^1$H NMR (MeOD) δ 2.06 (m, 1 H), 2.53 (m, 5 H), 2.97 (s, 3 H), 3.92 (m, 1 H), 4.17 (m, 2 H), 4.39 (m, 1 H), 7.11 (m, 2 H), 7.26 (m, 2 H), 7.51 (m, 3 H), 7.79 (m, 2 H); mp 165–170° C.; Anal calcd for C$_{22}$H$_{23}$Cl$_2$N$_3$S.0.75H$_2$O; C=59.26, H=5.54, N 9.42, Cl=15.90; S=7.19. found C=59.27, H=5.52, N=9.40, Cl=15.99; S 7.09; [α]$_D$ −42.810 (c=0.16, MeOH).

Further elution gave 0.08 g (21%) as a second fraction which was characterized to be 3β-(4-chlorophenyl)-2α-(5-phenyl-1,3,4-oxadiazol-2-yl)-tropane.

Example 8

3β-(4-Methylphenyl)-2β-(5-phenyl-1,3,4-thiadiazol-2-yl)-tropane Hydrochloride (RTI-199)

Reaction of 0.65 g (2.5 mmol) of 3β-(4-Methylphenyl)-tropane-2β-carboxylic acid as described above for preparation of amides gave after work up and purification by flash column chromatography [(50% CMA-80 in methylene chloride)] 0.48 g (51%) pure N-[3β-(4-Methylphenyl)-tropane-2β-carboxylic]-N'-benzoyl-hydrazide which was further purified by recrystallizing from ether/pet ether: $^1$H NMR (CDCl$_3$) δ 1.75 (m, 3 H), 2.20 (m, 2 H), 2.27 (s, 3 H), 2.42 (s, 3 H), 2.51 (m, 1 H), 2.67 (m, 1 H), 3.18 (m, 1 H), 3.47 (m, 2 H), 7.11 (m, 4 H), 7.48 (m, 3 H), 7.81 (m, 2 H), 9.06 (br s, 1 H), 13.09 (br S, 1 H); IR (CHCl$_3$) 3385, 3045, 1625, 1570, 1460, 1420, 1100 cm$^{-1}$;

Reaction of 0.29 g (0.75 mmol) of N-[3β-(4-Methylphenyl)-tropane-2β-carboxylic]-N'-benzoyl-hydrazide as described above for RTI-200 gave after work and purification by flash chromatography [40% ether/triethylamine(9:1) in hexane] 0.16 g (58%) of pure thiadiazole (RTI-199): $^1$H NMR (CDCl$_3$) δ 1.70 (m, 1 H), 1.88 (m, 2 H), 2.20 (s, 3 H), 2.23 (m, 2 H), 2.21 (s, 3 H), 2.38 (m, 1 H), 3.21 (m, 1 H), 3.32 (m, 1 H), 3.39 (m, 1 H), 3.78 (m, 1 H), 6.81 (m, 2 H), 6.92 (m, 2 H), 7.43 (m,3 H), 7.97 (m, 2 H); $^{13}$C NMR 20.98, 25.65, 25.95, 34.79, 36.25, 41.65, 50.05, 61.68, 65.49, 127.32, 127.65, 128.89, 128.95, 130.29, 131.11, 135.94, 137.68, 168.83, 169.45; IR (CCl$_4$) 2935, 1510, 1450, 1250, 1120, 1100, 1060 cm$^{-1}$ The thiadiazole was converted into hydrochloride salt; $^1$H NMR (MeOD) δ 1.95 (m, 1 H), 2.17 (s, 3 H), 2.41 (m, 5 H), 2.89 (s, 3 H), 3.76 (m, 1 H), 4.05 (m, 2 H), 4.30 (m, 1 H), 4.22 (m, 1 H), 6.89 (m, 2 H), 6.99 (m, 2 H), 7.39 (m, 3 H), 7.67 (m, 2 H); mp 180–185° C.; Anal calcd for C$_{23}$H$_{26}$ClN$_3$S.H$_2$O; C=65.62, H=6.46, N=9.98, Cl=18.42; S=7.62. found C=65.57, H=6.63, N=9.91, Cl=18.24; S=7.55; [α]$_D$ −33.5° (c=0.2, MeOH).

Further elution gave 0.04 g (15%) of a second fraction which was characterized to be 3β-(4-Methylphenyl)-2α(5-phenyl-1,3,4-oxadiazol-2-yl)-tropane.

Example 9

3β-(4-Chlorophenyl)-2β-(5-phenyl-oxazol-2-yl)-tropane Tartrate RTI-189)

Reaction of 0.73 g (2.5 mmol) of 3β-(4-Chlorophenyl)-tropane-2β carboxylic acid as described above for the preparation of amides gave after purification by flash column chromatography (15% CMA 80 in methylene chloride) 0.8 g (81%) of pure 3β-(4-Chlorophenyl)-tropane-2β-N-(phenyacyl)carboxamide: $^1$H NMR (CDCl$_3$) δ 1.71 (m, 3 H), 2.19 (m, 2 H), 2.39 (s, 3 H), 2.46 (m, 1 H), 2.58 (m, 1 H), 3.13 (m, 1 H), 3.43 (m, 2 H), 4.74 (m, 2 H), 7.13 (m, 4 H), 7.49 (m, 2 H), 7.59 (m, 1 H), 7.96 (m, 2 H), 10.57 (br s, 1 H); IR (CHCl$_3$) 3135, 3010, 2930, 1695, 1650, 1590, 1530, 1485, 1450, 1355, 1220 cm$^{-1}$.

A solution of 0.725 g (1.83 mmol) of 3β-(4-Chlorophenyl)-tropane-2β-N(phenyacyl)carboxamide in 6 ml POCl$_3$ was heated at 125° C. under nitrogen for 2 hours. The reaction mixture was cooled and poured into ice and rendered basic to pH 7–8 using concentrated NH$_4$OH. To the ice cold aqueous layer was added 10 ml brine and extracted thrice with 10 ml methylene chloride. The organic layers were combined dried (NaSO$_4$), filtered, and the solvent removed in vacuo to 0.63 g crude oxazole. Purification of the crude by flash column chromatography [(40% (ether/triethylamine 9:1) in hexane] gave 0.34 g (49%) of pure oxazole (RTI-189) which was further purified by recrystallizing from ether/petroleum ether: $^1$H NMR (CDCl$_3$) 1.79 (m, 3 H), 2.22 (s, 3 H), 2.27 (m, 2 H), 2.66 (m, 1 H), 3.27 (m, 1 H), 3.40 (m, 2 H), 3.53 (m, 1 H), 7.11 (s, 1 H), 7.16 (s, 4 H) 7.31 (m, 5 H); IR (CHCl3) 2950, 1540, 1490, 1445, 1350, 1120, 1090 CM$^{-1}$; [α]$_D$ −70.37° (c=0.19, CHCl$_3$).

The oxazole was converted into tartrate salt: $^1$H NMR (MeOD) 2.14 (m, 1 H), 2.54 (m, 5 H), 2.96 (s, 3 H), 3.75 (m, 2 H), 4.12 (m, 1 H), 4.25 (m, 1 H), 4.41 (s, 2 H), 7.05 (m, 2 H), 7.29 (m, 7 H), 7.45 (s, 1 H), 7.43 (s, 1 H); mp 126° C. (dec); Anal calcd for C$_{27}$H$_{29}$ClN$_2$O$_7$.0.75H$_2$O; C=59.78; H=5.67, N=5.16; Cl=6.54; found C=59.78, H=5.58, N=4.93; Cl=6.31; [α]$_D$ +101.43° (c=0.21, CH$_3$OH).

Example 10

3β-(4-Methylphenyl)-2β-(5-phenyl-oxazol-2-yl)-tropane Tartrate (RTI-178)

Reaction of 0.52 g (2 mmol) of 3β-(4-Methylphenyl)-tropane-2β-carboxylic acid as described above for preparation of amides gave after work up and purification by flash column chromatography (15% CMA in methylene chloride) 0.54 g (72%) of pure 3β-(4-Methylphenyl)-tropane-2β-N-(phenyacyl)carboxamide: $^1$H NMR (CDCl$_3$) δ 1.73 (m, 3 H), 2.14 (m, 2 H), 2.26 (s, 3 H), 2.40 (s, 3 H), 2.47 (m, 1 H), 2.59 (m, 1 H), 3.14 (m, 1 H), 3.42 (m, 2 H), 4.74 (m, 2 H), 7.05 (m, 4 H), 7.48 (m, 2 H), 7.59 (m, 2 H), 7.97 (m, 2 H), 10.62 (br s, 1 H); IR (CHCl$_3$) 3155, 3005, 2930, 1690, 1650, 1520, 1450, 1355, 1215 cm$^{-1}$ Reaction of 0.5 g (1.33 mmol) of 3β-(4-Methylphenyl)-tropane-2β-N-(phenyacyl)carboxamide as described above for RTI-189 gave after workup and purification by flash column chromatography [(40% (ether/triethylamine 9:1) in hexane] 0.1 g (31%) RTI-158 as a first fraction. Further elution gave 0.19 g (42%) of pure oxazole RTI-178: $^1$H NMR (CDCl$_3$) 1.8 (m, 3 H), 2.18 (m, 2 H), 2.21 (s, 3 H), 2.22 (s, 3 H), 2.67 (m, 1 H), 3.28 (m, 1 H), 3.42 (m, 2 H), 3.53 (m, I H), 6.98 (m, 2 H), 7.11 (m, 3 H), 7.30 (m, 5 H).

The oxazole was crystallized as the tartrate salt: $^1$H NMR (MeOD) 1.99 (m, 1 H), 2.19 (s, 3 H), 2.54 (m, 5 H), 2.95 (s, 3 H), 3.74 (m, 2 H), 4.13 (m, 1 H), 4.26 (m, 1 H), 4.4 (s, 2 H), 6.91 (m, 2 H), 7.0 (m, 2 H), 7.25 (m, 2 H), 7.33 (m, 3 H), 7.43 (s, 1 H); mp 175–181 C.; Anal calcd for C$_{28}$H$_{32}$N$_2$O$_7$.1H$_2$O; C=63.87; H=6.51, N=5.32; found C=64.21, H=6.40, N=5.19; [α]$_D$ −104.040 (c=0.6, CH$_3$OH).

Example 11

3β-(4-Chlorophenyl)-2β-(5-phenylthiazol-2-yl)-tropane Hydrochloride (RTI-219)

To a solution of 0.74 g (1.86 mmol) of 3β-(4-Chlorophenyl)-tropane-2β-N-(phenyacyl)carboxamide and 1.51 g (7.45 mmol) of Lawesson's reagent in 18 ml of toluene was refluxed under N$_2$ for 5 hours. The reaction mixture was cooled and solvent removed in vacuo to give crude residue. To the residue was added 3 g of silica gel and 10 ml of methylene chloride, the resulting slurry was mixed properly and the solvent removed in vacuo. The crude compound impregnated on silica gel was loaded on a column and purified by flash column chromatography [(40% (ether/triethylamine 9:1) in hexane] to give 0.21 g (30%) of pure thiazole RTI-219: $^1$H NMR (CDCl$_3$) 1.61 (m, 1 H), 1.82 (m, 2 H), 2.22 (m, 2 H), 2.34 (s, 3 H), 2.39 (m, 1 H), 3.28 (m, 2 H), 3.39 (m, 1 H), 3.49 (m, 1 H), 6.8 (m, 2 H) 7.07 (m, 2 H).7.32 (m, 3 H), 7.57 (m, 2 H), 7.60 (s, 1 H); $^{13}$C NMR (MeOD) 25.51, 25.99, 35.01, 36.92, 41.72, 52.97, 61.58, 65.70, 126.45, 127.60, 128.13, 128.89, 129.05, 131.91, 132.43, 136.11, 139.91, 140.27, 168.97; IR (CHCl$_3$) 2945, 1590, 1485, 1445, 1350, 1125, 1090. cm$^{-1}$.

The thiazole was converted into hydrochloride salt: $^1$H NMR (MeOD) 1.99 (m, 1 H), 2.51 (m, 5 H), 2.93 (s, 3 H), 3.79 (m, 2 H), 4.15 (m, 1 H), 4.28 (m, 1 H), 7.02 (d, J=8.5 Hz, 2 H) 7.21 (d, J=8.5 Hz, 2 H), 7.39 (m, 5 H), 8.06 (s, 1 H); mp 228–230° C.; Anal calcd for C$_{23}$H$_{24}$ClN$_2$S.H$_2$O; C=61.47, H=5.83, N=6.23, S=7.13, Cl=15.78; found C=61.61, H=5.76, N=6.20, S=7.51, Cl=15.84; [α]$_D$ +27.43° (c=0.11, CH$_3$OH).

Example 12

3β-(4-Chlorophenyl)-2β-(benzothiazol-2-yl)-tropane Hydrochloride (RTI-202)

Reaction of 0.59 g (2 mmol) of 3β-(4-Chlorophenyl)-tropane-2β-carboxylic acid as described above for preparation of amides gave after purification of the crude by flash column chromatography (50% CMA-80 in methylene chloride) 0.3 g (41%) of pure RTI-202 which was further purified by recrystallizing from ether/hexane: $^1$H NMR (CDCl$_3$) δ 1.65 (m, 1 H), 1.87 (m, 2 H), 2.24 (m, 2 H), 2.34 (s, 3 H), 2.41 (m, 1 H), 3.28 (m, 2 H), 3.40 (m, 1 H), 3.62 (m, 1 H), 6.8 (m, 2 H), 6.81 (m, 2 H), 7.29 (m, 2 H), 7.70 (m, 1 H), 7.84 (m, 1 H); $^{13}$C NMR (CDCl$_3$) δ 25.58, 26.07, 35.40, 36.95, 41.56, 53.09, 61.57, 65.47, 120.95, 122.42, 124.11, 125.20, 128.05, 129.03, 131.87, 136.72, 139.91, 151.33, 171.11; IR (CHCl$_3$) 2940, 2795, 1495, 1445, 1305, 1130, 1105, 1015, 907 CM$^{-1}$; [α]$_D$ −233.89° (c=0.09, CHCl$_3$).

The benzothiazole was converted into hydrochloride salt: $^1$H NMR (MeOD) 6 2.02 (m, 1 H), 2.43 (m, 4 H), 2.89 (m, 1 H), 2.98 (s, 3 H), 3.90 (m, 2 H), 4.23 (m, 1 H), 4.34 (m, 1 H), 7.02 (m, 2 H), 7.13 (m, 2 H), 7.45 (m, 2 H), 7.81 (m, 1 H), 8.16 (m, 1 H); mp 140–150° C. (dec); Anal calcd for C$_{21}$H$_{22}$Cl$_2$N$_2$S.0.75H$_2$O C=60.21, H=5.65, N=6.69, Cl=16.93; S=7.65: found C=60.14, H=5.74, N=6.60, Cl=16.89; S=7.71; [α]$_D$ −172.49° (c 0.28, MeOH).

Example 13

3β-(4-Chlorophenyl)-tropane-2β-nitrile (RTI-161)

To a solution of 0.95 g (3.5 mmol) of 3β-(4-Chlorophenyl)-tropane-2β-carboxamide in 20 ml dry THF was added 0.56 ml (7 mmol) pyridine. To the resulting solution at room temperature was added dropwise with stirring under nitrogen 0.35 ml (4.2 mmol) of trifluoroacetic anhydride. The reaction was stirred at room temperature for 30 minutes, and quenched with 10 ml water. The solvent was removed under vacuo and the residue was taken in 10 ml saturated aqueous $K_2CO_3$ and extracted thrice with 10 ml $CHCl_3$. The organic layers were combined and washed with 20 ml brine dried ($NaSO_4$), filtered, and the solvent removed in vacuo to give 0.26 g crude product. Purification of the crude by flash column chromatography (10% CMA in methylene chloride) gave 0.68 g (77%) of pure nitrile RTI-161 which was recrystallized from methylene chloride and hexane: $^1$H NMR ($CDCl_3$) δ 1.70 (m, 3 H), 2.22 (m, 3 H), 2.35 (s, 3 H), 2.80 (m, 1 H), 3.04 (m, 1 H), 3.34 (m, 1 H), 3.43 (m, 1 H), 7.26 (m, 4 H); IR ($CHCl_3$) 3700, 2950, 2225, 1490, 1470, 1090, 900 $cm^{-1}$; mp 167–173° C.; Anal calcd for $C_{15}H_{18}Cl_2N_2.0.75H_2O$; C=57.98, H 6.32 N=9.02, Cl=22.82; found C=58.22, H=6.12, N=8.48, Cl=22.89; $[\alpha]_D$ –73.33° (c=0.48, MeOH).

Example 14

3β-(4-Methylphenyl)-tropane-2β-nitrile Hydrochloride (RTI-158)

Reaction of 0.26 g (1 mmol) of 3β-(4-Methylphenyl)-tropane-2β-carboxamide as described above for RTI-161 gave after work up and purification 0.16 g (67%) of pure nitrile (RTI-158): $^1$H NMR ($CDCl_3$) δ 1.68 (m, 3 H), 2.18 (m, 3 H), 2.32 (s, 3 H), 2.35 (s, 1 H), 2.82 (m, 1 H), 3.02 (m, 1 H), 3.36 (m, 1 H), 3.43 (m, 1 H), 7.18 (m, 4 H); IR ($CHCl_3$) 3675, 3000, 2950, 2200, 1600, 1510, 1450, 1350, 1220, 1100 $cm^{-1}$.

The crude product was crystallized as the HCl salt: $^1$H NMR (MeOH) δ 2.08–2.58 (m, 9 H), 2.92 (s, 3 H), 3.54 (m, 1 H), 3.69 (br s, 1 H), 4.12 (br s, 1 H), 4.29 (m, 1 H), 7.21 (m, 4 H); mp 270° C. (dec.); Anal calcd for $C_{16}H_{21}ClN_2$; C=69.42, H=7.65 N=10.12, Cl=12.81; found C=69.31, H=7.70, N=10.12, Cl=12.81; $[\alpha]_D$ –76.4° (c=0.5, MeOH).

Example 15

3β-(4-Chlorophenyl)-tropane-2β-tetrazole (RTI-163)

To a solution of 0.13 g (0.5 mmol) of RTI-161 in 5 ml dry THF was added 0.28 ml (5 mmol) azidotrimethylsilane and the mixture was placed in a PTFE-lined autoclave. The solution was heated to 150° C. for 24 hours in an oil bath. The reaction mixture was cooled and transferred using MeOH. The solvent was removed in vacuo to give a brownish residue. Purification of the crude by flash column chromatography (20%–50% CMA in methylene chloride) gave 0.05 g (33%) of pure tetrazole (RTI-163): $^1$H NMR ($CDCl_3$+1 drop MeOD) δ 1.73 (m, 1 H), 2.44–2.02 (m, 4 H), 2.6 (m, 1 H), 2.68 (s, 3 H), 3.33 (m, 1 H), 3.65 (m, 1 H, 3.73 (m, 1 H, 3.97 (m, 1 H), 6.68 (d, J=8 Hz, 2 H), 7.07 (d, J=8 Hz, 2 H); mp 296–300° C.; Anal calcd for $C_{15}H_{18}ClN_5.0.75H_2O$; C=56.78, H=6.19 N=22.07, Cl=11.17; found C=56.69, H=6.22, N=22.09, Cl=11.15; $[\alpha]_D$ –124.940 (c=0.39, MeOH).

Example 16

3β-(4-Methylphenyl)-tropane-2β-tetrazole Hydrochloride (RTI157)

Reaction of 0.12 g (0.5 mmol) of RTI-158 as described above for RTI-163 gave after workup and purification of the crude by flash column chromatography (100% CMA) 0.14 g (88%) of pure tetrazole (RTI-157): $^1$H NMR ($CDCl_3$+1 drop MeOD) δ 1.8 (m, 1 H), 2.14 (s, 3 H), 2.35 (m, 5 H), 2.71 (s, 3 H), 3.36 (m, 1 H), 3.75 (m, 2 H), 4.02 (m, 1 H), 6.48 (d, J=8 Hz, 2 H), 6.82 (d, J=8 Hz, 2 H).

The purified product was converted into HCl salt: $^1$H NMR (MeOD) δ 2.01 (m, 1 H), 2.27 (s, 3 H), 2.69 (m, 5 H), 2.97 (s, 3 H), 3.81 (m, 2 H), 4.18 (m, 2 H), 5.5 (s, 1 H), 6.76 (d, J=8 Hz, 2 H), 7.02 (d, J=8 Hz, 2 H); mp 212\*\*C. (dec); Anal calcd for $C_{16}H_{23}Cl_2N_5.0.25H_2O$; C=53.26, H=6.56 N=19.41; found C=53.41, H=6.50, N=19.02; $[\alpha]_D$ –110.97° (c=0.16, MeOH).

Example 17

3β-(4-Chlorophenyl)-2β-(3-methylisoxazol-5-yl) tropane Hydrochloride (RTI-165)

A solution of n-butyl lithium in hexane 5.9 ml (2.5M. 14.6 mmol) was added to a stirred solution of acetone oxime 0.55 g (7.3 mmol) in dry THF (15 ml) at 0° C. under nitrogen. After 1 hour, a solution of 1.65 g (5.62 mmol) 3β-(4-Chlorophenyl)-2β-(carbomethoxy)tropane in 10 ml dry was added dropwise with stirring at 0° C. The solution was allowed to warm to room temperature over 18 hours. The mixture was poured into a stirred solution of concentrated sulfuric acid (3.2 g) in THF (15 ml) and water (4 ml) and was heated under reflux for 1 hour. The cooled solution was made basic using saturated aqueous $K_2CO_3$ (10 ml) and extracted thrice with 10 ml methylene chloride. The combined organic layers were dried ($Na_2SO4$), filtered and solvent removed in vacuo to give 1.8 g of crude isoxazole. Purification of the crude residue by flash column chromatography (10% CMA in methylene chloride) gave 0.74 g (46%) of pure isoxazole RTI-165 which was further purified by crystallization from methylene chloride/hexane: $^1$H NMR ($CDCl_3$) δ 1.71 (m, 3 H), 2.10 (m, 3 H), 2.18 (s, 3 H), 2.24 (s, 3 H), 3.20 (m, 2 H), 3.32 (m, 2 H), 6.18 (s, 1 H), 6.9 (d, J=8 Hz, 2 H),7.14 (d, J=8, Hz, 2 H); IR ($CCl_4$) 2950, 1590, 1490, 1420, 1350, 1020, 910 $cm^{-1}$; mp 154–156° C.; Anal calcd for $C_{18}H_{21}N_2OCl$; C=68.28, H=6.68, N=8.84, Cl=11.19; found C=68.22, H=6.69, N=8.87, Cl=11.19; $[\alpha]_D$ –125.58° (c=0.43, MeOH).

The isoxazole was crystallized as the hydrochloride salt: $^1$H NMR (MeOD) δ0 2.04 (s, 3 H), 2.19 (m, 1 H), 2.30 (m, 1 H), 2.48 (m, 2 H), 2.60 (m, 1 H), 2.70 (m, 1 H), 2.90 (s, 3 H), 3.68 (m, 1 H), 3.81 (m, 1 H), 4.04 (m, 1 H), 4.15 (m, 1 H), 5.55 (s, 1 H), 7.04 (d, J=8 Hz, 2 H), 7.14 (d, J=8 Hz, 2 H); mp>235° C. (dec); Anal calcd for $C_{18}H_{22}Cl_2N_2O$; C=61.19, H=6.28, N=7.93, Cl=20.07; found c=60.98, H=6.38, N=7.91, Cl=19.96; $[\alpha]_D$ –102.89° (c=0.46, MeOH).

Example 18

3β-(4-Methylphenyl)-2β-(3-methylisoxazol-5-yl) tropane Hydrochloride (RTI-171)

Reaction of 1.09 g (4 mmol) of 3β-(4-Methylphenyl)-2β-(carbomethoxy)tropane as described above for RTI-165 gave after workup 1.21 g crude isoxazole. Purification of the crude by flash column chromatography (15% CMA in methylene chloride) gave 0.73 g (62%) pure isoxazole (RTI-171): $^1$H NMR ($CDCl_3$) δ 1.73 (m, 3 H), 2.11 (m, 3 H), 2.17 (s, 3 H), 2.23 (s, 3 H), 2.25 (s, 3 H), 3.20 (m, 2 H), 3.32 (m, 2 H), 6.13 (s, 1 H), 6.97 (m, 4 H); IR ($CCl_4$) 2935, 2785, 1590, 1510, 1460, 1421, 1350, 1125,1010, 910 $cm^{-1}$.

The isoxazole was crystallized as the hydrochloride salt: $^1$H NMR (MeOD) δ 2.01 (s, 3 H), 2.24 (s, 3 H), 2.32 (m, 2

H), 2.42 (m, 4 H), 2.81 (s, 3 H), 3.61 (m, 1 H), 3.78 (m, 1 H), 4.03 (m, 1 H), 4.15 (m, 1 H), 5.45 (s, 1 H), 6.96 (m, 4 H); mp 277° C.; Anal calcd for $C_{19}H_{25}ClN_2O$; C=68.55, H=7.57, N=8.42, Cl=10.65; found C=68.65, H=7.62, N=8.42, Cl=10.56; $[\alpha]_D$ −107.28° (c=0.71, MEOH).

Example 19

3β-(4-Iodophenyl)-2β-(3-methylisoxazol-5-yl) tropane Hydrochloride (RTI-180)

Reaction of 0.73 g (1.9 mmol) of 3β-(4-Iodophenyl)-2β-(carbomethoxy)tropane as described above for RTI-165 with phenyl acetone oxime gave after workup 0.77 g of crude isoxazole. Purification of the crude by flash column chromatography (5% CMA80 in methylene chloride) gave 0.37 g (49%) of pure isoxazole RTI-180: $^1$H NMR (CDCl$_3$) δ 1.71 (m, 3 H), 2.12 (m, 3 H), 2.18 (s, 3 H), 2.24 (s, 3 H), 3.17 (m, 2 H), 3.33 (m, 2 H), 6.18 (s, 1 H), 6.74 (m, 2 H), 7.49 (m, 2 H) ; IR (CHCl$_3$) 2940, 1600, 1485, 1450, 1420, 1355 cm$^{-1}$.

The isoxazole was crystallized as the hydrochloride salt: $^1$H NMR (MeOD) δ 2.11 (s, 3 H), 2.50 (m, 6 H), 2.89 (s, 3 H), 3.70 (m, 1 H), 3.90 (m, 1 H), 4.14 (m, 1 H), 4.22 (m, 1 H), 5.66 (s, 1 H), 6.96 (m, 2 H), 7.56 (m, 2 H); mp>235° C. (dec); Anal calcd for $C_{18}H_{22}ClIN_2O \cdot 0.25H_2O$ C=48.12, H=5.05, N=6.24, Cl=15.79; I=56.50; found C=47.84, H=5.05, N=6.19, Cl=15.77; I=56.46; $[\alpha]_D$ −94.57° (c=0.39, MeOH).

Example 20

3β-(4-Chlorophenyl)-2β-(3-phenylisoxazol-5-yl) tropane Hydrochloride (RTI-177)

Reaction of 1.18 g (4 mmol) of 3β-(4-Chlorophenyl)-2β-(carbomethoxy)tropane as described above for RTI-165 gave after work up 1.46 g of crude isoxazole. Purification of the crude by flash column chromatography [20% (ether/triethylamine 9:1) in hexane] gave 0.75 g (50%) of pure isoxazole RTI-177 which was further purified by crystallizing from ether/petroleum ether: $^6$H NMR (CDCl$_3$) δ 1.74 (m, 3 H), 2.22 (m, 3 H), 2.27 (s, 3 H), 3.24 (m, 2 H), 3.36 (m, 2 H), 6.80 (s, 1 H), 6.94 (m, 2 H), 7.12 (m,2 H), 7.40 (m, 3 H), 7.76 (m, 2 H); IR (CHCl$_3$) 2940, 1600, 1590, 1490, 1450, 1405, 1350 cm$^{-1}$.

The isoxazole was crystallized as the hydrochloride salt: $^1$H NMR (MeOD) δ 2.35 (m, 6 H), 2.84 (s, 3 H), 3.73 (m, 1 H), 4.09 (m, 1 H), 4.21 (m, 1 H), 6.12 (s, 1 H), 7.14 (m, 4 H), 7.34 (m, 3 H), 7.57 (m, 2 H); mp 287° C.; Anal calcd for $C_{23}H_{24}Cl_2IN_2O \cdot 0.25H_2O$ C=65.79, H=5.88, N 6.67, Cl=16.89; found C=65.94, H=5.79, N=6.68, Cl=17.00; $[\alpha]_D$ −97.5° (c=0.28, MeOH).

Example 21

3β-(4-Methylphenyl)-2β-(3-phenylisoxazol-5-yl) tropane Hydrochloride (RTI-176)

Reaction of 1.09 g (4 mmol) of 3β-(4-Methylphenyl)-2β-(carbomethoxy)tropane as described above for RTI-165 gave after work up 1.56 g of crude isoxazole. Purification of the crude by flash column chromatography [25% (ether/triethylamine 9:1) in hexane] gave 1.1 g (77%) of pure isoxazole RTI-176 which was further purified by crystallizing from methylene chloride/hexane: $^1$H NMR (CDCl$_3$) δ 1.76 (m, 3 H), 2.23 (m, 3 H), 2.24 (s, 3 H), 2.27 (s, 3 H), 3.23 (m, 2 H), 3.36 (m, 2 H), 6.74 (s, 1 H), 6.93 (m, 4 H), 7.41 (m,3 H), 7.76 (m, 2 H); IR (CCl$_4$) 2935, 1590, 1455, 1410, 1215 cm$^{-1}$ The isoxazole was crystallized as the hydrochloride salt: $^1$H NMR (MeOD) δ 2.08 (m, 1 H), 2.15 (s, 3 H), 2.45 (m, 5 H), 2.84 (s, 3 H), 3.68 (m, 1 H), 3.88 (m, 1 H), 4.07 (m, 1 H), 4.22 (m, 1 H), 5.97 (s, 1 H), 7.0 (m, 4 H), 7.33 (m, 3 H), 7.54 (m, 2 H); mp 270–295° C. (dec); Anal calcd for $C_{24}H_{27}ClN_2O$; C=72.99, H=6.89, N=7.10, Cl=8.98; found C=72.91, H=6.91, N=7.15, Cl=8.98; $[\alpha]_D$ −102.22 (c=0.68, MeOH).

Example 22

3β-(4-Iodophenyl)-2β-(3-phenylisoxazol-5-yl) tropane Hydrochloride (RTI-181)

Reaction of 0.73 g (1.9 mmol) of 3β-(4-Iodophenyl)-2β-(carbomethoxy)tropane as described above for RTI-176 gave after workup 1.46 g of crude isoxazole. Purification of the crude by flash column chromatography [20% (ether/triethylamine 9:1) in hexane] gave 0.5 g (56%) of pure isoxazole RTI-181 which was further purified by crystallizing from methylene chloride/hexane: $^1$H NMR (CDCl$_3$) δ 1.72 (m, 3 H), 2.15 (m, 2 H), 2.28 (s, 3 H), 3.22 (m, 2 H), 3.35 (m, 2 H), 6.74 (m, 2 H), 6.79 (s, 1 H), 7.44 (m, 5 H), 7.75 (m, 2 H); IR (CHCl$_3$) 2940, 1580, 1480, 1475, 1450, 1400, 1355, 1005 cm$^{-1}$ The isoxazole was crystallized as the hydrochloride salt: 1 H NMR (MeOD) δ 2.54 (m, 6 H), 2.92 (s, 3 H), 3.79 (m, 1 H), 4.05 (m, 1 H), 4.19 (m, 1 H), 4.33 (m, 1 H), 6.18 (s, 1 H), 7.02 (m, 2 H), 7.43 (m, 3 H), 7.63 (m, 4 H); mp >267° C. (dec); Anal calcd for $C_{23}H_{24}ClIN_2O \cdot 0.5H_2O$ C=53.55, H=4.89, N=5.43, Cl=13.75; I=49.21: found C=53.75, H=4.87, N=5.41, Cl=13.68; I=48.95; $[\alpha]_D$ −91.11° (c=0.43, MeOH).

Example 23

Biochemistry of 3β-(Substituted phenyl)-2β-(heterocyclic)tropanes

Inhibition of radioligand binding data at the dopamine, serotonin, and norepinephrine transporters are listed in Tables II, III and IV.

Example 24

Synthesis and Biological Evaluation of 2,3-Diphenyltropane Stereoisomers

These studes investigate the effect of replacement of the 2β-carbomethoxy group of WIN 35,065-2 with a phenyl group on dopamine transporter binding. In addition to providing SAR information of 2-position modification, a 2-aryl substitution also places the aromatic group two carbons away from the basic tropane nitrogen, which may mimic the spatial relationship between the aromatic ring and the basic nitrogen in DA, 5-HT, and NE. Various stereoisomers of (±)-2,3-diphenyltropanes (3–6) were synthesized and evaluated in competitive binding assays to determine their affinities for the DA, 5-HT, and NE transporters.

Chemistry

Figure 4:
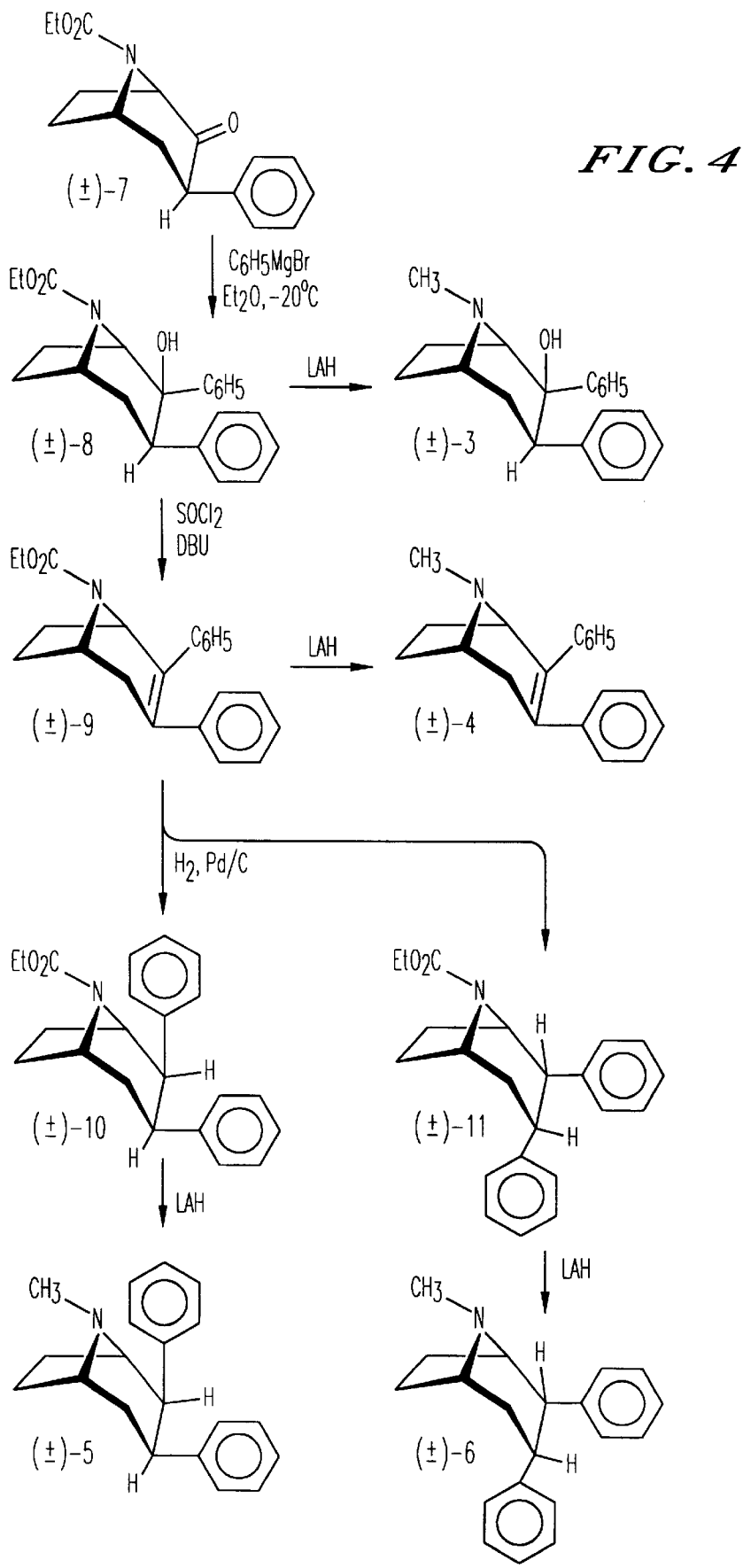
FIG. 4 depicts the synthesis route for compounds 3, 4, 5, 6, 8, 9, 10 and 11 of Example 24.
Figure 5A:
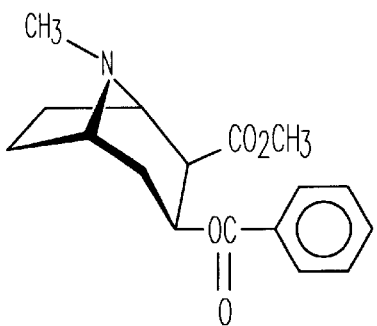
FIG. 5 depicts shows the identity of R groups for compounds 3–6 of Example 24.
Figure 5B:
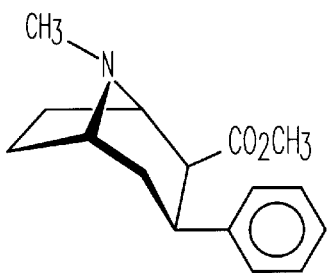
Figure 5C:
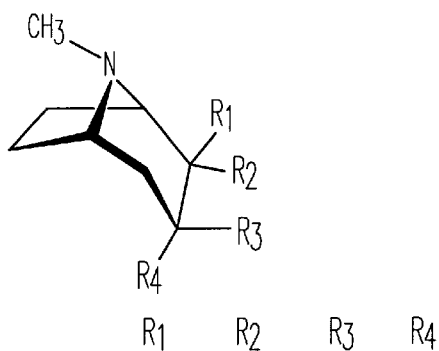

The target compounds were synthesized as racemates from intermediate (±)-7, which was prepared in five steps from 3-tropinone via a reported synthesis. (Daum et al, *J. Med. Chem.* 1973, 16, 667–670; Lyle et al, *J. Org. Chem.* 1970, 35, 802–805.) Treatment of (±)-7 with phenylmagnesium bromide produced intermediates 8 (FIG. 4). Reduction of the ethoxycarbonyl group in 8 with lithium aluminum hydride yielded target compound 3. Alternatively, intermediate 8 was dehydrated to produce 9, which was found to readily undergo a photochemical reaction, presumably cyclizing to form a phenanthrene derivative. However, compound 9 could be reduced to target compound 4 or hydrogenated before lithium aluminum hydride reduction to generate compounds 10 and 11. This route resulted in the synthesis of 2α,3β-diphenyl (3), 2β,3β-diphenyl (5), and 2α,3α-diphenyltropanes (6) as well as 2,3-diphenyltrop-2-ene (4) (FIGS. 4 and 5).

The structures of the compounds were established using vicinal coupling constants obtained from $^1$H NMR spectra combined with 2-D high-field NMR experiments (COSY, NOESY, and HMQC). The stereochemistry of 5 was assigned the 2β,3β stereochemistry based on the large diaxial coupling ($J^3$=13.0 Hz) between H3 and H4β and $J^3$=6.6 Hz coupling between H3 and H2. Further confirmation of this stereochemistry is obtained from the NOESY interactions between H3α and H6 and between H2α and H7. The 3α stereochemistry of 6 is based on the smaller diaxial coupling constant to H4β. The 2α stereochemistry is more difficult to ascertain. Neither the coupling of H2 to H3 or to H1 is diagnostic of the stereochemistry. However, the NOESY spectrum of 6 showed a through space NOE interaction between H4β and H2 fixing H2 as axial. The large diaxial coupling constant ($J^3$=14.1 Hz) between H3 and H4β established the stereochemistry of 3 as 2α,3β. The stereochemistry of the 2-phenyl can be determined based on the NOESY interaction with H7 showing that the 2-phenyl group must be equatorial.

Biology

The binding affinities of the compounds for the dopamine transporter, the serotonin transporter, and the norepinephrine transporter were determined via competitive binding assays using previously reported procedures. (Carroll et al, *J. Med. Chem.* 1993, 36(20), 2886–2890.) The radioligands used were 0.5 nM [$^3$H]WIN35,428 for the DA transporter, 0.2 nM [$^3$H]paroxetine for the 5-HT transporter, and 0.5 nM [$^3$H] nisoxetine for the NE transporter.

The binding affinities of compounds 1, 2 and 3–6 are listed in Table V. The 2β,3β-diphenyl isomer 5 with an $IC_{50}$ value of 28 nM was the most potent at the DA transporter. The 2α,3β-diphenyl isomer 3 and the 2α,3α-diphenyl isomer 6 were found to have poor affinity for the cocaine binding site on the DA transporter, with $IC_{50}$ values of 2.9 and 1.3 μM, respectively.

The presently reported results provide additional information that a 2β-carbomethoxy group is not necessary for high affinity binding at the cocaine binding site on the DA transporter. Furthermore, the present results indicate that a phenyl ring can substitute for the 2β-carbomethoxy group in WIN 35,065-2 without loss in binding affinity. The high potency of the 2β,3β isomer relative to the 2α,3β and 2α,3β isomers is also consistent with other cocaine analogues bearing substituents at both C-2 and C-3 positions of the other tropane systems. (Carroll et al, *J. Med. Chem.* 1994, 37, 2865–2873; Carroll et al, *J. Med. Chem.* 1992, 35, 969–981; Boja et al, *J. Med. Chem.* 1994, 37(8), 1220–1223; Kozikowski et al, *J. Med. Chem.* 1994, 37, 3440–3442; Meltzer et al, *J. Med. Chem.* 1994, 37, 2001–2010; Newman et al, *J. Med. Chem.* 1994, 37, 2258–2261; Davies et al, *J. Med. Chem.* 1994, 37, 1262–1268; Kotian et al, *J. Med. Chem.* 1996, 39(14), 2753–2763; Carroll et al, *J. Med. Chem.* 1993, 36(20), 2886–2890; Carroll et al, *J. Med. Chem.* 1995, 38, 379–388; Kozikowski et al, *J. Med. Chem.* 1995, 38, 3086–3093; Kelkar et al, *J. Med. Chem.* 1994, 37, 3875–3877; Kozikowski et al, *J. Med. Chem.* 1992, 35, 4764–4766.)

In view of the racemic nature of the compounds reported in this study, it can be concluded that (±)-5 and (R)-2 bind the DA transporter with equal affinity. However, 5 appears to exhibit greater selectivity for the DA transporter over the 5-HT and NE transporters than 2. This is consistent with previous studies which found that 3β,3-(4'-methylphenyl)- and 3β-(4'-chlorophenyl)tropane-2β-carboxylic acids phenyl esters retained DA transporter binding affinity similar to their corresponding methyl esters while showing significantly improved DA transporter selectivity. (Carroll et al, *J. Med. Chem.* 1995, 38, 379–388.) These results suggest that an aromatic ring C-2 substituent may be an important contributing factor to binding at the DA transporter. Furthermore, this interaction may be unique to the DA transporter, thus conferring greater selectivity to those cocaine analogues which contain aromatic groups at the C-2 position.

While not intending to be bound by theory, a possible explanation for the wide range of substituents that can be accommodated at the C-2 position of the tropanes is the existence of several different binding modes for the C-2 group. While the β-orientation of the C-2 group is required, C-2 substituents may be capable of interacting with the DA transporter binding site via an electrostatic/hydrogen-bonding or hydrophobic process depending on the nature of the C-2 group. Moreover, the results obtained with cocaine analogues bearing aromatic heterocycles at the C-2 position (Kotian et al, 1996; Carroll et al, 1993) suggest that the hydrogen bonding or electrostatic interactions predominate over hydrophobic interactions when both types of interactions are possible for the 2β-substituent. For cocaine analogues bearing 2β-heterocycles, a high correlation was found between molecular electrostatic potential (not hydrophobicity) and binding potency. (Kotian et al, 1996.)

Because 4'-substitution of the 3β phenyl ring significantly enhances the biological activity of cocaine analogues, (Carroll et al, 1994; Carroll et al, 1992; Boja et al, 1994; Kozikowski et al, 1994; Meltzer et al, 1994; Newman et al, 1994; Davies et al, 1994; Kotian et al, 1996; Carroll et al, 1993; Carroll et al, 1995; Kozlkowski et al, 1995; Kelkar et al, 1994; Kozikowski et al, 1992) preparation of 5 in optically pure form via either resolution or stereoselective synthesis and substitutions of the 2- and 3-phenyl rings should both improve binding affinity and selectivity for the dopamine transporter.

Experimental

Elemental analysis were conducted by Atlantic Microlab, Inc in Norcross, Georgia. [$^3$H]3β-(p-Fluorophenyl)tropane-2β-carboxylic acid methyl ester ([$^3$H]WIN 35,428) and [$^3$H]paroxetine were purchased from DuPont-New England Nuclear (Boston, Mass.). [$^3$H]Nisoxetine was purchased from American Radiolabeled Chemicals, Inc. (St. Louis, Mo.). When anhydrous conditions were required, solvents were distilled and dried by standard techniques immediately prior to use. All air and moisture sensitive reactions were conducted under a prepurified nitrogen atmosphere in oven-dried glassware at 115° C. Routine NMR spectra were obtained on a Bruker AM-250 spectrometer. COSY, NOESY, and HMQC spectra were recorded on a Bruker AMX-500 spectrometer operating at 500.13 MHz for $^1$H using, a Bruker 5 mm inverse detect broadband probe. The double quantum filtered phase sensitive COSY (Shaka et al, *J. Magn. Reson.* 1983, 51, 169–173; Derome et al, *J. Magn. Reson.* 1990, 88, 177–185) and NOESY (States et al, *J. Magn. Reson.* 1982, 48, 286–292) were acquired as 1024× 512 data points with a spectral width of 4800 Hz in both dimensions. The data were apodized with a squared sine function and zero filled to 2K×2K data points prior to Fourier transformation. NOESY spectra were obtained with a 1200 msec mixing time and a recycle delay of 4 sec. Heteronuclear multiple quantum correlation (HMQC)(Bax et al, *J. Magn. Reson.* 1986, 67, 565–569) spectra were acquired as 1024×256 data points with a spectral width of 4800 Hz in F2 and 24375 Hz in F1. An average coupling constant of 145 Hz was used to optimize $1/J_{CH}$ delays. The data were apodized with a squared sine function and zero filled to 2048×512 data points prior to Fourier transformation.

(±)-8-Ethoxycarbonyl-2α-phenyl-3β-phenyl-nortropan-2β-ol (8). With stirring at −20° C. (salt-ice), 3.0M PhMgBr in $Et_2O$ (1.9 mL, 5.8 mmol) was added dropwise over 4 min to a solution of (±)-7 (Daum et al, 1973; Lyle et al, 1970) (1.0567 g, 3.866 mmol) in dry $Et_2O$ (20 mL), and the mixture was stirred at −20° C. under Ar. After 15 min, more cold $Et_2O$ (5 mL) was added to rinse down the flask walls. After 1 h, the mixture was quenched with $Et_2O$ (30 mL) and $H_2O$ and was stirred at room temperature for 30 min. The mixture was then partitioned between $Et_2O$ (150 mL) and $H_2O$ (50 mL), and the organic fraction was washed with brine before it was dried ($Na_2SO_4$), filtered through celite, and evaporated. The crude product was purified by flash column eluting with hexane/30% $Et^2O$ to yield 0.8509 g of 8 (63%): $^1H$ NMR ($CDCl_3$) δ 1.33 (t,J=7.0 Hz, 3H, $CH_3$), 1.74–1.82 (m, 2H, H7 and H4α), 1.86–1.91 (m, 1H, H6), 1.97–2.08 (m, 2H, H7 and H6), 2.35–2.40 (ddd, J=3.0 Hz, 13.0 Hz, 13.0 Hz, 1H, H4β), 3.2 (br s, 1H, OH), 3.61 (dd, J=12.5 Hz and 5.5 Hz, 1H, H3α), 4.24 (q, J=7.0 Hz, 2H, —$OCH_2$), 4.27 (m, 1H, H1), 4.5 (br s, 1H, H5), 7.10 (tt, J=7.0 Hz and 1.0 Hz, 1H, H4"), 7.2 (m, 3H, H3", H5", and H4'), 7.27 (t, J=8.0 Hz, 2H, H3' and H5'), 7.39 (d, J=8.0 Hz, 2H, H2" and H6"), 7.53 (dd, J=8.0 Hz and 1.0 Hz, 2H, H2' and H6'); $^{13}C$ NMR ($CDCl_3$) δ 14.7 ($CH_3$), 24.8 (C7), 27.0 (C6), 36.9 (C4), 41.1 (C3), 53.6 (C5), 61.5 ($OCH_2$), 65.5 (C1), 78.9 (C2, observed only when spectrum was recorded in a mixture of $CD_3OD$ and $CDCl_3$), 126.4 (C4"), 126.9 (C2' and C6'), 127.0 (C4'), 127.89 and 127.92 (C3', C5' and C3", C5"), 130.1 (C2", C6"), 140.3 and 143.0 (C1' and C1"), 156.1 (CO); MS (EI) m/z 351.20. Elemental ($C_{22}H_{25}NO_3$) calcd. C=75.18, H=7.17, N=3.99; found C 74.99, H=7.22, N=3.94.

(±)-2α,3β-Diphenyl-tropan-2-ol (3). With stirring at room temperature under Ar, a solution of 8 (0.1129 g, 0.321 mmol) in dry $Et_2O$ (3×1 mL) was added to 1.0M solution of LAH in $Et_2O$ (0.96 mL, 0.96 mmol), and the mixture was heated to reflux with stirring under $N_2$. After 2 h, the mixture was diluted with $Et_2O$ (8 mL) and quenched with a few drops of saturated $NaHCO_3$. The mixture was filtered through celite, and the filter cake was washed thoroughly with $Et_2O$. The combined filtrate was washed with saturated $NaHCO_3$ and brine before it was dried ($Na_2SO_4$), filtered through celite, and evaporated. The crude product was purified by radial PLC on 1 mm silica gel plates eluting with $CHCl_3$/2.5% MeOH/0.25% $NH_4OH$. The free base was converted to the HCl salt with 1.0M HCl in $Et_2O$ to yield 0.0747 g of 3.HCl (70%): mp (HCl salt)>250° C. dec; $^1H$ NMR ($CDCl_3$, free base) δ 1.65–2.20 (complex, 6H, 3 $CH_2$) 2.29 (s, 3H, $NCH_3$), 2.89 (in, 1H, CH), 3.16 (m, 1H, CH), 3.3 (dd, J=12.5 Hz and 5.3 Hz, 1H, CH), 5.44 (br s, 1H, OH), 6.9–7.2 (m, 6H, aromatic), 7.41 (d, J=7.0 Hz, 2H, aromatic), 7.49 (d, J=7Hz, 2H, aromatic); $^{13}C$ NMR ($CDCl_3$, free base) δ 21.78, 24.87, 39.44, 40.47, 41.55, 61.26, 75.81, 76.29, 125.93, 126.53, 126.88, 127.77 (overlap of two carbon peaks?), 130.17, 141.88, 143.57; MS (EI) m/z 293.25. Elemental ($C_{20}H_{23}NO.HCl.0.75H_2O$) calcd. C=69.96, H=7.49, N=4.08; found C=70.08, H=7.13, N=4.02.

(±)-8-Ethoxycarbonyl-2,3-diphenyl-nortrop-2-ene (9). With stirring at 0° C. under $N_2$, $SOCl_2$ (0.79 mL, 10.8 mmol) was added to a mixture of 8 (0.7619 g, 2.168 mmol) and DBU (3.2 mL, 21.7 mmol) in dry $CH_2Cl_2$ (40 mL), and the mixture was stirred at 0° C. under $N_2$. After 1.5 h, more DBU (3.2 mL, 21.7 mmol) and $SOCl_2$ (0.79 mL, 10.8 mmol) were added with stirring at 0° C. under $N_2$. After 1 h, the mixture was quenched with $H_2O$ (10 mL) and was then partitioned between $Et_2O$ (500 mL) and $H_2O$. The organic fraction was washed repeatedly with $H_2O$ until the organic fraction was nearly colorless. The organic fraction was then washed with brine before it was dried ($Na_2SO_4$), filtered through celite, and evaporated. The crude product was purified by flash column eluting with hexane/10% $Et_2O$ to yield 0.6283 g of 9 (87%): $^1H$ NMR ($CDCl_3$, free base) δ 1.31 (br S, 3H, $CH_3$), 1.82–3.10 (br m, 6H, 3 $CH_2$), 4.21 (q, J=7.0 Hz, 2H, $OCH_2$), 4.52 (br s, 1H, CH), 4.72 (br s, 1H, CH), 6.9–7.2 (m, 10H, aromatic); $^{13}C$ NMR ($CDCl_3$, free base) δ 14.87, 30.59 (d), 33.81 (d), 38.77 (d), 52.95, 58.62, 61.08, 126.46, 126.63, 127.79, 128.02, 128.96, 129.49, 130.74 (d), 139.84, 140.83, 141.45 (d), 154.93; MS (EI) m/z 333.40. Elemental ($C_{22}H_{23}NO_2$) calcd. C=79.25, H=6.95, N=4.20; found C=79.22, H=6.99, N=4.16.

NOTE: Compound 9 readily undergoes a photochemical reaction when exposed to UV radiation.

(±)-2,3-Diphenyl-trop-2-ene (4). Compound 4 was prepared from 9 (0.1121 g, 0.336 mmol) and 1.0M LAH in $Et_2O$ (1.01 mL, 1.01 mmol) using conditions similar to those for the preparation of 3. The crude product was purified by flash column chromatography eluting with $CHCl_3$/5% NeOH/0.5% $NH_4OH$. The free base was converted to the HCl salt with 1.0M HCl in $Et_2O$ to yield 0.1063 g of 4.HCl (100%) after evaporation from a mixture of hexane and $CH_2Cl_2$: mp (HCl salt) 102° C. dec; $^1H$ NMR ($CDCl_3$, free base) δ 1.7–2.4 (complex, 5H), 2.58 (s, 3H, $NCH_3$), 2.78 (dd, J=18.0 Hz and 4.0 Hz, 1H, H4), 3.44 (m, 1H, CH), 3.65 (mm, 1H, CH), 6.9–7.2 (m, 10H, aromatic); $^{13}C$ NMR ($CDCl_3$, free base) δ 30.35, 33.59, 36.17 (br s, overlap of two peaks?), 58.19, 65.21, 126.25, 127.78, 127.94, 128.88, 129.30, 130.13, 138.54, 141.22 (not all $sp^2$ carbons were observed due to overlap of peaks); MS (EI) mlz 275.30. Elemental ($C_{20}H_{21}N.HCl.0.75H_2O$) calcd. C=73.83, H=7.28, N=4.30; found C=74.04, H=7.25, N 4.25.

(±)-8-Ethoxycarbonyl-2β,3β-diphenyl-nortropane-8-carboxylate (10) and (±)-Ethyl-2α,3α-diphenyl-nortropane (11). A mixture of (±)-9 (0.0602 g, 0.1806 mmol) and 10% Pd/C (31 mg) in MeOH (4 mL) was hydrogenated at room temperature under 50 psi. The hydrogen pressure was raised to 50 psi as needed. After 5 days, the mixture was filtered throuah celite, and the Pd/C was washed with MeOH (120 mL). The combined filtrate was evaporated to dryness to yield a mixture of (±)-10 and (±)-11, which were separated by radial PLC on 1 mm silica gel plates eluting with hexane/10% $Et_2O$ to yield the more polar (±)-10 (37.5 mg, 62%) and the more nonpolar (±)-11 (18.7 mg, 31%).

(±)-8-Ethoxycarbonyl-2β,3 β-diphenyl-nortropane (10). $^1H$ NMR ($CDCl_3$) δ 0.841.25 (2 br s, 3H, $CH_3$), 1.82–2.67 (complex, 6H, 3 $CH_2$), 3.17 (br s, 1H, CH), 3.58–3.78 (complex, 3H, 1 CH and $OCH_2$), 4.50 (br s, 1H, CH), 4.74 (br s, 1H, CH), 6.99–7.11 (in, 10H, aromatic). Anal. ($C_{22}H_{25}NO_2.0.25H_2O$) calcd. C=77.73, H=7.56, N=4.12; found C=77.94, H=7.54, N=4.10.

(±)-8-Ethoxycarbonyl-2α,3α-diphenyl-nortropane (11). $^1H$ NMR ($CDCl_3$) δ 1.30 (t, J 7.0 Hz, 3H, $CH_3$), 1.59–2.71 (complex, 6H, 3 $CH_2$), 3.52 (m, 1H, CH), 4.03 (m, 1H, CH), 4.20 (q, J=7.0 Hz, 2H, $OCH_2$), 4.49 (m, 1H, CH), 4.68 (m, 1H, CH), 6.96–7.21 (m, 10H, aromatic). Anal. ($C_{22}H_{25}NO_2$) calcd. C=78.77, H=7.51, N=4.18; found C=78.65, H=7.54, N=4.23.

(±)-2β,3β-Diphenyltropane (5). Compound 5 was prepared from (±)-10 (0.218 g, 0.65 mmol) and 1.0M LAH in $Et_2O$ (1.9 ml) using conditions similar to those for the preparation of 4. The crude product was purified by radial PLC on 2 mm silica gel plates eluting with $CHCl_3$/2.5% MeOH/0.25% $NH_4OH$. The product fractions were dried ($Na_2SO_4$), filtered through celite, and evaporated. Once concentrated, the product solution was filtered through a cotton plugged pipette and evaporated to yield 0.16 g (90%) of (±)-5, which was converted to the HCl salt with 1.0M HCl in $Et_2O$: mp (HCl salt) 140° C. dec; $^1H$ NMR (free base, $CDCl_3$) δ 1.65 (ddd, J=13.0 Hz, 4.0 Hz, 4.0 Hz, 1H, H4α), 1.75–1.83 (m, 2H, H6 and H7), 2.13 (in, 1H, H6), 2.24 (s, 3H, $NCH_3$), 2.28 (m, 1H, H7), 2.39 (ddd, J=13.0 Hz, 13.0 Hz, 2.6 Hz, 1H, H4β), 2.88 (dd, J=6.6 Hz, 2.4 Hz, 1H, H2), 3.31 (ddd, J=13.0 Hz, 6.6 Hz, 4.0 Hz, 1H, H3), 3.35 (m, 1H, H1), 3.40 (m, 1H, H5), 6.84–7.40 (complex, 10H, aromatic); $^{13}C$ NMR (free base, $CDCl_3$) δ 25.0 (C6), 27.3 (C7), 35.2 (C4), 37.4 (C3), 42.0 ($NCH_3$), 53.2 (C2), 61.9 (C5), 67.7 (C1), 125.4 (aromatic), 125.5 (aromatic), 127.0 (aromatic), 127.5 (aromatic), 128.0 (aromatic), 130.6 (aromatic), 142.8 (aromatic), 143.2 (aromatic). Anal. ($C_{20}H_{23}N.0.5H_2O$) calcd. C=74.40, H=7.80, N=4.34; found C=74.17, H=7.88, N=4.25.

(±)-2α,3α-Diphenyltropane (6). Compound 6 was prepared from (±)-11 (0.093 g, 0.28 mmol) and 1.0M LAH in $Et_2O$ (0.83 mL) using conditions similar to those for the preparation of 3. The crude product was purified by radial PLC on 1 mm silica gel plates eluting with $CHCl_3$/5% MeOH/0.5% $NH_4OH$. The product fractions were dried ($Na_2SO_4$), filtered through celite, and evaporated. Once concentrated, the product solution was filtered through a cotton plugged pipette and evaporated to yield 60.9 mg (79%) of (±)-6, which was converted to the HCl salt with 1.0M HCl in $Et_2O$: mp (HCl salt) 249–250° C.; $^1H$ NMR (free base, $CDCl_3$) δ 1.45 (m, 1H, H6), 1.79–1.94 (m, 2H, H7), 2.03 (m, 1H, H6), 2.09 (ddd, J=14.1 Hz, 6.2 Hz, 2.5 Hz, 1H, H4α,β), 2.35 (s, 3H, $NCH_3$), 2.64 (ddd, J=14.1 Hz, 8.0 Hz, 8.0 Hz, 1H, H4β), 3.30 (m, 1H, H5), 3.55 (m, 1H, H1), 3.81 (ddd, J=8.0 Hz, 8.0 Hz, 6.2 Hz, 1H, H3), 3.98 (dd, J=8.0 Hz, ddd, J=14.1 Hz, 8.0 Hz, 8.0 Hz, 5.0 Hz, 1H. H2), 6.92–7.17 (complex 10H, aromatic); $^{13}C$ NMR (free base, $CDCl_3$) δ 22.57 (C7), 27.23 (C6), 36.87 (C3), 37.11 (C4), 40.70 ($NCH_3$), 49.39 (C2), 60.45 (C5), 64.28 (C1), 124.8 (aromatic), 125.5 (aromatic), 127.2 (aromatic), 127.9 (aromatic), 128.3 (aromatic), 128.4 (aromatic), 142.7 (aromatic), 144.0 (aromatic). Anal. ($C_{20}H_{23}N.HCl.0.5H_2O$) calcd. C=74.40, H=7.80, N=4.34; found C=74.22, H=7.55, N=4.26.

Example 25

Figure 6A:
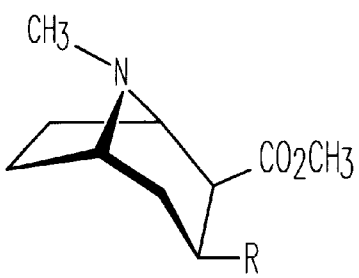
FIG. 6 shows the synthesis of the four possible isomers of (1R)-3(phenylthio)tropane-2-carboxylic acid methyl ester (13a–d) of Example 25.
Figure 6B:
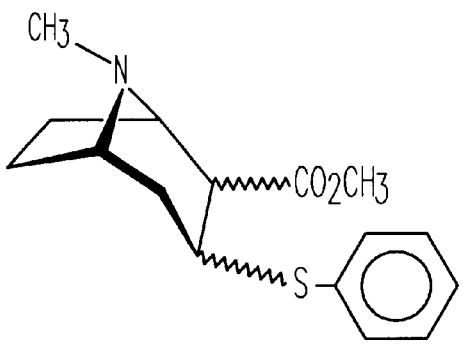

Synthesis of the Isomers of (1R)-3-(Phenylthio) tropane-2carboxylic Acid Methyl Ester-A New Class of Ligands for the Dopamine Transporter In this study, the synthesis of the four possible isomers of (1R)-3(phenylthio)tropane-2-carboxylic acid methyl ester (13a–d) is described (FIG. 6). Compound 13a has the same stereochemistry as 12b and differs from 12b by having a sulfur atom between the 3β-phenyl group and the tropane ring system.

Figure 7A:
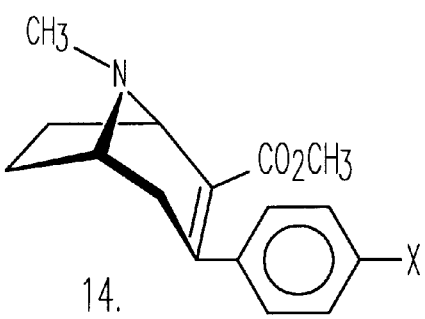
FIG. 7 shows the effect of samarium iodide reduction of tropene 14 to compund 15 of Example 25.
Figure 7B:
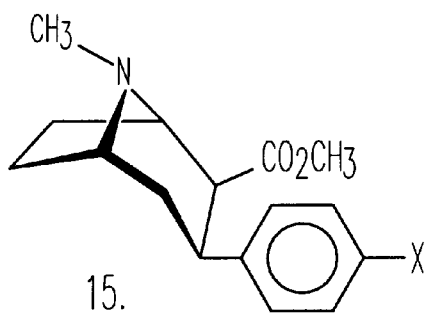
Figure 8:
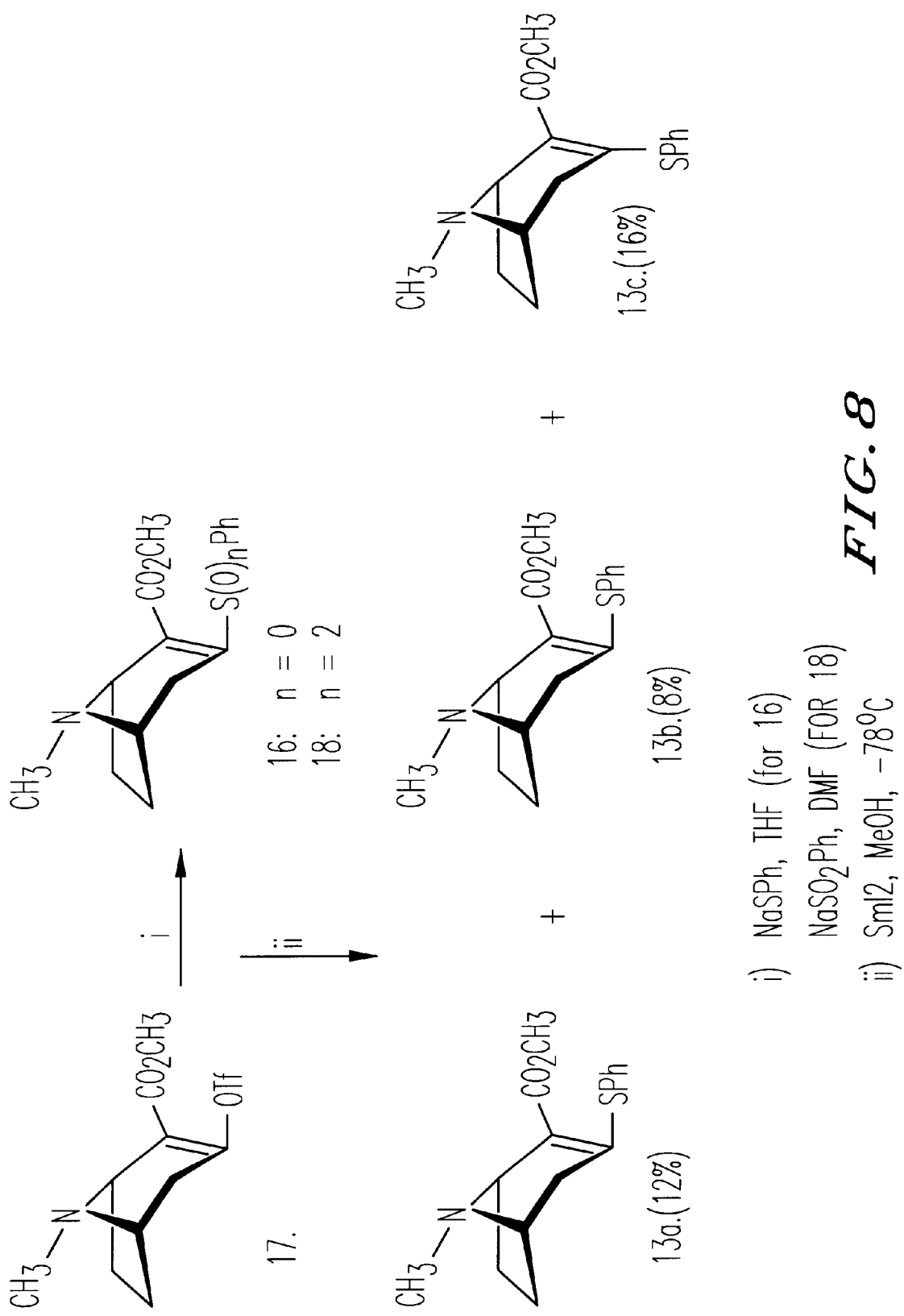
FIG. 8 shows the synthesis of compounds 13a, 13b, 13c, 16 and 18 of Example 25.

Samarium iodide reduction of tropene 14 (FIG. 7) provides a new synthesis of 15 (Keverline et al, *Tetrahedron Lett.*, 1995, 36, 3099.) This result suggested that the synthesis of (1R)-3-(phenylthio)-2-tropene-2-carboxylic acid methyl ester (16) followed by its reduction with samarium iodide (Keverline et al, 1995; Girard et al, *J. Am. Chem. Soc.*, 1980, 102, 2693) might afford the 2β,3β-isomer 13a. Treatment of (1R)-3-(trifluoromethanesulfonyloxy)-2-tropene-2-carboxylic acid methyl ester (17) (Keverline et al, 1995) with the sodium salt of thiophenol in THF gave 16 in 86% yield (FIG. 8). (Crowell et al, *J. Med. Chem.*, 1989, 32, 2436.) To Applicants' knowledge, this is the first example of addition-displacement reaction of a triflate with phenylthiolate thus providing an entry into vinylic sulfide. The sodium salt of benzenesulfinic acid displaced the triflate from 17 to afford the 3-(phenylsulfonyl)-2-tropene-2-carboxylic acid methyl ester (18) in 78% yield. At −78° C., slow, syringe-pump addition of a methanolic solution of 16 to samarium iodide in THF gave a mixture of 13a (12%), 13b (8%), and 13c (16%). None of the 2α,3α-isomer (13d) was produced. Flash column chromatography (Still et al, *J. Org. Chem.*, 1978, 43, 2923) was used to separate 13b from 13a and 13c. The 13a and 13c isomers were separated by HPLC on a silica gel column using 5% of 1% $Et_3N$/i-PrOH in hexanes as the eluent system. The desired isomer 13a had mp 55–57° C. (fusion) and $[\alpha]_D$ −83.19 (c0.47, MeOH) for its (+)-tartrate salt. The (+)-tartrate salt of compound 13b had mp 143–144° C. and $[\alpha]_D$ +49.9 (c0.22, MeOH), and 13c (+)-tartrate had mp 53–58° C. (fusion) and $[\alpha]_D$ of −37.17° (c 0.955, MeOH).

Figure 9:
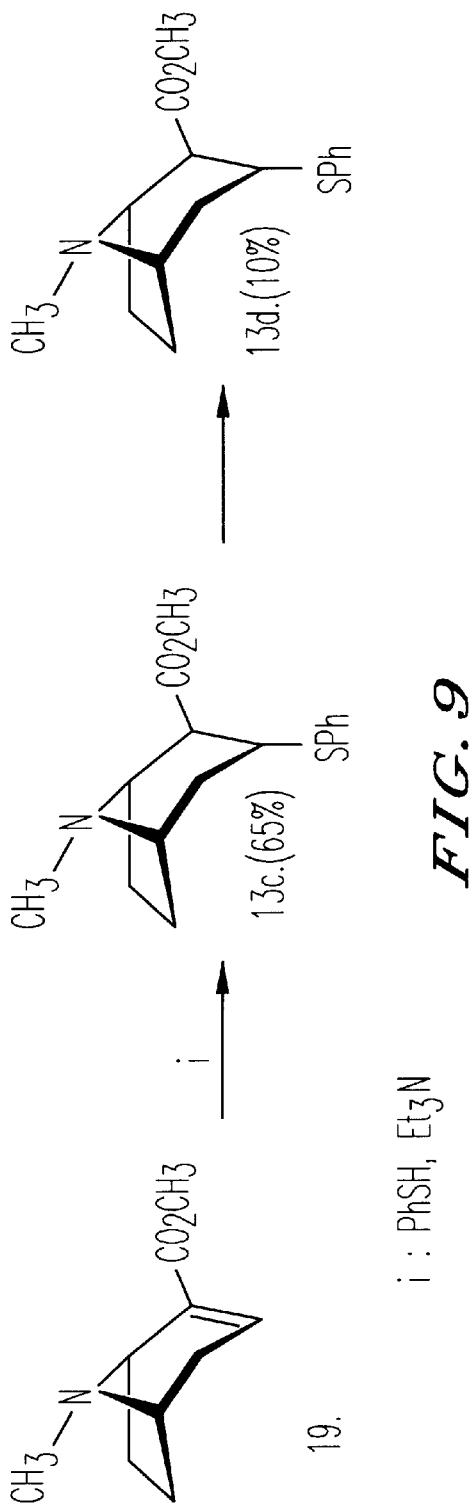
FIG. 9 shows the synthesis of compounds 13c and 13d of Example 25.

The 2α,3α isomer 13d was prepared as shown in FIG. 9. Nucleophilic addition of thiophenol to anhydroecgonine methyl ester (19) in the presence of $Et_3N$ gave, after 24 h, the 2β,3α isomer 13c and 2α,3α isomer 13d in 65 and 10% yields, respectively. Compound 13d had mp 179–180° C. and an $[\alpha]_D$ of +60.4° (c 0.106, MeOH) for its hydrochloride salt. Reaction times of several days affords a 1.2:1 ratio of 13c:13d in 75% overall yield. In either case, the nucleophile shows complete preference for an α-face attack on 19, possibly due to steric hindrance provided by the N-methyl group. The formation of two products may be a consequence of complete facial bias during protonation of the intermediate enol-ester to give 13c followed by partial base-catalyzed epimerization of H-2 to afford 13d. Again, the base-catalyzed epimerization of 13c at C-2 could be forced by an unfavorable steric repulsion between the N-methyl and the 2-carboxymethyl group. Basic conditions encourage facile elimination of thiophenol from 13d to give 19. None of 13a or 13b isomers was observed in the above reaction when the sodium salt of thiophenol was replaced by the lithium or magnesium salts.

Figure 10:
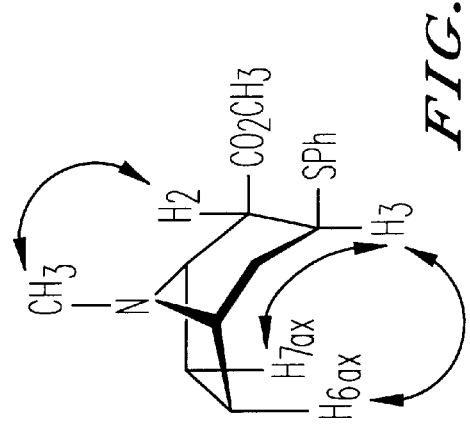
FIG. 10 shows a chair conformation for compound 25 of Example 25 with the H-2 and H-3 in diaxial positions.

Two dimensional NMR experiments, COSY and HETCOR, aided in chemical shift assignments, while the 'J' values and NOESY experiments were used to decipher the stereochemical relationship about C-2 and C-3 substituents in the 13a–d isomers. For example, 13b has a large $J_{2,3}$ value of 12.0 Hz, expected for their antidisposition. On the contrary, $J_{2,3}$ for 13a, 13c and 13d, were 5.2, 1.1 and 6.9 Hz, respectively. Most importantly, H-2 in 13b showed an NOE with N-Me and H-4$_{ax}$, while H-3 showed an NOE with H-6$_{ax}$, and H-7$_{ax}$. The observed NOE results are possible only if 25 exists in a chair conformation with H-2 and H-3 in diaxial positions (FIG. 10). Using similar arguments, 13a, 13c, and 13d were shown to possess the relative stereochemistry and conformation as displayed in their corresponding structures. It was also interesting to note that the proton spectra of 13a–d resembles those of the corresponding cocaine isomers.[8]

Binding data on 13a–13d revealed that the 2β,3β isomer 13a was the most potent ($IC_{50}$ 14.3 nm dm$_{-3}$) at the cocaine binding site of the dopantine transporter. The other isomers, 13c ($IC_{50}$, 183 $nmdm^{-3}$), 13d ($IC_{50}$ 222 $nmdm^{-3}$), and 13b ($IC_{50}$ 613 $nmdm^{-3}$), were only moderately potent. It is interesting to note that 13a is slightly more potent than the lead compound, WIN 35065-2 ($IC_{50}$ 23 $nmdm^{-3}$). Since substitution of the phenyl group of the WIN 35,065-2 series was found to increase potency (Carroll et al, in press), substituted phenyl analogs of 13a, and even 13c–d may be more potent.

Example 26

3-(Phenylthio)-2-tropene-2-carboxylic acid methyl ester

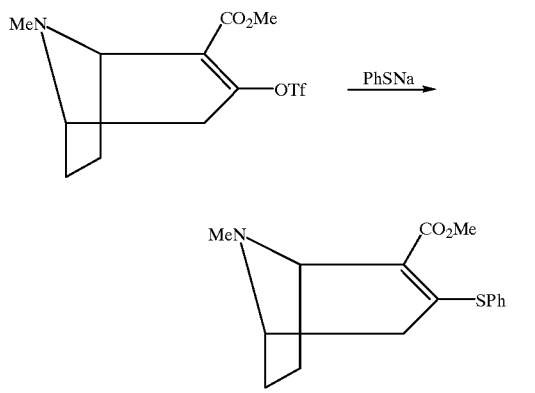

Thiophenol (2 mL 2.13 g, 19.4 mmol) was added to a 0° C. suspension of NaH (60% dispersion in mineral oil, 800 mg, 20 mmol) in dry THF (30 mL) and stirred for 10 min at the same temperature. The resultant thiolate was then added dropwise to a 0° C. solution of 2(carbomethoxy)-3-(trifluoromethansulfonyl)-2-tropene (5.54 g, 17.6 mmol) in dry THF (200 mL). The reaction mixture was stirred at 0° C. solution for 1 h and at 0–5° C. for 1 h. TLC (5% $Et_3N/Et_2O$) indicated complete consumption of starting maternal and the appearance of a more polar spot. Water (20 mL) was added. The mixture was concentrated on a rotary evaporator and the residue diluted with water (100 mL). The aqueous layer was saturated with ammonium chloride and extracted with $Et_2O$ (3×30 mL). The combined organic layers was dried ($Na_2SO_4$), decanted and concentrated to afford a residue which was purified by flash chromatography to give the title compound as a white solid (4.27 g, 86%).

Analytical data: TLC (5% $Et_3N/Et_2O$; $R_f$: 0.29); m pt: 73–74° C. $^1H$ NMR ($CDCl_3$) 7.55–7.43 (m, 5 H), 3.92 (m, 1 H), 3.8 (s, 3 H), 3.13 (m, 1 H), 2.39–2.20 (m which contains a singlet for the N-Me 4 H), 2.09–2.04 (m, 2 H), 1.89–1.81 (m, 1 H), 1.53 (m 1 H), 1.45–1.35 (m, 1 H).

$^1H$ NMR ($C_6D_6$) 7.52–7.40 (m, 2 H), 7.03–6.90 (m 3 H), 4.08 (d, j=6.7 Hz, 1 H), 3.50 (s, 3 H), 2.76 (m, 1 H), 2.47–2.37 (m, 1 H), 2.29 (s, 3 H), 2.20–2.02 (m, 1 H), 1.92–1.78 (m, 2 H), 1.50–1.43 (2 br singlets, 1 H), 1.27–1.14 (m, 1 H).

$^{13}C$ ($CDCl_3$) 166.51, 148.67, 136.18, 130.89, 129.29, 129.00, 123.99, 60.29, 57.63, 51.53, 36.49, 36.10, 34.00, 29.50.

An hydrochloride salt was made and crystallized from Methanol/EtOAc. Anal calcd. for $C_{16}H_{20}NO_2S\cdot HCl$: C, 58.97; H, 6.19; S, 9.84; N, 4.30. Found: C, 59.08; H, 6.24; S, 9.79; N, 4.33.(J. Org. Chem. 54, 4962–4966 (1989)).

Example 27

Synthesis of 3α-(phenylthio)tropane-2β-carboxylic Acid

Methyl Ester and 3α-(phenylthio)tropane-2α-carboxylic Acid Methyl Ester

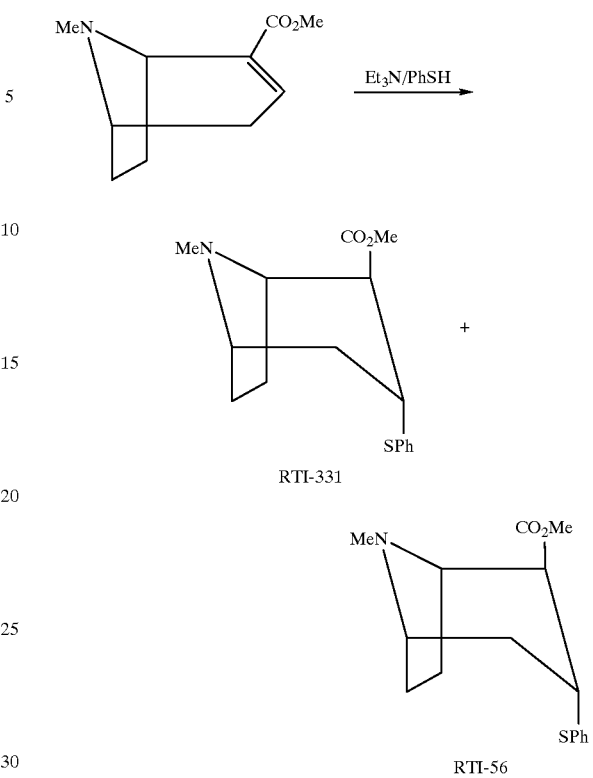

A nitrogen purged 0° C. solution of methylester of anhydroecgonine (2.008 g, 11.08 mmol) and thiophenol (2.9 mL, 3.05 g, 27.7 mmol) in chloroform (100 mL) was treated with $Et_3N$ (0.55 mL) and stirred at room temperature for 24 h. The mixture was then concentrated on a rotary evaporator, diluted with $Et_2O$ (50 mL) and washed twice with 0.1N NaOH (3×20 mL). The organic layer was dried ($Na_2SO4$), decanted and concentrated on a rotary evaporator. The residue was purified by flash chromatography (20% $Et_3N/Et_2O$) to afford 3α(phenylthio)tropane-2a-carboxylic acid methyl ester as a very pale yellow oil (319 mg, 10%) contaminated with the starting material (5% of 319 mg).

3α-(phenylthio)tropane-2β-carboxyUc acid methyl ester was isolated in the following manner: All the non-polar fractions were combined and concentrated. The residue was diluted with $Et_2O$ and washed with 2N HCl (3×20 mL). The aqueous layer was separated, basified with $Na_2CO_3$ (pH=11) and extracted with $Et_2O$ (2×20 mL). The combined organic layers was dried ($Na_2SO_4$), decanted and concentrated to afford a residue which was purified by flash chrormtography (50% of 10% $Et_3N/Et_2O$ in hexanes; $R_f$: 0.33) to yield 3α-(phenylthio)tropane-2β-carboxylic acid methyl ester as a thick oil (2.1 g, 65%).

3α-(phenylthio)tropane-2 β-carboxylic acid methyl ester $^1H$ NMR ($CDCl_3$) 7.37–7.33 (m, 2 H), 7.31–7.25 (m, 2 H), 7.22–7.18 (m, 1 H), 4.12 (ddd, j=7.8, 1.1, 1.1 Hz, 1 H)p 3.72 (sq, 3 H)p 3.61 (m, 1 H), 3.14 (m, 1 H), 2.74 (ddd, j=2.4, 1.1, 1.1 Hz, 1 H), 2.38 (ddd, j=18.6, 7.8, 3.9 Hz, 1 H), 2.68–2.22 (m, 7 H), 1.78 (ddd, J=18.6, 5.6, 3.1 Hz, 1 H). $^{13}C$ ($CDCl_3$) 173.6, 136.4, 130.1, 129.0, 126.5, 63.5, 61.4, 52.1, 51.9, 41.6, 37.6, 36.0, 25.3, 25.0

A tartarate salt of the above compound was made in MeOH with (+)-tartaric acid: [mp: 53–58° C. (fusion]°; $\alpha^{22}$=−37.17° (c 0.955, $CH_3OH$). Anal calcd. for $C_{20}H_{27}NO_8S\cdot H_2O$: C, 52.23; H, 6.36; S, 6.98; N, 3.05. Found: C, 52.07; H, 6.29; S, 9.91; N, 3.05.

Example 28

3α-(Phenylthio)tropane-2β-carboxylic acid methyl ester, 3β-(Phenylthio)tropane-2β-carboxylic acid methyl ester and 3β-(Phenylthio)tropane-2α-carboxylic acid methyl ester

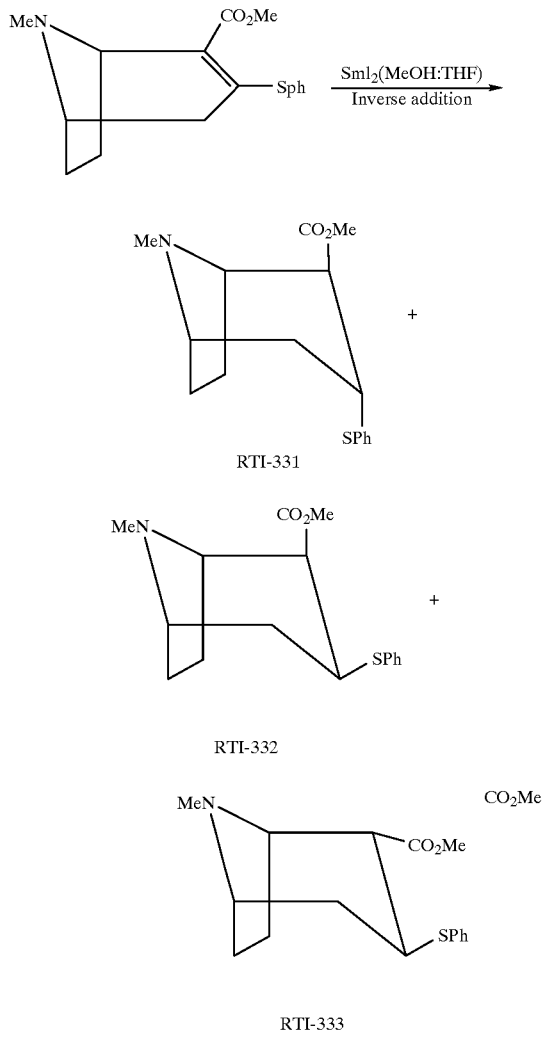

RTI-331

RTI-332

RTI-333

A solution of (1R,5S)-2-(carbomethoxy)-3-(phenylthio)-8-azabicylo-[3.2.1]octane (500 mg, 1.73 mmol) in dry MeOH (20 mL) was added at a rate of 6.5 mL/hr to a −78° C. solution of SmI$_2$ (0.1M in THF, 120 mL). After 3 h of stirring, the cooling bath was removed. After 1 h, the reaction was quenched by the addition of 5% NaOH (10 mL). More water (50 mL) was added and aqueous layer was extracted with Et$_2$O (3×100 mL). The organic layer was washed with brine, separated, dried (Na$_2$SO$_4$), decanted and concentrated to afford 250 mg of a residue which was purified by flash column chromatography (50% of 10% Et$_3$N/Et$_2$O in hexanes) to afford two fractions: fraction 1 (R$_f$=0.33) as a mixture, of 3α-(phenylthio)tropane-2β-carboxylic acid methyl ester and 3β-(phenylthio)tropane-2β-carboxylic acid methyl ester (203 mg, 40.3%); fraction 2 (R$_f$=0.45) Identified as 3 (phenylthio)tropane-2α-carboxylic acid methyl ester.

Fraction 1 was further purified by HPLC using 5% of 1% Et$_3$N/i-PrOH in hexanes to afford 3β-(phenylthio)tropane-2β-carboxylic acid methyl ester (60.5 mg, 12%) and 3a(phenylthio)tropane-2β-carboxylic acid methyl ester (80.6 mg, 16%).

3β-(phenylthio)tropane-2α-carboxyUc acid methyl ester $^1$H NMR (CDCl$_3$) 7.49–7.44 (m, 2 H), 7.34–7.25 (m, 3 H), 3.68 (s, 3 H), 3.40 (ddd, J-12.0, 12.0, 6.1 Hz, 1 H), 3.27 (dd, J=3.7, 2.8 Hz, 1 H), 3.13 (m, 1 H), 2.89 (dd, J=12, 2.8 Hz, 1 H), 2.25 (s, 3 H), 1.90–2.02 (m. 2 H), 1.85–1.77 (m, 2 H), 1.72 (ddd, J=18.5, 6.0, 3.0 Hz, 1 H), 1.57–1.50 (m, 1 H) $^{13}$C (CDCl$_3$) 173.2, 134.5 , 13 .7, 128.7, 127.9, 63.3, 60.3, 51.7, 49.2, 40.4, 37.5, 35.7, 26.7, 23.2.

A tartarate salt of the above compound was made in MeOH with (+)-tartaric acid. [mp: 143–144° C. (fushion)]; α$^{22}$+49.9° (c 0.22, CH$_3$OH). Anal calcd. for C$_{20}$H$_{27}$NO$_8$S.0.5H$_2$O: C, 53.32; H, 6.26; N, 3.11; S, 7.12 Found: C, 53.22; H, 6.23; N, 3.15, S 7.15.

3β-(phenylthio)tropane-2β-carboxylic acid methyl ester $^1$H NMR (CDCl$_3$) 7.51–7.28 (m, 5 H), 3.76 (s, 3 H), 3.53 (m, 1 H), 3.25–3.18 (m, 2 H), 2.85 (ddd, J=5.2, 3.3, 1.1 Hz, 1 H), 2.40 (ddd, J=12.7, 12.7, 3.1 Hz, 1 H), 2.16 (s, 3 H), 2.22–2.09 (m, 2 H), 1.82 (dddd, J=12.7, 5.6, 3.1, 1.1 Hz, 1 H), 1.61–1.48 (m, 2 H) $^{13}$C (CDCl$_3$) 171.9, 137.9, 130.4, 128.9, 126.5, 65.6, 62.7, 53.2, 51.5, 41.6, 41.5, 38.8, 25.4, 25.2.

A tartarate salt of the above compound was made in MeOH with (+)-tartaric acid: [mp: 55–57° C. (fushion)]; α$^{22}$=−83.19° (c 0.47, CH$_3$OH). Anal calcd. for C$_{20}$H$_{27}$NO$_8$S.2H$_2$O: C, 50.30; H, 6.54; N, 2.93. Found: C, 50.59; H, 6.25; N, 2.75.

This invention has been described in both generic terms, and by reference to specific description. No specific description or example is considered binding, unless so identified. Alternate forms and methods will occur to those of ordinary skill in the art, without the exercise of inventive faculty, and remain within the scope of this invention, save as limited by the claims set forth below.

TABLE II

3β-(Substituted phenyl)-2-(heterocyclic)isopams

| Code Name | 2 α/β | het | X | DA [³H]WIN 35,428 | NE [³H]nisoxetine | 5-HT [³H]paroxetine | NE/ DA Ratio | 5HT/DA Ratio |
|---|---|---|---|---|---|---|---|---|
| RTI-87[a] | α | 3,5-dimethyl-1,2,4-oxadiazole (α) | H | 204 ± 29 | 35,782 ± 624 | 29,391 ± 2324 | 175 | 144 |
| RTI-119[a] | β | 3,5-dimethyl-1,2,4-oxadiazole (β) | H | 167 ± 13 | 6985 ± 635 | 40,615 ± 9416 | 42 | 243 |
| RTI-124 | α | 3,5-dimethyl-1,2,4-oxadiazole (α) | H | 1028 ± 65 | 70,993 ± 3563 | 33,085 ± 5434 | 69 | 32 |
| RTI-125 | β | 3,5-dimethyl-1,2,4-oxadiazole (β) | Cl | 4.05 ± 0.57 | 363 ± 36 | 2584 ± 799 | 90 | 638 |
| RTI-126 | β | 3,5-dimethyl-1,2,4-oxadiazole (β) | H | 100 ± 63 | 7876 ± 551 | 3824 ± 418 | 788 | 382 |
| RTI-130 | β | 3-phenyl-5-methyl-1,2,4-oxadiazole (β) | Cl | 1.62 ± 0.02 | 245 ± 13 | 195 ± 4.8 | 151 | 120 |
| RTI-141 | β | 3-(4-methoxyphenyl)-5-methyl-1,2,4-oxadiazole (β) | Cl | 1.81 ± 0.19 | 835 ± 7.5 | 337 ± 43 | 461 | 186 |
| RTI-143 | β | 3-(4-chlorophenyl)-5-methyl-1,2,4-oxadiazole (β) | Cl | 4.1 ± 0.22 | 4069 ± 177 | 404 ± 56 | 991 | 99 |

TABLE II-continued

3β-(Substituted phenyl)-2-(heterocyclic)isopams

| Code Name | 2 α/β | het | X | DA [³H]WIN 35,428 | NE [³H]nisoxetine | 5-HT [³H]paroxetine | NE/DA Ratio | 5HT/DA Ratio |
|---|---|---|---|---|---|---|---|---|
| RTI-144 | β | 5-methyl-3-(4-bromophenyl)-1,2,4-oxadiazole, β | Cl | 3.44 ± 0.36 | 1825 ± 166 | 106 ± 10 | 531 | 31 |
| RTI-147 | β | 1-acetylpyrrolidine, β | Cl | 1.38 ± 0.03 | 3949 ± 72 | 12,393 ± 1207 | 2862 | 8980 |
| RTI-151 | β | 5-methyl-3-phenyl-1,2,4-oxadiazole, β | CH₃ | 2.33 ± 0.26 | 60 ± 2 | 1074 ± 125 | 26 | 461 |
| RTI-152 | α | 5-methyl-3-phenyl-1,2,4-oxadiazole, α | CH₃ | 494 ± 37 | — | 1995 ± 109 | | 4 |
| RTI-154 | β | 5-methyl-3-isopropyl-1,2,4-oxadiazole, β | Cl | 6 ± 0.55 | 135 ± 13 | 3460 ± 245 | 23 | 578 |
| RTI-155 | β | 5-methyl-3-cyclopropyl-1,2,4-oxadiazole, β | Cl | 3.41 ± 0.24 | 177 ± 17 | 4362 ± 415 | 52 | 1279 |
| RTI-156 | β | 1-acetylpiperidine, β | Cl | 6.95 ± 1.21 | 5832 ± 791 | 3468 ± 266 | 839 | 499 |
| RTI-157 | β | 5-methyltetrazole, β | CH₃ | 1557 ± 196 | 37,287 ± 5997 | 43,574 ± 5240 | 24 | 28 |

TABLE II-continued

3β-(Substituted phenyl)-2-(heterocyclic)isopams

| Code Name | 2 α/β | het | X | IC$_{50}$ (nM) DA [$^3$H]WIN 35,428 | NE [$^3$H]nisoxetine | 5-HT [$^3$H]paroxetine | NE/DA Ratio | 5HT/DA Ratio |
|---|---|---|---|---|---|---|---|---|
| RTI-163 | β | 5-(tetrazolyl), β | Cl | 911 ± 6.1 | — | 5456 ± 64 | — | 6 |
| RTI-165 | β | 3,5-dimethylisoxazol-4-yl, β | Cl | 0.59 ± 0.04 | 181 ± 12 | 572 ± 58 | 307 | 970 |
| RTI-171 | β | 3,5-dimethylisoxazol-4-yl, β | CH$_3$ | 0.93 ± 0.09 | — | 3818.25 ± 346.14 | — | 4106 |
| RTI-176 | β | 5-methyl-3-phenylisoxazol-4-yl, β | CH$_3$ | 1.58 ± 0.02 | — | 5109.72 ± 187.10 | — | 3234 |
| RTI-177 | β | 5-methyl-3-phenylisoxazol-4-yl, β | Cl | 1.28 ± 0.18 | — | 2418.21 ± 135.68 | — | 1889 |
| RTI-178 | β | 2-methyl-5-phenyloxazol-4-yl, β | CH$_3$ | 35.4 ± 1.74 | — | 1698.77 ± 166.68 | — | 48 |
| RTI-180 | β | 3,5-dimethylisoxazol-4-yl, β | I | 0.73 ± 0.04 | 67.9 ± 5.25 | 36.35 ± 4.99 | 93 | 50 |

TABLE II-continued

3β-(Substituted phenyl)-2-(heterocyclic)isopams

| Code Name | 2 α/β | het | X | DA [³H]WIN 35,428 | NE [³H]nisoxetine | 5-HT [³H]paroxetine | NE/DA Ratio | 5HT/DA Ratio |
|---|---|---|---|---|---|---|---|---|
| RTI-181 | β | 5-methyl-3-phenyl-isoxazole (β) | I | 2.57 ± 0.14 | 868 ± 95 | 100 ± 9.0 | 337 | 39 |
| RTI-184[b] | β | 3,5-dimethyl-isoxazole (β) | — | 43.3 ± 1.87 | — | 6208.36 ± 395.4 | — | 143 |
| RTI-185[b] | β | 5-methyl-3-phenyl-isoxazole (β) | — | 285 ± 9.22 | — | 12,443.3 ± 1013.14 | — | 43 |
| RTI-188 | β | 5-methyl-2-phenyl-1,3,4-oxadiazole (β) | Cl | 0.78 ± 0.06 | — | 38.15 ± 0.81 | — | 49 |
| RTI-189 | β | 2-methyl-5-phenyl-oxazole (β) | Cl | 19.71 ± 1.98 | — | 1116.18 ± 107.15 | — | 57 |
| RTI-194 | β | 2,5-dimethyl-1,3,4-oxadiazole (β) | CH₃ | 4.45 ± 0.12 | — | 4884.47 ± 155.42 | — | 1098 |
| RTI-195 | β | 5-methyl-2-phenyl-1,3,4-oxadiazole (β) | CH₃ | 47.48 ± 4.76 | — | 22,310.9 ± 822.82 | — | 470 |

TABLE II-continued
3β-(Substituted phenyl)-2-(heterocyclic)isopams
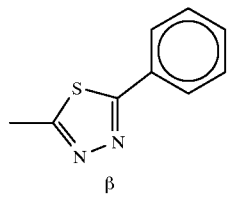
| Code Name | 2 α/β | het | X | DA [³H]WIN 35,428 | NE [³H]nisoxetine | 5-HT [³H]paroxetine | NE/DA Ratio | 5HT/DA Ratio |
|---|---|---|---|---|---|---|---|---|
| RTI-199 | β | 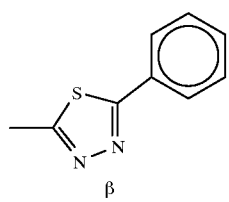 β | $CH_3$ | 35.88 ± 3.40 | 24,320.8 ± 3822 | 51,549.7 ± 4513 | 678 | 1434 |
| RTI-200 | β | 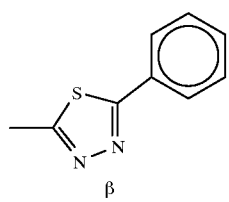 β | Cl | 15.29 ± 2.43 | 4142.08 ± 466 | 18,416.5 ± 1508 | 271 | 1205 |
| RTI-202 | β | 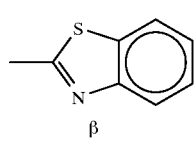 β | Cl | 1.37 ± 0.14 | 398.35 ± 38.97 | 1118.85 ± 120 | 291 | 817 |
| RTI-208 | β | 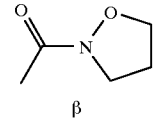 β | Cl | 1.47 ± 0.13 | 997.91 ± 26.39 | 2469.69 ± 56.23 | 679 | 1680 |
| RTI-214 | β | 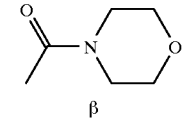 β | Cl | 2.90 ± 0.30 | 8545.18 ± 206.73 | 88,768.6 ± 1854.95 | 2947 | 30,610 |
| RTI-219 | β | 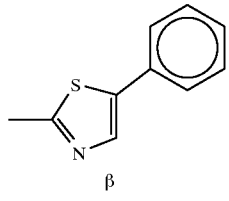 β | Cl | 5.71 ± 0.36 | — | 10,341.5 ± 76.11 | — | 1811 |
| RTI-122 | β | 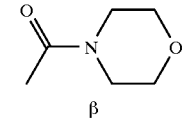 β | $CH_3$ | 11.67 | — | >100,000 | — | >8569 |
| RTI-224 | β | F-1[c] | $CH_3$ | 4.49 ± 0.41 | — | 155.63 ± 2.59 | — | 35 |

TABLE II-continued

3β-(Substituted phenyl)-2-(heterocyclic)isopams

| | | | | IC$_{50}$ (nM) | | | | |
|---|---|---|---|---|---|---|---|---|
| Code Name | 2 α/β | het | X | DA [$^3$H]WIN 35,428 | NE [$^3$H]nisoxetine | 5-HT [$^3$H]paroxetine | NE/ DA Ratio | 5HT/DA Ratio |
| RTI-227 | β | (acetyl-isoxazolidine) β | I | 0.75 ± 0.02 | 357 ± 42.3 | 129 ± 15.8 | 476 | 172 |
| RTI-229 | β | (acetyl-pyrrolidine) β | I | 0.37 ± 0.04 | 991 ± 20.86 | 1728 ± 39.29 | 2678 | 4670 |
| RTI-233 | β | F-2$^c$ | CH$_3$ | 4.38 ± 0.40 | 516 ± 38.5 | 73.61 ± 4.9 | 118 | 17 |
| RTI-235 | β | F-3$^c$ | CH$_3$ | 1.75 ± 0.17 | 402 ± 38.7 | 72.4 ± 2.94 | 230 | 41 |
| RTI-236 | β | B-1$^d$ | CH$_3$ | 1.63 ± 0.27 | 86.8 ± 4.07 | 138 ± 12.4 | 53 | 85 |
| RTI-237 | β | B-2$^d$ | CH$_3$ | 7.27 ± 0.51 | 257.6 ± 25.3 | 363 ± 28.9 | 35 | 50 |
| RTI-244 | β | B-3$^d$ | CH$_3$ | 15.55 ± 1.78 | 1808.7 ± 167 | 33.71 ± 0.73 | 116 | 2 |
| RTI-245 | β | F-4$^c$ | Cl | 77.36 ± 5.77 | — | — | — | — |
| RTI-246 | β | F-4$^c$ | CH$_3$ | 50.3 ± 5.4 | 3000 | — | 60 | — |
| RTI-248 | β | F-3$^c$ | Cl | 9.73 ± 1.01 | 4674 ± 117 | 6.96 ± 0.57 | 480 | 1 |
| RTI-249 | β | F-1$^c$ | Cl | 8.32 ± 0.47 | 5023 ± 518 | 81.6 ± 91 | 604 | 10 |
| RTI-250 | β | (acetyl-pyrrolidine) β | Sn—(CH$_3$)$_3$ | 477 ± 24 | >100,000 | 19,652 ± 1297 | 210 | 41 |
| RTI-253 | β | (acetyl-morpholine) β | I | 3.84 ± 0.33 | 5381 ± 529 | 334.4 ± 18.9 | 1401 | 87 |
| RTI-262 | α | (methyl-benzothiazole) α | Cl | 188.2 ± 5.01 | 595.25 ± 5738 | 5207 ± 488 | 316 | 28 |
| RTI-263 | α | (methyl-phenyl-oxadiazole) α | CH$_3$ | 522.8 ± 48.3 | 4873.7 ± 3235.9 | 65,029 ± 817 | 93 | 124 |
| RTI-264 | α | (methyl-benzothiazole) α | CH$_3$ | 299.3 ± 14.15 | 47,599.7 ± 4621.2 | 8686 ± 738 | 159 | 29 |

TABLE II-continued

3β-(Substituted phenyl)-2-(heterocyclic)isopams

| Code Name | 2 α/β | het | X | IC$_{50}$ (nM) DA [$^3$H]WIN 35,428 | NE [$^3$H]nisoxetine | 5-HT [$^3$H]paroxetine | NE/DA Ratio | 5HT/DA Ratio |
|---|---|---|---|---|---|---|---|---|
| RTI-265 | α | (5-methyl-2-phenyl-1,3,4-oxadiazole), α | Cl | 1098 | 285,634 ± 23,401 | 19,240 ± 1775 | 260 | 18 |
| RTI-266 | β | F-5$^c$ | CH$_3$ | 4.80 ± 0.4 | 836 ± 70 | 842 ± 62.2 | 174 | 175 |
| RTI-267 | β | F-6$^c$ | CH$_3$ | 2.52 ± 0.1 | 324 ± 19 | 455 ± 46 | 129 | 181 |
| RTI-268 | β | F-7$^c$ | CH$_3$ | 3.89 ± 0.3 | 1014 ± 13 | 382 ± 11 | 260 | 98 |
| RTI-269 | β | F-8$^e$ | CH$_3$ | 5.55 ± 0.1 | 788 ± 99 | 986 ± 89 | 142 | 178 |
| RTI-334 | β | (5-methyl-3-ethyl-isoxazole), β | Cl | 0.50 ± 0.03 | 120 ± 10.4 | 3086 ± 153 | 240 | 6172 |
| RTI-335 | β | (5-methyl-3-isopropyl-isoxazole), β | Cl | 1.19 ± 0.12 | 954 ± 97.3 | 2318 ± 153 | 802 | 1948 |
| RTI-336 | β | (5-methyl-3-(4-methylphenyl)-isoxazole), β | Cl | 4.09 ± 0.44 | 1714 ± 38.5 | 5741 ± 421 | 419 | 1404 |
| RTI-337 | β | (5-methyl-3-tert-butyl-isoxazole), β | Cl | 7.31 ± 0.61 | 6321 ± 703 | 36,842 ± 3616 | 865 | 5040 |
| RTI-345 | β | (5-methyl-3-(4-chlorophenyl)-isoxazole), β | Cl | 6.42 ± 0.46 | 5290.4 ± 448.99 | >76,000 | 824 | >11,838 |

TABLE II-continued
3β-(Substituted phenyl)-2-(heterocyclic)isopams
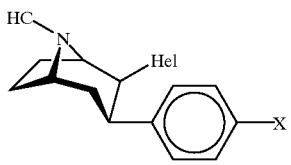
| Code Name | 2 α/β | het | X | DA [³H]WIN 35,428 | NE [³H]nisoxetine | 5-HT [³H]paroxetine | NE/DA Ratio | 5HT/DA Ratio |
|---|---|---|---|---|---|---|---|---|
| | | | | | IC₅₀ (nM) | | | |
| RTI-346 | β | (5-methyl-3-(4-methoxyphenyl)isoxazole), β | Cl | 1.57 ± 0.10 | 762.01 ± 37.8 | 5880.4 ± 179 | 485 | 3746 |
| RTI-347 | β | (5-methyl-3-(4-fluorophenyl)isoxazole), β | Cl | 1.86 ± 0.09 | 918.4 ± 108.34 | 7256.95 ± 210 | 494 | 3902 |
| RTI-354 | β | (5-methyl-3-ethylisoxazole), β | CH₃ | 1.62 ± 0.10 | 299 ± 22 | 6400 ± 253 | 185 | 3951 |
ᵃThis is a 3-alpha-derivative
ᵇThis is a 3-beta-benzayloxy derivative
ᶜ
F-1 = 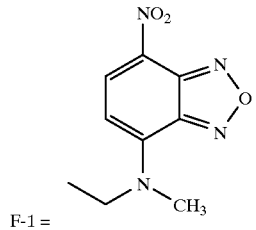
F-2 = 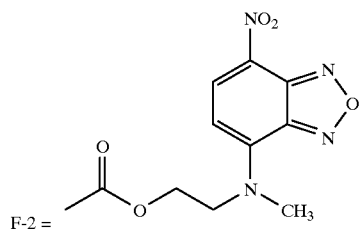

TABLE II-continued

3β-(Substituted phenyl)-2-(heterocyclic)isopams

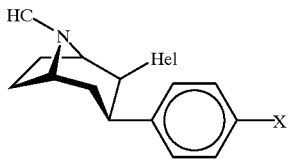

| | | | | IC$_{50}$ (nM) | | | | |
|---|---|---|---|---|---|---|---|---|
| Code Name | 2 α/β | het | X | DA [$^3$H]WIN 35,428 | NE [$^3$H]nisoxetine | 5-HT [$^3$H]paroxetine | NE/ DA Ratio | 5HT/DA Ratio |

F-3 = [structure: 4-nitrobenzofurazan-NH-phenyl-CH$_2$CH$_2$-O-C(=O)-CH$_3$]

F-4 = [structure: 4-nitrobenzofurazan-NH-CH$_2$CH$_3$]

F-5 = [structure: 4-nitrobenzofurazan-N(CH$_3$)-CH$_2$-C(=O)-N(CH$_3$)-CH$_2$CH$_3$]

F-6 = [structure: 4-nitrobenzofurazan-N(CH$_3$)-CH$_2$CH$_2$-C(=O)-NH-CH$_2$-C(=O)-N(CH$_3$)-CH$_2$CH$_3$]

TABLE II-continued
3β-(Substituted phenyl)-2-(heterocyclic)isopams
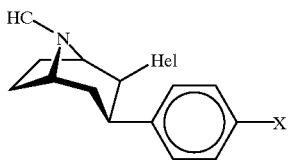
| | | | | IC$_{50}$ (nM) | | | | |
|---|---|---|---|---|---|---|---|---|
| Code Name | 2 α/β | het | X | DA [$^3$H]WIN 35,428 | NE [$^3$H]nisoxetine | 5-HT [$^3$H]paroxetine | NE/ DA Ratio | 5HT/DA Ratio |
F-7 =
F-8 =
d
B-2 =
B-3 =

TABLE III

Comparison of Transporter Binding Potencies

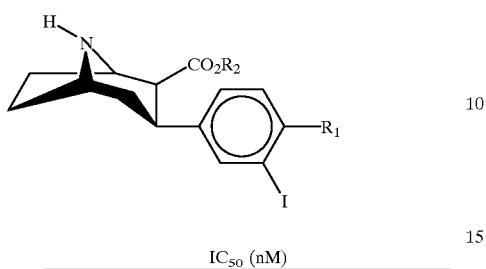

| | | | IC$_{50}$ (nM) | | |
|---|---|---|---|---|---|
| RTI No. | R$_1$ | R$_2$ | 5-HT [$^3$H]Paroxetine | DA [$^3$H]WIN 35,428 | NE [$^3$H]Nisoxetine |
| 279 | CH$_3$ | CH$_3$ | 1.06 ± 0.39 | 5.98 ± 0.48 | 74.3 ± 3.8 |
| 353 | C$_2$H$_5$ | CH$_3$ | 0.69 ± 0.07 | 331 ± 17 | 148 ± 9.2 |
| Paroxetine* | | | 0.28 ± 0.02 | 623 ± 25 | 313 |

5-HT = serotonin
DA = dopamine
NE = norepinephrine
*Aropax; Seroxat; see Merck Index.

TABLE IV

3β-(Substituted phenyl)-2β-(substituted)tropanes

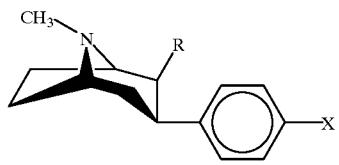

| | | | IC$_{50}$ (nM) | | |
|---|---|---|---|---|---|
| Code Name | R | X | DA [$^3$H]-WIN 35,428 | NE [$^3$H]-nisoxetine | 5-HT [$^3$H]-paroxetine |
| RTI-93 | CH$_2$OH | Cl | 1.53 ± 0.15 | 43.8 ± 6.4 | 204 ± 16 |
| RTI-99 | CH$_2$OH | Br | 1.49 ± 0.05 | | 51 ± 4.6 |
| RTI-100 | CH$_2$OH | F | 47 ± 4.6 | | 4741 ± 335 |
| RTI-101 | CH$_2$OH | I | 2.2 ± 0.19 | | 26 ± 3.2 |
| RTI-102 | CO$_2$H | I | 474 ± 57 | 43,400 ± 5500 | 1928 ± 120 |
| RTI-103 | CO$_2$H | Br | 278 ± 43 | 17,400 ± 1400 | 3070 ± 208 |
| RTI-104 | CO$_2$H | F | 2744 ± 141 | >100,000 | >100,000 |
| RTI-105 | CH$_2$OAc | Cl | 1.60 ± 0.05 | 127 ± 5.9 | 143 ± 25 |
| RTI-108 | CH$_2$Cl | Cl | 2.64 ± 0.31 | 129 ± 15 | 98 ± 8.7 |
| RTI-123 | CH$_2$OCOC$_6$H$_5$ | Cl | 1.78 ± 0.09 | 393 ± 30 | 3.53 ± 0.58 |
| RTI-131 | CH$_2$NH$_2$ | CH$_3$ | 10.5 ± 1.7 | 120 ± 20 | 855 ± 52 |
| RTI-132 | CH$_2$N(CH$_3$)$_2$ | CH$_3$ | 3.48 ± 0.11 | 137 ± 11 | 208 ± 18 |
| RTI-139 | CH$_3$ | Cl | 1.67 ± 0.13 | 57 ± 2.6 | 85 ± 9.3 |
| RTI-145 | CH$_2$OCO$_2$CH$_3$ | Cl | 9.6 ± 0.42 | 1478 ± 96 | 2930 ± 181 |
| RTI-158 | CN | CH$_3$ | 57 ± 7.3 | 1624 ± 136 | 5095 ± 315 |
| RTI-161 | CN | Cl | 13.1 ± 0.76 | 2516 ± 253 | 1887 ± 134 |
| RTI-164 | CH$_2$NHCH$_3$ | CH$_3$ | 13.6 ± 2.03 | 280 ± 19 | 2246 ± 94 |
| RTI-230 | —C(CH$_3$)=CH$_2$ | Cl | 1.28 ± 0.17 | 141 ± 16 | 57 ± 5.0 |
| RTI-239 | CH(CH$_3$)$_2$ | CH$_3$ | 0.61 ± 0.07 | 35.6 ± 2.57 | 114 ± 3.69 |
| RTI-240 | CH(CH$_3$)$_2$ | Cl | 1.38 ± 0.03 | 84.5 ± 3.09 | 38.4 ± 2.31 |
| RTI-241 | CH$_2$CO$_2$CH$_3$ | CH$_3$ | 1.02 ± 0.06 | 124 ± 3.56 | 618 ± 28 |

TABLE V

Binding Affinities of 3–6 at the DA, 5-HT, and NE Transporters

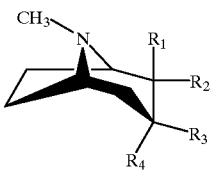

| | | | | | IC$_{50}$ (nM) | | |
|---|---|---|---|---|---|---|---|
| | R$_1$ | R$_2$ | R$_3$ | R$_4$ | DA | 5-HT | NE |
| cocaine (1)[a] | — | — | — | — | 89 ± 4.8 | 1050 ± 89 | 3300 ± 290 |
| 2[a] | —CO$_2$CH$_3$ | —H | —Ph | —H | 23 ± 5 | 1960 ± 61 | 920 ± 73 |
| (±)-3 | —OH | —Ph | —Ph | —H | 2860 ± 290 | 37,190 ± 2410 | >175,000 |
| (±)-4 (2-tropene) | | —Ph | —Ph | | 550 ± 43 | 47,800 ± 4910 | 21,400 ± 1630 |
| (±)-5 | —Ph | —H | —Ph | —H | 28 ± 1.9 | 34,700 ± 3950 | 2670 ± 6270 |
| (±)-6 | —H | —Ph | —H | —Ph | 1270 ± 120 | 18,600 ± 1880 | 2770 ± 280 |

[a]The IC$_{50}$ values are from ref. 15.

TABLE VI

NMR Characteristics of 3, 5, and 6

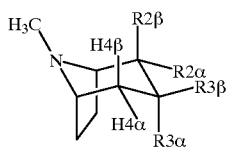

| Compd | R2β | R2α | R3β | R3α | J$_{23}$ (Hz) | J$_{34β}$(Hz) | characteristic noe interactions |
|---|---|---|---|---|---|---|---|
| (±)-3 | OH | Ph | Ph | H | — | 12.5 | H7-Ph2α |
| (±)-5 | Ph | H | Ph | H | 6.6 | 13.0 | H3α-H6, H2α-H7 |
| (±)-6 | H | Ph | H | Ph | 8.0 | 8.0 | H2-H4β, H2β-NMe |

TABLE VII

Elemental Analysis

| | Calcd. | | | Found | | |
|---|---|---|---|---|---|---|
| Compd | C | H | N | C | H | N |
| C$_{20}$H$_{23}$NO.HCl.0.75H$_2$O | 69.96 | 7.49 | 4.08 | 70.08 | 7.13 | 4.02 |
| C$_{20}$H$_{21}$N.HCl.0.75H$_2$O | 73.83 | 7.28 | 4.30 | 74.04 | 7.25 | 4.25 |
| C$_{20}$H$_{23}$N.HCl.0.5H$_2$O | 74.40 | 7.80 | 4.34 | 74.17 | 7.88 | 4.25 |
| C$_{20}$H$_{23}$N.HCl.0.5H$_2$O | 74.40 | 7.80 | 4.34 | 74.22 | 7.55 | 4.26 |
| C$_{22}$H$_{25}$NO$_3$ | 75.18 | 7.17 | 3.99 | 74.99 | 7.22 | 3.94 |
| C$_{22}$H$_{23}$NO$_2$ | 79.25 | 6.95 | 4.20 | 79.22 | 6.99 | 4.16 |
| C$_{22}$H$_{25}$NO$_2$.0.25H$_2$O | 77.73 | 7.56 | 4.12 | 77.94 | 7.54 | 4.10 |
| C$_{22}$H$_{25}$NO$_2$ | 78.77 | 7.51 | 4.18 | 78.65 | 7.54 | 4.23 |

What is claimed is:

1. A method of controlling an invertebrate pest, comprising contacting said pest with an effective pest-controlling amount of a compound having the formula:

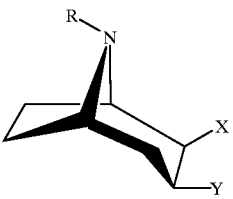

wherein R is H, CH$_3$(CH$_2$)$_n$, which may be branched or unbranched, and wherein n=0–10, C$_6$H$_5$(CH$_2$)$_m$, wherein m=0–10, and X=

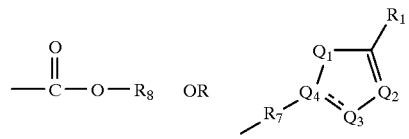

wherein Q$_1$, Q$_2$, Q$_3$ and Q$_4$ are the same or different and may be C, S, N or O, with the proviso that at least one of Q$_1$, Q$_2$, Q$_3$ and Q$_4$ are N;

R$_4$ is hydrogen; methyl; phenyl optionally substituted with halogen, methoxy or C$_{1-6}$ alkyl; cyclopropyl or C$_{1-6}$ alkyl;

- - - - is a single or double bond; and

R$_7$ is a single bond, —C=O or CH$_2$;

R$_8$ is phenyl, C$_{1-6}$ alkyl-substituted phenyl;

or Q$_2$ and R$_4$ form a phenyl ring;

or X=

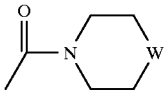

wherein W=(CH$_2$)$_n$, wherein n=0–4 or O, or X=

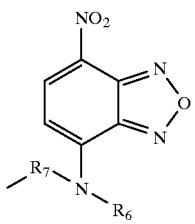

wherein

R$_6$ is hydrogen, methyl, amino or nitro;
R$_7$ is methylene, —CO$_2$—CH$_2$—CH$_2$—, —CO$_2$CH$_2$CH$_2$C$_6$H$_5$— or —CH$_2$—NCH$_2$—CO—CH$_2$—NH—CO—R$_{16}$— and
R$_{16}$ is —CH$_2$—CH$_2$—, CH$_2$NH—CO—CH$_2$— or CH$_2$—NH—CO—CH$_2$—NH—CO—CH$_2$ or X=

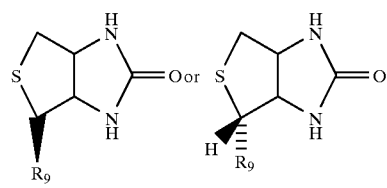

wherein R$_9$ is —CH$_2$NHCO—CH$_2$CH$_2$CH$_2$CH$_2$—, —CH$_2$—NCH$_3$—CO—CH$_2$CH$_2$CH$_2$CH$_2$ or —CO—O—CH$_2$—CH$_2$C$_6$H$_5$—NH—CO—CH$_2$—CH$_2$—CH$_2$—CH$_2$— and Y=

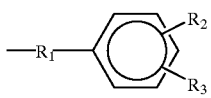

wherein

R$_1$ is a single bond, S, —O—CO— and
R$_2$ and R$_3$ are hydrogen, halogen, CN, CF$_3$, NO$_2$, N$_3$, OR, CONH$_2$, CO$_2$R, C$_{1-6}$ alkyl, NR$_{10}$R$_{11}$, NHCOR$_{11}$, NHCO$_2$R$_{12}$,

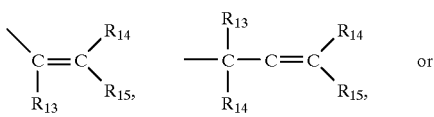

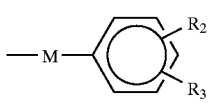

wherein R$_{13}$, R$_{14}$ and R$_{15}$ are H or C$_{1-6}$ alkyl and M=(CH$_2$)$_x$ wherein x=1–8, —CH=CH—, or —C—C—, C$_{1-6}$ alkyl, C$_{3-8}$ cycloalkyl, C$_{1-4}$ alkoxy, C$_{1-6}$ alkynyl, amino, acylamido or Sn(CH$_3$)$_3$ wherein R$_{10}$, R$_{11}$ and R$_{12}$ are C$_{1-6}$ alkyl.

2. The method of claim 1, wherein X is

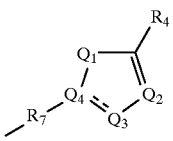

wherein Q$_1$, Q$_2$, Q$_3$ and Q$_4$ are the same or different and may be C, S, N or O, with the proviso that at least one of Q$_1$, Q$_2$, Q$_3$ and Q$_4$ are N;

R$_4$ is hydrogen; methyl; phenyl optionally substituted with halogen or methoxy; cyclopropyl or C$_{1-4}$ alkyl;

- - - - is a single or double bond; and

R$_7$ is a single bond —CO or —COO;

or Q$_2$ and R$_4$ form a phenyl ring.

3. The method of claim 1, wherein X is

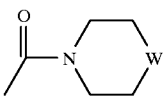

wherein W=(CH$_2$)$_n$, wherein n=0–4, or O.

4. The method of claim 1, wherein X is

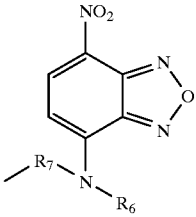

wherein

R$_6$ is hydrogen, methyl, amino or nitro;
R$_7$ is methylene, —CO$_2$—CH$_2$—CH$_2$—, —CO$_2$CH$_2$CH$_2$C$_6$H$_5$— or —CH$_2$—NCH$_3$—CO—CH$_2$—NH—CO—R$_{16}$— and
R$_{16}$ is —CH$_2$—CH$_2$—, CH$_2$NH—CH$_2$— or CH$_2$—NH—CO—CH$_2$—NH—CO—CH$_2$—.

5. The method of claim 1, wherein X is

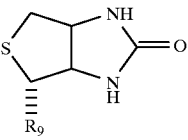

wherein R$_9$ is —CH$_2$NHCO—CH$_2$CH$_2$CH$_2$CH$_2$—, —CH$_2$—NCH$_3$—CO—CH$_2$CH$_2$CH$_2$CH$_2$— or —CO—O—CH$_2$—CH$_2$C$_6$H$_5$—NH—CO—CH$_2$—CH$_2$—CH$_2$—CH$_3$—

6. A method for inhibiting the feeding of an invertebrate pest comprising contacting said pest with an effective feeding-inhibiting amount of a compound having the formula:

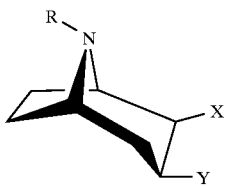

wherein R is H, $CH_3(CH_2)_n$, which may be branched or unbranched, and wherein n=0–10, $C_6H_5(CH_2)_m$, wherein m=0–10, and X=

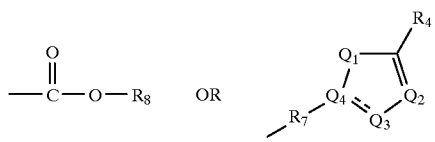

wherein $Q_1$, $Q_2$, $Q_3$ and $Q_4$ are the same or different and may be C, S, N or O, with the proviso that at least one of $Q_1$, $Q_2$, $Q_3$ and $Q_4$ are N;

$R_4$ is hydrogen; methyl; phenyl optionally substituted with halogen, methoxy or $C_{1-6}$ alkyl; cyclopropyl or $C_{1-6}$ alkyl;

- - - - is a single or double bond; and $R_7$ is a single bond, —C=O or $CH_2$;

$R_8$ is phenyl, $C_{1-6}$ alkyl-substituted phenyl;

or $Q_2$ and $R_4$ form a phenyl ring;

or X=

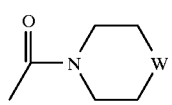

wherein W=$(CH_2)_n$, wherein n=0–4 or O, or X=

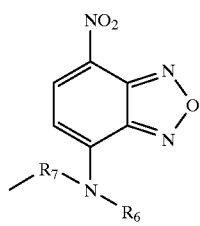

wherein $R_6$ is hydrogen, methyl, amino or nitro;

$R_7$ is methylene, —$CO_2$—$CH_2$—$CH_2$—, —$CO_2CH_2CH_2C_6H_5$— or —$CH_2$—$NCH_3$—CO—$CH_2$—NH—CO—$R_{16}$— and $R_{16}$ is —$CH_2$—$CH_2$—, $CH_2NH$—CO—$CH_2$— or $CH_2$—NH—CO—$CH_2$—NH—CO—$CH_2$— or X=

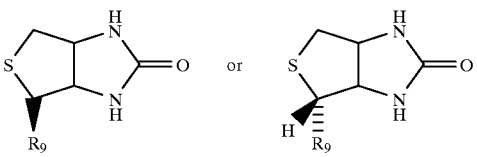

wherein $R_9$ is —$CH_2NHCO$—$CH_2CH_2CH_2CH_2$—, —$CH_2$—$NCH_3$—CO—$CH_2CH_2CH_2CH_2$ or —CO—O—$CH_2C_6H_5$—NH—CO—$CH_2$—$CH_2$—$CH_2$—$CH_2$— and Y=

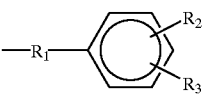

wherein $R_1$ is a single bond, S, O—CO or —COO— and $R_2$ and $R_3$ are hydrogen, halogen, CN, $CF_3$, $NO_2$, $N_3$, OR, $CONH_2$, $CO_2R$, $C_{1-6}$ alkyl, $NR_{10}R_{11}$, $NHCOR_{11}$, $NHCO_2R_{12}$,

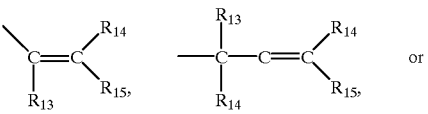

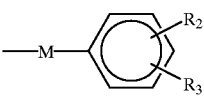

wherein $R_{13}$, $R_{14}$ and $R_{15}$ are H or $C_{1-6}$ alkyl and M=$(CH_2)_x$ wherein x=1–8, —CH=CH—, or —C≡C—, $C_{1-6}$ alkyl, $C_{3-8}$ cycloalkyl, $C_{1-4}$ alkoxy, $C_{1-6}$ alkynyl, amino, acylamido or $Sn(CH_3)_3$ wherein $R_{10}$, $R_{11}$ and $R_{12}$ are $C_{1-6}$ alkyl.

7. The method of claim 6, wherein X is

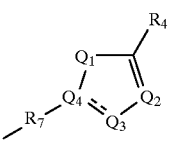

wherein $Q_1$, $Q_2$, $Q_3$ and $Q_4$ are the same or different and may be C, S, N or O, with the proviso that at least one of $Q_1$, $Q_2$, $Q_3$ and $Q_4$ are N;

$R_4$ is hydrogen; methyl; phenyl optionally substituted with halogen or methoxy; cyclopropyl or $C_{1-4}$ alkyl;

- - - - is a single or double bond; and $R_7$ is a single bond —CO or —COO;

or $Q_2$ and $R_4$ form a phenyl ring.

8. The method of claim 6, wherein X is

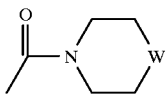

wherein W is $(CH_2)_n$, wherein n=0–4, or O.

9. The method of claim 6, wherein X is

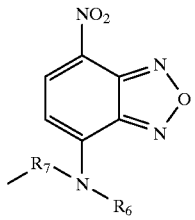

wherein $R_6$ is hydrogen, methyl, amino or nitro;

$R_7$ is methylene, $-CO_2-CH_2-CH_2-$, $-CO_2CH_2CH_2C_6H_5-$ or $-CH_2-NCH_3-CO-CH_2-NH-CO-R_{16}-$ and $R_{16}$ is $-CH_2-CH_2-$, $CH_2NH-CO-CH_2-$ or $CH_2-NH-CO-CH_2-NH-CO-CH_2-$.

10. The method of claim 6, wherein X is

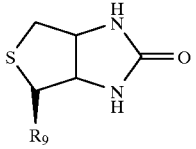

wherein $R_9$ is $-CH_2NHCO-CH_2CH_2CH_2CH_2-$, $-CH_2-NCH_3-CHO-CH_2CH_2CH_2CH_2$ or $-CO-O-CH_2-CH_2C_6H_5-NH-CO-CH_2-CH_2-CH_2CH_2-$.

* * * * *

UNITED STATES PATENT AND TRADEMARK OFFICE
CERTIFICATE OF CORRECTION

PATENT NO. : 5,935,953
DATED : August 10, 1999
INVENTOR(S) : Michael Kuhar, et al.

It is certified that error appears in the above-identified patent and that said Letters Patent is hereby corrected as shown below:

Claim 1, column 92,
Lines 40-45 reads

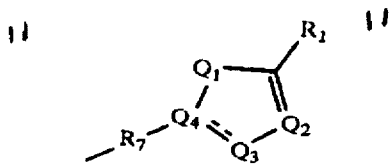

should read --

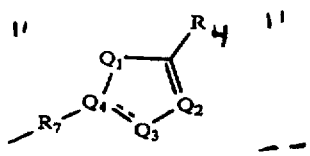

--

Signed and Sealed this

Twenty fifth Day of September, 2001

Attest:

NICHOLAS P. GODICI
Attesting Officer    Acting Director of the United States Patent and Trademark Office